US010758348B2

(12) United States Patent
Ratz et al.

(10) Patent No.: US 10,758,348 B2
(45) Date of Patent: Sep. 1, 2020

(54) SUPRA AND SUB-ANNULAR MITRAL VALVE DELIVERY SYSTEM

(71) Applicant: Edwards Lifesciences Corporation, Irvine, CA (US)

(72) Inventors: J. Brent Ratz, Winchester, MA (US); Glen T. Rabito, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 292 days.

(21) Appl. No.: 15/798,035

(22) Filed: Oct. 30, 2017

(65) Prior Publication Data
US 2018/0116790 A1 May 3, 2018

Related U.S. Application Data

(60) Provisional application No. 62/416,417, filed on Nov. 2, 2016.

(51) Int. Cl.
*A61F 2/24* (2006.01)
(52) U.S. Cl.
CPC ............ *A61F 2/243* (2013.01); *A61F 2/2418* (2013.01); *A61F 2/2436* (2013.01);
(Continued)
(58) Field of Classification Search
CPC .............. A61F 2220/0008; A61F 2/243; A61F 2/2436; A61F 2/2439
See application file for complete search history.

(56) References Cited

U.S. PATENT DOCUMENTS 3,657,744 A    4/1972  Ersek
3,671,979 A    6/1972  Moulopoulos
(Continued)

FOREIGN PATENT DOCUMENTS

CA    2304325 A1    10/2000
CA    2827556 A1    7/2012
(Continued)

OTHER PUBLICATIONS

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
(Continued)

*Primary Examiner* — Gregory A Anderson
(74) *Attorney, Agent, or Firm* — Knobbe Martens Olson & Bear LLP

(57) ABSTRACT

Methods are described herein for delivering a replacement mitral valve to a native mitral valve location. In one method, ventricular anchors of the replacement mitral valve are released and allowed to reverse orientation while positioned in the left atrium of a human heart. After reversing orientation, the ventricular anchors extend in a generally proximal direction. The ventricular anchors can then be advanced through the mitral annulus into the left ventricle and then moved back toward the left atrium to capture native mitral valve leaflets between the main body and the ventricular anchors of the replacement mitral valve. In one modification, the ventricular anchors are allowed to reverse orientation at a level adjacent the mitral annulus. The implantation methods described herein are preferably performed via a transseptal delivery approach or a transapical delivery approach.

20 Claims, 44 Drawing Sheets

(52) U.S. Cl.
CPC .... *A61F 2/2439* (2013.01); *A61F 2220/0008* (2013.01); *A61F 2250/0039* (2013.01)

(56) References Cited

U.S. PATENT DOCUMENTS

| | | | |
|---|---|---|---|
| 3,739,402 A | 6/1973 | Cooley et al. | |
| 4,056,854 A | 11/1977 | Boretos et al. | |
| 4,079,468 A | 3/1978 | Liotta et al. | |
| 4,204,283 A | 5/1980 | Bellhouse et al. | |
| 4,222,126 A | 9/1980 | Boretos et al. | |
| 4,265,694 A | 5/1981 | Boretos et al. | |
| 4,339,831 A | 7/1982 | Johnson | |
| 4,340,977 A | 7/1982 | Brownlee et al. | |
| 4,470,157 A | 9/1984 | Love | |
| 4,477,930 A | 10/1984 | Totten et al. | |
| 4,490,859 A | 1/1985 | Black et al. | |
| 4,553,545 A | 11/1985 | Maass et al. | |
| 4,777,951 A | 10/1988 | Cribier et al. | |
| 4,865,600 A | 9/1989 | Carpentier et al. | |
| 4,994,077 A | 2/1991 | Dobben | |
| 5,326,371 A | 7/1994 | Love et al. | |
| 5,332,402 A | 7/1994 | Teitelbaum | |
| 5,370,685 A | 12/1994 | Stevens | |
| 5,411,552 A | 5/1995 | Andersen et al. | |
| 5,415,667 A | 5/1995 | Frater | |
| 5,545,214 A | 8/1996 | Stevens | |
| 5,554,185 A | 9/1996 | Block et al. | |
| 5,697,382 A | 12/1997 | Love et al. | |
| 5,840,081 A | 11/1998 | Andersen et al. | |
| 5,855,601 A | 1/1999 | Bessler et al. | |
| 5,957,949 A | 9/1999 | Leonhardt et al. | |
| 6,086,612 A | 7/2000 | Jansen | |
| 6,113,631 A | 9/2000 | Jansen | |
| 6,168,614 B1 | 1/2001 | Andersen et al. | |
| 6,251,093 B1 | 6/2001 | Valley et al. | |
| 6,312,465 B1 | 11/2001 | Griffin et al. | |
| 6,358,277 B1 | 3/2002 | Duran | |
| 6,440,164 B1 | 8/2002 | DiMatteo et al. | |
| 6,458,153 B1 | 10/2002 | Bailey et al. | |
| 6,482,228 B1 | 11/2002 | Norred | |
| 6,527,800 B1 | 3/2003 | McGuckin, Jr. et al. | |
| 6,582,462 B1 | 6/2003 | Andersen et al. | |
| 6,610,088 B1 | 8/2003 | Gabbay | |
| 6,629,534 B1 | 10/2003 | St. Goar et al. | |
| 6,652,578 B2 | 11/2003 | Bailey et al. | |
| 6,676,698 B2 | 1/2004 | McGuckin, Jr. et al. | |
| 6,695,878 B2 | 2/2004 | McGuckin, Jr. et al. | |
| 6,712,836 B1 | 3/2004 | Berg et al. | |
| 6,730,118 B2 | 5/2004 | Spenser et al. | |
| 6,767,362 B2 | 7/2004 | Schreck | |
| 6,780,200 B2 | 8/2004 | Jansen | |
| 6,790,229 B1 | 9/2004 | Berreklouw | |
| 6,790,230 B2 | 9/2004 | Beyersdorf et al. | |
| 6,875,231 B2 | 4/2005 | Anduiza et al. | |
| 6,893,460 B2 | 5/2005 | Spenser et al. | |
| 6,908,481 B2 | 6/2005 | Cribier | |
| 7,018,406 B2 | 3/2006 | Seguin et al. | |
| 7,186,265 B2 | 3/2007 | Sharkawy et al. | |
| 7,198,646 B2 | 4/2007 | Figulla et al. | |
| 7,201,772 B2 | 4/2007 | Schwammenthal et al. | |
| 7,276,078 B2 | 10/2007 | Spenser et al. | |
| 7,329,278 B2 | 2/2008 | Seguin et al. | |
| 7,381,219 B2 | 6/2008 | Salahieh et al. | |
| 7,393,360 B2 | 7/2008 | Spenser et al. | |
| 7,429,269 B2 | 9/2008 | Schwammenthal et al. | |
| 7,442,204 B2 | 10/2008 | Schwammenthal et al. | |
| 7,445,631 B2 | 11/2008 | Salahieh et al. | |
| 7,462,191 B2 | 12/2008 | Spenser et al. | |
| 7,510,575 B2 | 3/2009 | Spenser et al. | |
| 7,524,330 B2 | 4/2009 | Berreklouw | |
| 7,585,321 B2 | 9/2009 | Cribier | |
| 7,618,446 B2 | 11/2009 | Andersen et al. | |
| 7,621,948 B2 | 11/2009 | Herrmann et al. | |
| 7,628,805 B2 | 12/2009 | Spenser et al. | |
| 7,748,389 B2 | 7/2010 | Salahieh et al. | |
| 7,753,949 B2 | 7/2010 | Lamphere et al. | |
| 7,803,185 B2 | 9/2010 | Gabbay | |
| 7,806,919 B2 | 10/2010 | Bloom et al. | |
| 7,815,673 B2 | 10/2010 | Bloom et al. | |
| 7,824,443 B2 | 11/2010 | Salahieh et al. | |
| 7,892,281 B2 | 2/2011 | Seguin et al. | |
| 7,914,569 B2 | 3/2011 | Nguyen et al. | |
| 7,947,075 B2 | 5/2011 | Goetz et al. | |
| 7,959,672 B2 | 6/2011 | Salahieh et al. | |
| 7,972,378 B2 | 7/2011 | Tabor et al. | |
| 7,981,151 B2 | 7/2011 | Rowe | |
| 7,993,392 B2 | 8/2011 | Righini et al. | |
| 8,016,877 B2 | 9/2011 | Seguin et al. | |
| 8,048,153 B2 | 11/2011 | Salahieh et al. | |
| 8,052,750 B2 | 11/2011 | Tuval et al. | |
| 8,070,800 B2 | 12/2011 | Lock et al. | |
| 8,070,802 B2 | 12/2011 | Lamphere et al. | |
| 8,075,615 B2 | 12/2011 | Eberhardt et al. | |
| 8,080,054 B2 | 12/2011 | Rowe | |
| 8,092,520 B2 | 1/2012 | Quadri | |
| 8,109,996 B2 | 2/2012 | Stacchino et al. | |
| 8,118,866 B2 | 2/2012 | Herrmann et al. | |
| 8,136,218 B2 | 3/2012 | Millwee et al. | |
| 8,137,398 B2 | 3/2012 | Tuval et al. | |
| 8,157,852 B2 | 4/2012 | Bloom et al. | |
| 8,167,934 B2 | 5/2012 | Styrc et al. | |
| 8,182,528 B2 | 5/2012 | Salahieh et al. | |
| 8,182,530 B2 | 5/2012 | Huber | |
| 8,216,301 B2 | 7/2012 | Bonhoeffer et al. | |
| 8,219,229 B2 | 7/2012 | Cao et al. | |
| 8,220,121 B2 | 7/2012 | Hendriksen et al. | |
| 8,221,493 B2 | 7/2012 | Boyle et al. | |
| 8,226,710 B2 | 7/2012 | Nguyen et al. | |
| 8,236,045 B2 | 8/2012 | Benichou et al. | |
| 8,246,675 B2 | 8/2012 | Zegdi | |
| 8,246,678 B2 | 8/2012 | Salahieh et al. | |
| 8,252,051 B2 | 8/2012 | Chau et al. | |
| 8,252,052 B2 | 8/2012 | Salahieh et al. | |
| 8,287,584 B2 | 10/2012 | Salahieh et al. | |
| 8,303,653 B2 | 11/2012 | Bonhoeffer et al. | |
| 8,313,525 B2 | 11/2012 | Tuval et al. | |
| 8,323,335 B2 | 12/2012 | Rowe et al. | |
| 8,348,995 B2 | 1/2013 | Tuval et al. | |
| 8,353,953 B2 | 1/2013 | Giannetti et al. | |
| 8,403,983 B2 | 3/2013 | Quadri et al. | |
| 8,414,644 B2 | 4/2013 | Quadri et al. | |
| 8,414,645 B2 | 4/2013 | Dwork et al. | |
| 8,444,689 B2 | 5/2013 | Zhang | |
| 8,449,599 B2 * | 5/2013 | Chau | A61F 2/2418 623/1.26 |
| 8,454,685 B2 | 6/2013 | Hariton et al. | |
| 8,460,368 B2 | 6/2013 | Taylor et al. | |
| 8,470,023 B2 | 6/2013 | Eidenschink et al. | |
| 8,475,521 B2 | 7/2013 | Suri et al. | |
| 8,475,523 B2 | 7/2013 | Duffy | |
| 8,479,380 B2 | 7/2013 | Malewicz et al. | |
| 8,486,137 B2 | 7/2013 | Suri et al. | |
| 8,491,650 B2 | 7/2013 | Wiemeyer et al. | |
| 8,500,798 B2 | 8/2013 | Rowe et al. | |
| 8,511,244 B2 | 8/2013 | Holecek et al. | |
| 8,512,401 B2 | 8/2013 | Murray, III et al. | |
| 8,518,106 B2 | 8/2013 | Duffy et al. | |
| 8,562,663 B2 | 10/2013 | Mearns et al. | |
| 8,579,963 B2 | 11/2013 | Tabor | |
| 8,579,964 B2 | 11/2013 | Lane et al. | |
| 8,579,965 B2 | 11/2013 | Bonhoeffer et al. | |
| 8,585,755 B2 | 11/2013 | Chau et al. | |
| 8,585,756 B2 | 11/2013 | Bonhoeffer et al. | |
| 8,591,570 B2 | 11/2013 | Revuelta et al. | |
| 8,597,348 B2 | 12/2013 | Rowe et al. | |
| 8,617,236 B2 | 12/2013 | Paul et al. | |
| 8,640,521 B2 | 2/2014 | Righini et al. | |
| 8,647,381 B2 | 2/2014 | Essinger et al. | |
| 8,652,145 B2 | 2/2014 | Maimon et al. | |
| 8,652,201 B2 | 2/2014 | Oberti et al. | |
| 8,652,203 B2 | 2/2014 | Quadri et al. | |
| 8,668,733 B2 | 3/2014 | Haug et al. | |
| 8,673,000 B2 | 3/2014 | Tabor et al. | |
| 8,679,174 B2 | 3/2014 | Ottma et al. | |

(56) References Cited

U.S. PATENT DOCUMENTS

| | | |
|---|---|---|
| 8,679,404 B2 | 3/2014 | Liburd et al. |
| 8,685,086 B2 | 4/2014 | Navia et al. |
| 8,721,708 B2 | 5/2014 | Seguin et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,740,974 B2 | 6/2014 | Lambrecht et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,344 B2 | 7/2014 | Tran et al. |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,478 B2 | 7/2014 | Tuval et al. |
| 8,784,481 B2 | 7/2014 | Alkhatib et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,808,356 B2 | 8/2014 | Braido et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,845,718 B2 | 9/2014 | Tuval et al. |
| 8,870,948 B1 | 10/2014 | Erzberger et al. |
| 8,870,950 B2 | 10/2014 | Hacohen |
| 8,876,893 B2 | 11/2014 | Dwork et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,926,693 B2 | 1/2015 | Duffy et al. |
| 8,926,694 B2 | 1/2015 | Costello |
| 8,945,209 B2 | 2/2015 | Bonyuet et al. |
| 8,951,299 B2 | 2/2015 | Paul et al. |
| 8,961,593 B2 | 2/2015 | Bonhoeffer et al. |
| 8,961,595 B2 | 2/2015 | Alkhatib |
| 8,974,524 B2 | 3/2015 | Yeung et al. |
| 8,979,922 B2 | 3/2015 | Jayasinghe et al. |
| 8,986,372 B2 | 3/2015 | Murry, III et al. |
| 8,986,375 B2 | 3/2015 | Garde et al. |
| 8,992,608 B2 | 3/2015 | Haug et al. |
| 8,998,979 B2 | 4/2015 | Seguin et al. |
| 8,998,980 B2 | 4/2015 | Shipley et al. |
| 9,005,273 B2 | 4/2015 | Salahieh et al. |
| 9,011,521 B2 | 4/2015 | Haug et al. |
| 9,011,523 B2 | 4/2015 | Seguin |
| 9,011,524 B2 | 4/2015 | Eberhardt |
| 9,028,545 B2 | 5/2015 | Taylor |
| 9,034,032 B2 | 5/2015 | McLean et al. |
| 9,034,033 B2 | 5/2015 | McLean et al. |
| 9,039,757 B2 | 5/2015 | McLean et al. |
| 9,055,937 B2 | 6/2015 | Rowe et al. |
| 9,066,801 B2 | 6/2015 | Kovalsky et al. |
| 9,078,749 B2 | 7/2015 | Lutter et al. |
| 9,078,751 B2 | 7/2015 | Naor |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,186,249 B2 | 11/2015 | Rolando et al. |
| 9,220,594 B2 | 12/2015 | Braido et al. |
| 9,241,790 B2 | 1/2016 | Lane et al. |
| 9,248,014 B2 | 2/2016 | Lane et al. |
| 9,289,291 B2 | 3/2016 | Gorman, III et al. |
| 9,289,296 B2 | 3/2016 | Braido et al. |
| 9,331,328 B2 | 5/2016 | Eberhardt et al. |
| 9,339,382 B2 | 5/2016 | Tabor et al. |
| 9,351,831 B2 | 5/2016 | Braido et al. |
| 9,351,832 B2 | 5/2016 | Braido et al. |
| 9,364,321 B2 | 6/2016 | Alkhatib et al. |
| 9,572,662 B2 | 2/2017 | Morriss et al. |
| 9,579,196 B2 | 2/2017 | Morriss et al. |
| 9,629,718 B2 | 4/2017 | Gloss et al. |
| 9,763,780 B2 | 9/2017 | Morriss et al. |
| 9,775,705 B2 | 10/2017 | Ottma et al. |
| 9,788,945 B2 | 10/2017 | Ottma et al. |
| 9,839,511 B2 | 12/2017 | Ma et al. |
| 9,867,695 B2 | 1/2018 | Stacchino et al. |
| 9,889,002 B2 | 2/2018 | Bonhoeffer et al. |
| 10,492,908 B2 | 12/2019 | Hammer et al. |
| 2001/0007956 A1 | 7/2001 | Letac et al. |
| 2002/0016623 A1 | 2/2002 | Kula et al. |
| 2002/0032481 A1 | 3/2002 | Gabbay |
| 2002/0045929 A1 | 4/2002 | Diaz |
| 2002/0052644 A1 | 5/2002 | Shaolian et al. |
| 2003/0105517 A1 | 6/2003 | White et al. |
| 2003/0120333 A1 | 6/2003 | Ouriel et al. |
| 2003/0130729 A1 | 7/2003 | Paniagua et al. |
| 2003/0176914 A1 | 9/2003 | Rabkin et al. |
| 2003/0199971 A1 | 10/2003 | Tower et al. |
| 2003/0220683 A1 | 11/2003 | Minasian et al. |
| 2004/0117009 A1 | 6/2004 | Cali et al. |
| 2004/0133273 A1 | 7/2004 | Cox |
| 2004/0186561 A1 | 9/2004 | McGuckin et al. |
| 2004/0210304 A1 | 10/2004 | Seguin et al. |
| 2004/0210307 A1 | 10/2004 | Khairkhahan |
| 2004/0215325 A1 | 10/2004 | Penn et al. |
| 2004/0225353 A1 | 11/2004 | McGuckin et al. |
| 2004/0236411 A1 | 11/2004 | Sarao et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |

(56) References Cited

U.S. PATENT DOCUMENTS

| | | |
|---|---|---|
| 2009/0188964 A1 | 7/2009 | Orlov |
| 2009/0270972 A1 | 10/2009 | Lane |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0256723 A1 | 10/2010 | Murray |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142100 A1 | 5/2015 | Morriss et al. |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0327994 A1 | 11/2015 | Morriss et al. |
| 2015/0328001 A1 | 11/2015 | McLean et al. |
| 2015/0328002 A1 | 11/2015 | McLean et al. |
| 2015/0335424 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0135951 A1 | 5/2016 | Salahieh et al. |
| 2016/0143732 A1 | 5/2016 | Glimsdale |
| 2016/0213473 A1 | 7/2016 | Hacohen et al. |
| 2016/0235529 A1 | 8/2016 | Ma et al. |

FOREIGN PATENT DOCUMENTS

| | | |
|---|---|---|
| DE | 102006052564 B3 | 12/2007 |
| EP | 1255510 A1 | 11/2002 |
| EP | 1259194 A1 | 11/2002 |
| EP | 1281375 A2 | 2/2003 |
| EP | 1472996 A1 | 11/2004 |
| EP | 1734903 A1 | 12/2006 |
| EP | 2124826 A1 | 12/2009 |
| EP | 2237746 A2 | 10/2010 |
| EP | 2285317 A1 | 2/2011 |
| EP | 2308425 A1 | 4/2011 |
| EP | 2319458 A1 | 5/2011 |
| EP | 2496182 A1 | 9/2012 |
| EP | 2566416 A1 | 3/2013 |
| EP | 2745805 A1 | 6/2014 |
| EP | 2749254 A1 | 7/2014 |

(56) References Cited

FOREIGN PATENT DOCUMENTS

| | | | |
|---|---|---|---|
| EP | 2777617 A1 | 9/2014 | |
| EP | 2815723 A1 | 12/2014 | |
| EP | 2815725 A1 | 12/2014 | |
| EP | 2898858 A1 | 7/2015 | |
| EP | 2926766 B1 | 2/2016 | |
| EP | 2985006 A1 | 2/2016 | |
| GB | 126447 A | 5/1919 | |
| GB | 1315844 A | 5/1973 | |
| GB | 2398245 A | 8/2004 | |
| JP | 2002540889 A | 12/2002 | |
| JP | 2008541865 A | 11/2008 | |
| WO | 1997049355 A1 | 12/1997 | |
| WO | 0061034 A1 | 10/2000 | |
| WO | 03092554 A1 | 11/2003 | |
| WO | 2005011534 A1 | 2/2005 | |
| WO | 2006070372 A2 | 7/2006 | |
| WO | 2006085225 A1 | 8/2006 | |
| WO | 2006089236 A1 | 8/2006 | |
| WO | 2006127765 A1 | 11/2006 | |
| WO | 2007025028 A1 | 3/2007 | |
| WO | 2007058857 A2 | 5/2007 | |
| WO | 2007123658 A1 | 11/2007 | |
| WO | 2008013915 A2 | 1/2008 | |
| WO | 2008070797 A2 | 6/2008 | |
| WO | 2008103722 A2 | 8/2008 | |
| WO | 2008150529 A1 | 12/2008 | |
| WO | 2009026563 A2 | 2/2009 | |
| WO | 2009033469 A1 | 3/2009 | |
| WO | 2009045331 A1 | 4/2009 | |
| WO | 2009053497 A1 | 4/2009 | |
| WO | 2009094500 A1 | 7/2009 | |
| WO | 2009134701 A2 | 11/2009 | |
| WO | 2010008549 A1 | 1/2010 | |
| WO | 2010037141 A1 | 4/2010 | |
| WO | 2010040009 A1 | 4/2010 | |
| WO | 2010057262 A1 | 5/2010 | |
| WO | 2011025945 A1 | 3/2011 | |
| WO | 2011057087 A1 | 5/2011 | |
| WO | 2011111047 A2 | 9/2011 | |
| WO | 2011137531 A1 | 11/2011 | |
| WO | 2012177942 A2 | 12/2012 | |
| WO | 2013028387 A2 | 2/2013 | |
| WO | 2013075215 A1 | 5/2013 | |
| WO | 2013120181 A1 | 8/2013 | |
| WO | 2013175468 A2 | 11/2013 | |
| WO | 2013192305 A2 | 12/2013 | |
| WO | 2014018432 A2 | 1/2014 | |
| WO | 2014099655 A1 | 6/2014 | |
| WO | 2014110019 A1 | 7/2014 | |
| WO | 2014110171 A2 | 7/2014 | |
| WO | 2014121042 A1 | 8/2014 | |
| WO | 2014139545 A1 | 9/2014 | |
| WO | 2014145338 A1 | 9/2014 | |
| WO | 2014149865 A1 | 9/2014 | |
| WO | 2014163706 A1 | 10/2014 | |
| WO | 2014164364 A1 | 10/2014 | |
| WO | 2014194178 A1 | 12/2014 | |
| WO | 2014204807 A1 | 12/2014 | |
| WO | 2014205064 A1 | 12/2014 | |
| WO | 2014210124 A1 | 12/2014 | |
| WO | 2015077274 A1 | 5/2015 | |
| WO | 2015148241 A1 | 10/2015 | |
| WO | 2016016899 A1 | 2/2016 | |

OTHER PUBLICATIONS

Bavaria, Joseph E. M.D.: "CardiAQ Valve Technologies: Transcatheter Mitral Valve Implantation," Sep. 21, 2009.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.
Boudjemline, Younes, et al., "Steps Toward the Percutaneous Replacement of Atrioventricular Valves," JACC, vol. 16, No. 2, Jul. 19, 2005:360-5.
Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31, Applicant believes this may have been available as early as Dec. 2006.
Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.
Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.
Spillner, J. et al., "New Sutureless 'Atrial-Mitral-Valve Prosthesis' for Minimally Invasive Mitral Valve Therapy," Textile Research Journal, 2010, in 7 pages, Applicant believes this may have been available as early as Aug. 9, 2010.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "Double-Crowned Valved Stents for Off-Pump Mitral Valve Replacement," European Journal of Cardio-thoracic Surgery 28 (2005) 194-199, Applicant believes this may have been available as early as Aug. 2005.
Pluth, James R., M.D., et al., "Aortic and Mitral Valve Replacement with Cloth-Covered Braunwald-Cutter Prosthesis, a Three-Year Follow-up," The Annals of Thoracic Surgery, vol. 20, No. 3, Sep. 1975, pp. 239-248.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.
Sondergaard, Lars, et al., "Transcatheter Mitral Valve Implantation: CardiAQ™," Applicant believes this may have been presented at TCT 2013.
Sondergaard, Lars, et al., "Transcatheter Mitral Valve Implantation: CardiAQ™," Applicant believes this may have been presented at EuroPCR 2013.
Sondergaard, Lars, "CardiAQ TMVR FIH—Generation 2," Applicants believe this may have been presented in 2014 at the TVT symposium.
CardiAQ Valve Technologies, "Innovations in Heart Valve Therapy," In3 San Francisco, Jun. 18, 2008, PowerPoint presentation in 19 slides.
Ratz, J. Brent, "LSI EMT Spotlight," May 15, 2009.

(56) References Cited

OTHER PUBLICATIONS

Raiz, J. Brent, "In3 Company Overview," Jun. 24, 2009.
"Company Overview," at TVT on Jun. 25, 2009.
Ruiz, Carlos E., "Overview of Novel Transcatheter Valve Technologies," Applicant believes this may have been presented on May 27, 2010 at EuroPCR.
"Update," Applicant believes this may have been presented on Jun. 6, 2010 at TVT.
Mack, Michael, M.D., "Antegrade Transcatheter Mitral valve Implantation: A Short-term Experience in Swine Model," Applicant believes this may have been presented on May 2011 at TVT.
Mack, Michael, M.D., "Antegrade Transcatheter Mitral valve Implantation: On-Going Experience in Swine Model," Applicant believes this may have been presented on Nov. 2011 at TCT.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.
Quadri, Arshad M.D., "Transcatheter Mitral Valve Implantation (TMVI) (an Acute in Vivo Study)," Applicant believes this may have been presented on Sep. 22, 2010 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Horvath et al.: "Transapical Aortic Valve Replacement under Real-time Magnetic Resonance Imaging Guidance: Experimental Results with Balloon—Expandable and Self-Expanding Stents," http://www.ncbi.nlm.nih.gov/pmc/articles/PMC3038190/. Jun. 2011.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Grube, E. et al, "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.

Feldman, Ted, MD. "Prospects for Percutaneous Valve Therapies," Circulation 2007;116:2866-2877. Applicant believes that this may be available as early as Dec. 11, 2007.
Backer, Ole De, MD, et al., "Percutaneous Transcatheter Mitral Valve Replacement—an Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
"CardiAQTM Valve Technologies reports Successful First-in-Human Trans-Apical implantation of its Second Generation Transcatheter Mitral Valve," CardiAQ Valve Technologies Press Release, May 20, 2014.
Dave Fornell, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
The Journal of the American College of Cardiology, "Transapical Mitral Implantation of the Tiara Bioprosthesis Pre-Cinical Results," Feb. 2014, <http://interventions.onlinejacc.org/article.aspx?articleid=1831234>.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Bavaria, Joseph E. M.D. et al.: "Transcatheter Mitral Valve Implantation: The Future Gold Standard for MR?," Applicant requests the Examiner to consider this reference to be prior art as of Dec. 2010.

\* cited by examiner

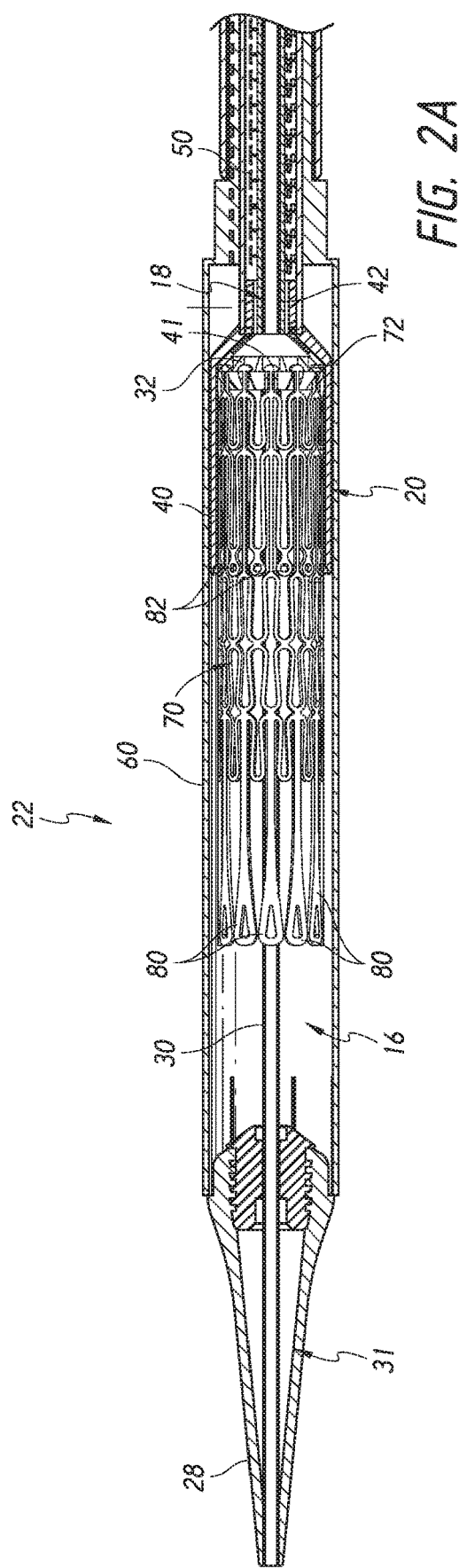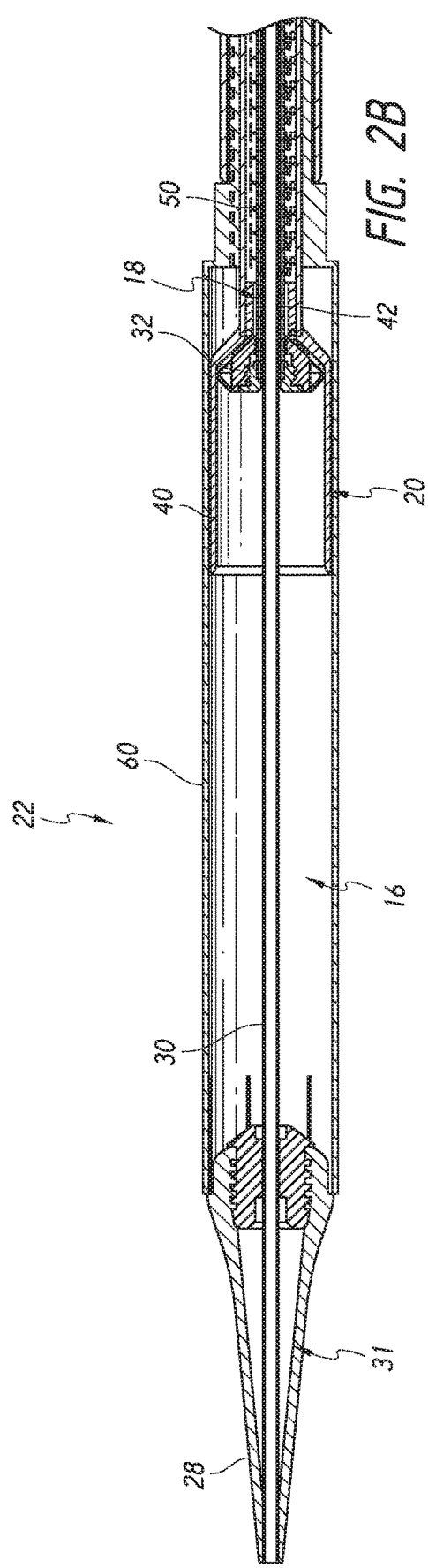

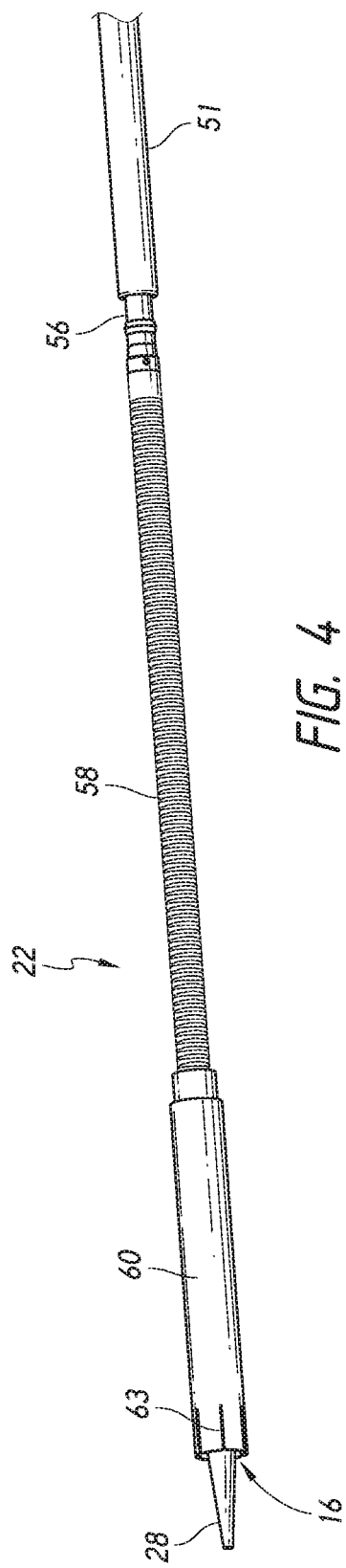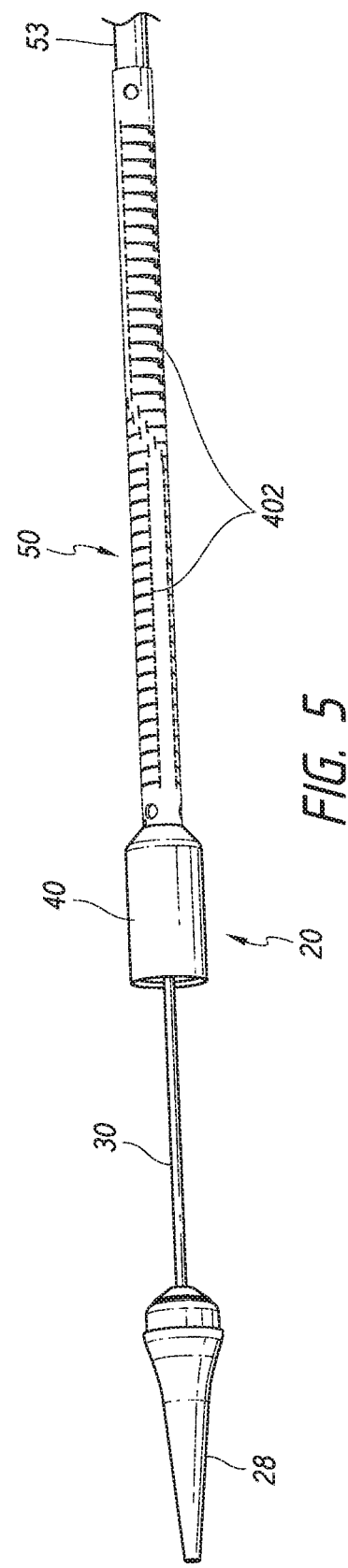
FIG. 4
FIG. 5

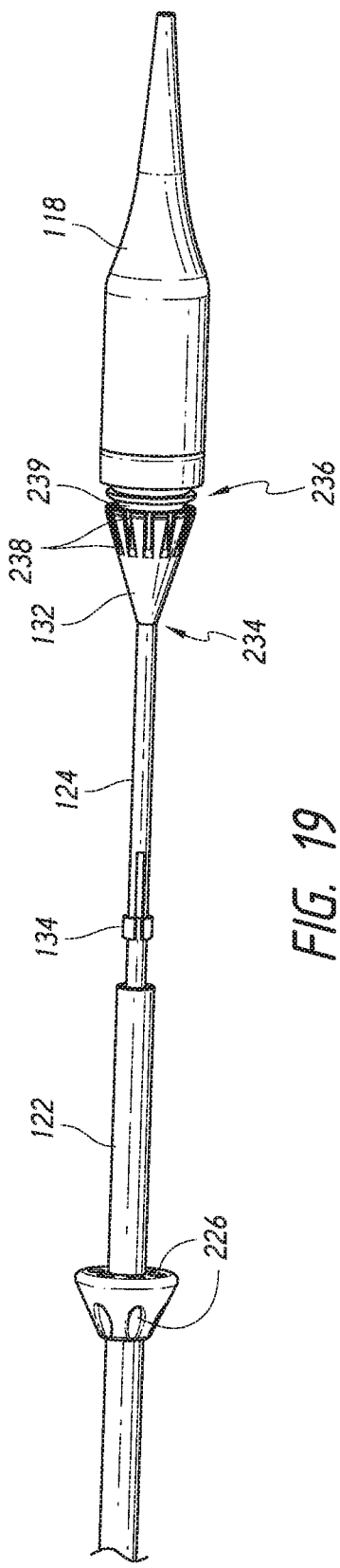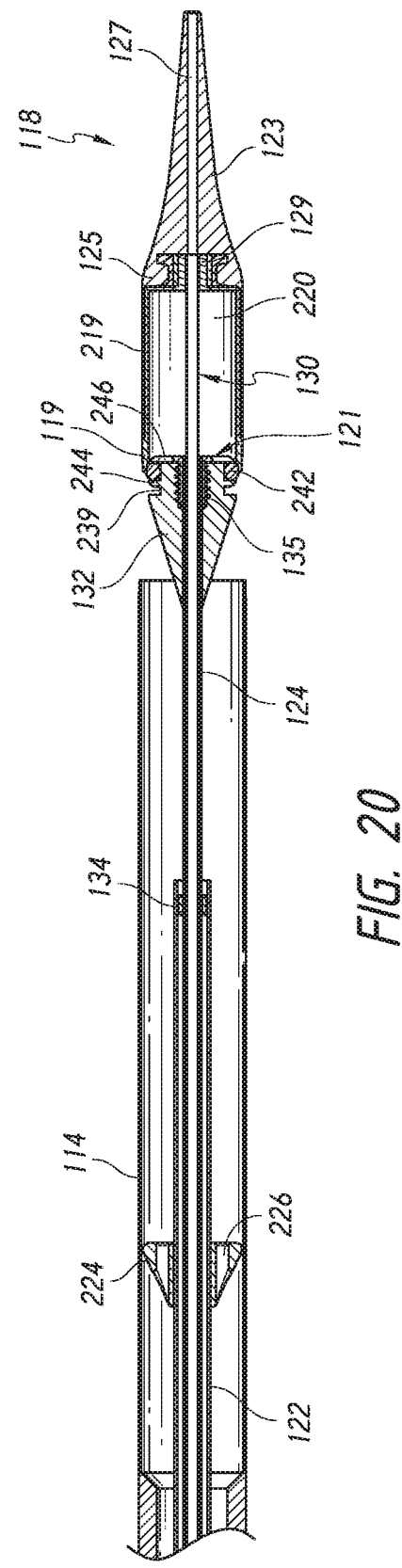

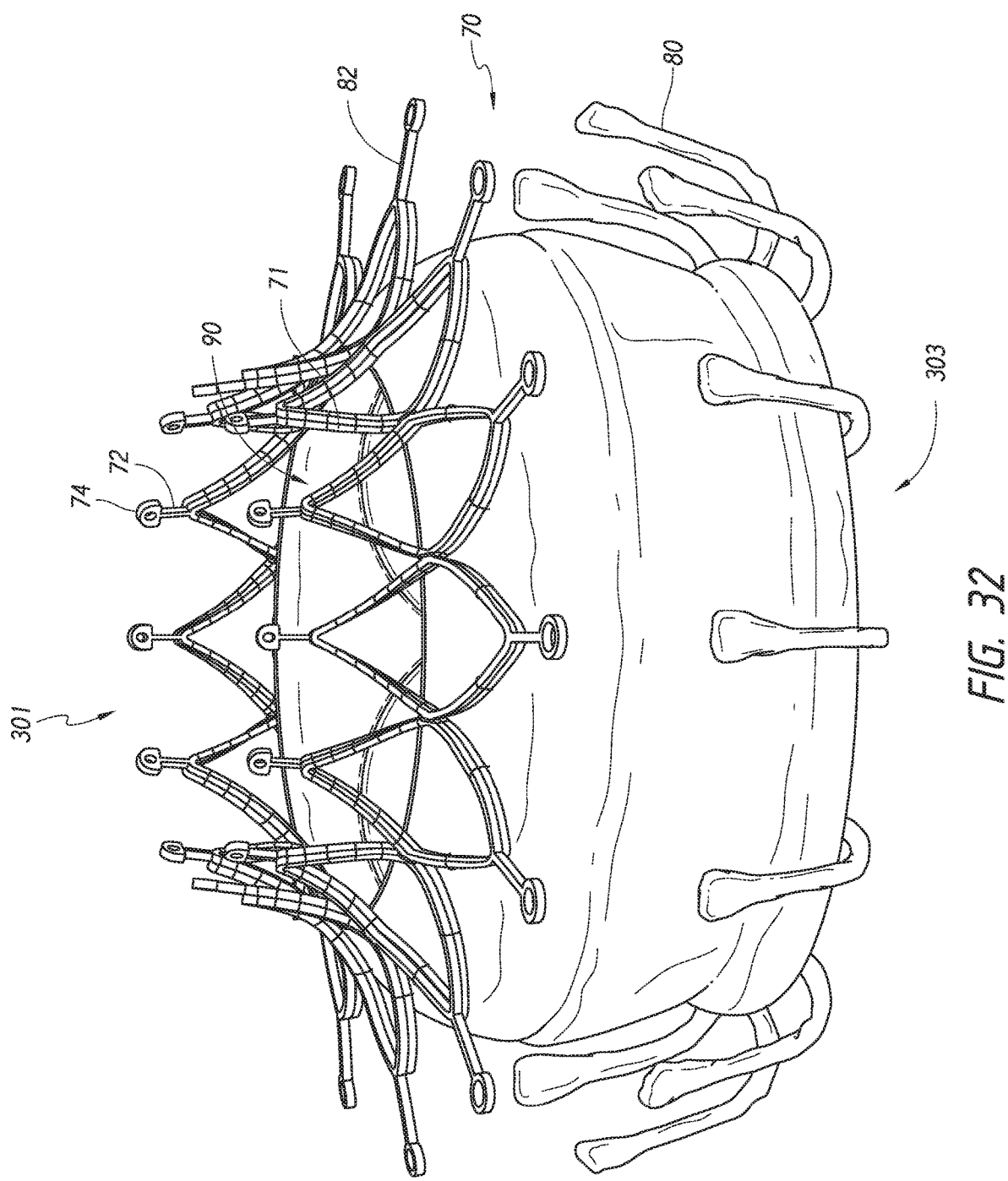

SUPRA AND SUB-ANNULAR MITRAL VALVE DELIVERY SYSTEM

INCORPORATION BY REFERENCE TO ANY PRIORITY APPLICATIONS

This Application claims the benefit of U.S. Provisional Application No. 62/416,417, filed Nov. 2, 2016, titled "SUPRA AND SUB-ANNULAR MITRAL VALVE DELIVERY SYSTEM," the entirety of which is incorporated herein by reference.

BACKGROUND

Field

Certain embodiments disclosed herein relate generally to prostheses for implantation within a lumen or body cavity, delivery systems for a prosthesis, and methodologies for delivering the prosthesis. In particular, the prostheses and delivery systems relate in some embodiments to replacement heart valves, such as replacement mitral heart valves.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner.

Delivering a prosthesis to a desired location in the human body, for example delivering a replacement heart valve to the mitral valve, can also be challenging. Obtaining access to perform procedures in the heart or in other anatomical locations may require delivery of devices percutaneously through tortuous vasculature or through open or semi-open surgical procedures. The ability to control the deployment of the prosthesis at the desired location can also be challenging.

SUMMARY

Embodiments of the present disclosure are directed to a prosthesis, such as but not limited to a replacement heart valve. Further embodiments are directed to delivery systems, devices and/or methods of use to deliver and/or controllably deploy a prosthesis, such as but not limited to a replacement heart valve, to a desired location within the body. In some embodiments, a replacement heart valve and methods for delivering a replacement heart valve to a native heart valve, such as a mitral valve, are provided.

The present disclosure includes, but is not limited to, the following numbered embodiments.

Disclosed herein are embodiments of a method for delivering a replacement mitral valve with a delivery system, the method comprising delivering distal end of the delivery system containing the replacement mitral valve into a left atrium of a heart, wherein the replacement mitral valve is in a radially compressed condition in the delivery system, releasing a first set of anchors of the replacement mitral valve from the radially compressed condition in the left atrium or in line with a native mitral valve annulus, wherein releasing the first set of anchors causes the anchors to flip positions from the radially compressed condition, passing the first set of anchors through the native mitral valve annulus, and fully releasing the replacement mitral valve prosthesis from the delivery system.

Further disclosed herein are embodiments of a method for delivering a replacement mitral valve with a delivery system, the method comprising delivering a distal end of the delivery system containing the replacement mitral valve into a left atrium of a heart, wherein the replacement mitral valve is in a radially compressed condition in the delivery system, releasing a first set of anchors of the replacement mitral valve from the radially compressed condition in the left atrium or in line with a native mitral valve annulus, wherein releasing the first set of anchors causes the anchors to flip positions from the radially compressed condition, translating the first set of anchors into a left ventricle of the heart, and fully releasing the replacement mitral valve prosthesis from the delivery system into an expanded condition.

In some embodiments, the replacement mitral valve can further comprise a second set of anchors spaced from the first set of anchors. In some embodiments, the method can further comprise releasing the second set of anchors in the left atrium. In some embodiments, the method can further comprise translating the replacement mitral valve towards the left atrium after passing the first set of anchors through the native mitral valve annulus.

In some embodiments, translating the replacement mitral towards the left atrium can capture a native mitral valve leaflet with the first set of anchors. In some embodiments, the first set of anchors can flip from extending proximally to extending distally or flip from extending distally to extending proximally upon releasing the first set of anchors. In some embodiments, the first set of anchors can pass between chordae of the left ventricle.

In some embodiments, the replacement mitral valve can comprise a single frame. In some embodiments, delivering the distal end of the delivery system can comprise delivering in a transapical delivery approach. In some embodiments, delivering the distal end of the delivery system can comprise delivering in a transseptal delivery approach.

In some embodiments, the method can further comprise rotating the delivery system after the releasing the first set of anchors. In some embodiments, the fully releasing the replacement mitral valve can comprise loosening a tether wrapped at least partially around the replacement mitral valve. In some embodiments, the delivery system can comprise a plurality of sleeves which can slide with respect to one another in order to release the replacement mitral valve.

In some embodiments, the first set of anchors can be released in line with the native mitral valve annulus. In some embodiments, the first set of anchors can be released in the left atrium. In some embodiments, translating the first set of anchors into the left ventricle of the heart can comprise passing the first set of anchors through the native mitral valve annulus.

BRIEF DESCRIPTION OF THE DRAWINGS

FIG. 2A shows a cross-sectional view of the distal end of the delivery system of FIG. 1 loaded with the valve prosthesis of FIG. 3.

FIG. 2B shows a cross-sectional view of the distal end of the delivery system of FIG. 1 without the valve prosthesis of FIG. 3.

FIG. 4 shows a perspective view of the distal end of the delivery system of FIG. 1.

FIG. 5 show components of the delivery system of FIG. 4 with the outer sheath assembly moved proximally and out of view.

FIG. 19 illustrates a distal end of an embodiment of the delivery device.

FIG. 20 illustrates a cross section of an embodiment of the delivery device.

FIG. 32 shows a side view of an embodiment of a valve prosthesis that may be delivered using the delivery systems described herein.

DETAILED DESCRIPTION

The present specification and drawings provide aspects and features of the disclosure in the context of several embodiments of replacement heart valves, delivery systems, and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within an artery, a vein, or other body cavities or locations. In addition, particular features of a valve, delivery system, etc. should not be taken as limiting, and features of any one embodiment discussed herein can be combined with features of other embodiments as desired and when appropriate. While certain of the embodiments described herein are described in connection with a transfemoral delivery approach, it should be understood that these embodiments can be used for other delivery approaches such as, for example, transapical approaches. Moreover, it should be understood that certain of the features described in connection with some embodiments can be incorporated with other embodiments, including those which are described in connection with different delivery approaches.

Transseptal Delivery System

Figure 1:
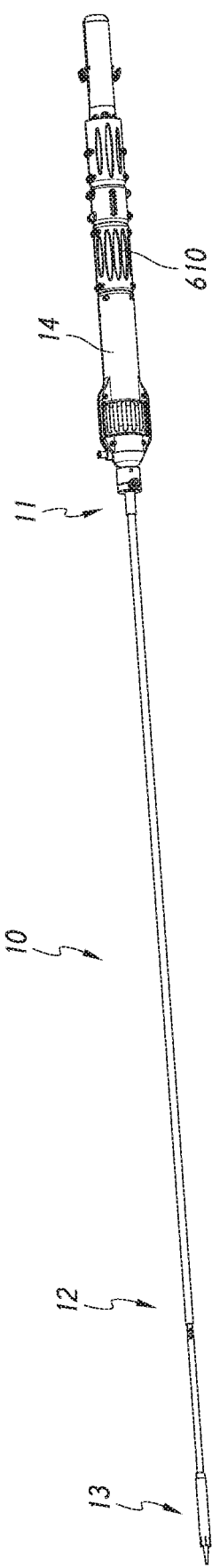
FIG. 1 shows an embodiment of a delivery system.

With reference to FIG. 1, an embodiment of a delivery device or system 10 is shown. The delivery system can be used deploy a prosthesis, such as a replacement heart valve, within the body. Replacement heart valves can be delivered to a patient's heart mitral valve annulus or other heart valve location in various ways, such as by open surgery, minimally-invasive surgery, and percutaneous or transcatheter delivery through the patient's vasculature. Example transfemoral approaches may be found in U.S. Pat. Pub. No. 2015/0238315, filed Feb. 20, 2015, the entirety of which is hereby incorporated by reference in its entirety. While the delivery system 10 is described in connection with a percutaneous delivery approach, and more specifically a transfemoral delivery approach, it should be understood that features of delivery system 10 can be applied to other delivery system, including delivery systems for a transapical delivery approach. Further examples of devices, systems and methods are described in U.S. Patent Publication No. 2016/0317301, and U.S. Provisional Patent Application No. 62/629394, filed Jul. 6, 2017, the entirety of each of which is incorporated by reference. In particular, delivery system 10 as described herein can have components, features, and/or functionality similar to those described with respect to delivery systems, devices and methods described in at least paragraphs [0006]-[0037] and [0078]-[0170] of U.S. Provisional Application No. 62/163932, filed May 19, 2015, including the description relating to FIGS. 1-40B, and all of these descriptions are expressly incorporated by reference herein. Moreover, delivery system 10 as described herein can have components, features, and/or functionality similar to those described with respect to the systems, devices and methods described with respect to paragraphs [0171]-[0197] of U.S. Provisional Application No. 62/163932, filed May 19, 2015, including the description relating to FIGS. A1-A5, B1-B6, C1-C2 and 41A-42B, and U.S. Provisional Application No. 62/210,165, filed Aug. 26, 2015, and all of these descriptions are expressly incorporated by reference herein.

The delivery system 10 can be used to deploy a prosthesis, such as a replacement heart valve as described elsewhere in this specification, within the body. The delivery system 10 can receive and/or cover portions of the prosthesis such as a first end 301 and second end 303 of the prosthesis 70 illustrated in FIG. 3 below. For example, the delivery system 10 may be used to deliver an expandable implant or prosthesis 70, where the prosthesis 70 includes the first end 301 and the second end 303, and wherein the second 303 end is configured to be deployed or expanded before the first end 301.

The delivery system 10 can be relatively flexible. In some embodiments, the delivery system 10 is particularly suitable for delivering a replacement heart valve to a mitral valve location through a transseptal approach (e.g., between the right atrium and left atrium via a transseptal puncture).

As shown in FIG. 1, the delivery system 10 can include an elongate shaft assembly 12 comprising a proximal end 11 and a distal end 13, wherein a handle 14 is coupled to the proximal end of the assembly 12. The elongate shaft assembly 12 can be used to hold the prosthesis for advancement of the same through the vasculature to a treatment location. The delivery system 10 can further comprise a relatively rigid live-on sheath 51 surrounding the elongate shaft assembly 12 that can prevent unwanted motion of the elongate shaft assembly 12. The elongate shaft assembly 12 can include an implant retention area 16 (shown in FIGS. 2A-B with FIG. 2A showing the prosthesis 70 and FIG. 2B with the prosthesis 70 removed) at its distal end that can be used for this purpose. In some embodiments, the elongate shaft assembly 12 can hold an expandable prosthesis in a compressed state at implant retention area 16 for advancement of the prosthesis within the body. The elongate shaft assembly 12 may then be used to allow controlled expansion of the prosthesis at the treatment location. The implant retention area 16 is shown in FIGS. 2A-B at the distal end of the delivery system, but may also be at other locations. In some embodiments, the prosthesis 70 may be rotated in the implant retention area 16, such as through the rotation of the inner assembly 18 discussed herein.

As shown in cross-sectional view of FIGS. 2A-B, the elongate shaft assembly 12 can include one or more subassemblies such as an inner assembly 18, a mid-shaft assembly 20, an outer sheath assembly 22, and nose cone assembly 31 as will be described in more detail below.

As shown, the outer sheath assembly 22 can form a radially outer covering, or sheath, to surround an implant retention area 16. Moving radially inward, the mid shaft assembly 20 can be composed of a mid-shaft 50 with its distal end attached to outer retention member or outer retention ring 40. Moving further inwards, the inner assembly 18 can be composed of an inner retention shaft 42 and an inner retention member 32. Further, the most radially-inward assembly is the nose cone assembly 31 which includes the nose cone shaft 30 having its distal end connected to the nose cone 28.

The elongate shaft assembly 12, and more specifically the nose cone assembly 31, inner assembly 18, mid shaft assembly 20, and outer sheath assembly 22, can be configured to deliver a prosthesis 70 positioned within the implant retention area 16 (shown in FIG. 2A) to a treatment location. One or more of the subassemblies can then be moved to allow the prosthesis 70 to be released at the treatment location. For example, one or more of the subassemblies may be movable with respect to one or more of the other subassemblies. The handle 14 can include various control mechanisms that can be used to control the movement of the various subassemblies as will also be described in more detail below. In this way, the prosthesis 70 can be controllably loaded onto the delivery system 10 and then later deployed within the body.

Figure 3:
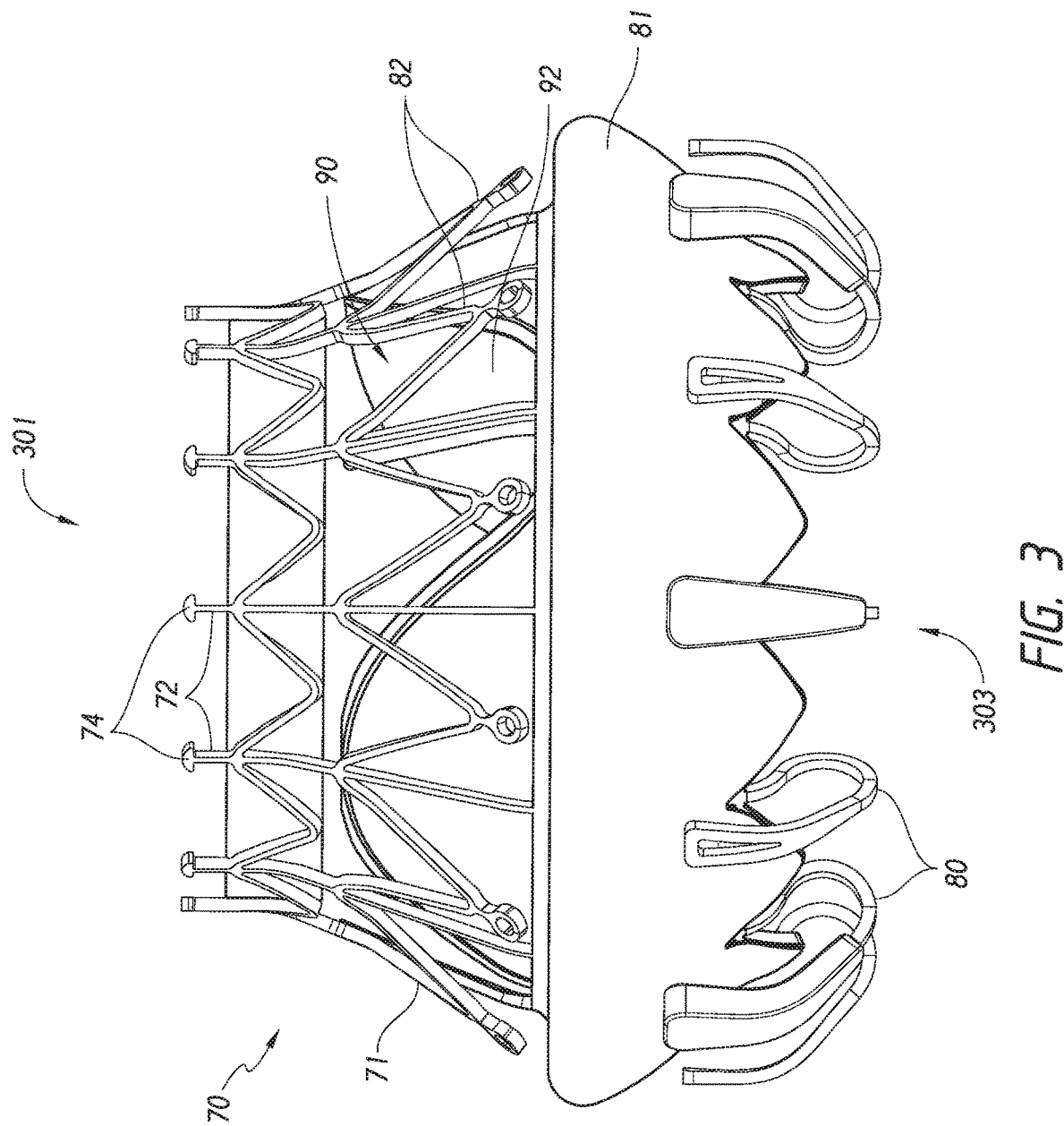
FIG. 3 shows a side view of an embodiment of a valve prosthesis that may be delivered using the delivery systems described herein.

FIG. 2A further shows an example of the prosthesis 70 that can be inserted into the delivery system 10, specifically into the implant retention area 16. For ease of understanding, in FIG. 2A, the prosthesis is shown with only the bare metal frame illustrated. The implant or prosthesis 70 can take any number of different forms. A particular example of a frame 71 for a prosthesis is shown in FIG. 3, though it will be understood that other designs can also be used. The prosthesis 70 can include one or more sets of anchors, such as distal (or ventricular) anchors 80 extending proximally when the prosthesis frame 71 is in an expanded configuration and proximal (or atrial) anchors 82 extending distally when the prosthesis frame 71 is in an expanded configuration. The prosthesis can further include struts 72 which may end in mushroom-shaped tabs 74 at the first end 301 as well as a flap 81 surrounding the frame near the second end 303. Further discussion on the annular flap 81 can be found in U.S. Publication No. 2015/0328000, published Nov. 19, 2015, hereby incorporated by reference in its entirety.

The prosthesis 70 can include a valve body or assembly 90. The valve assembly 90 can function as a one-way valve to allow blood flow in a first direction through the valve assembly 90 and inhibit blood flow in a second direction through the valve assembly 90. For example, in embodiments where the first end 301 is a proximal end and the second end 303 is a distal end, the valve assembly 90 can allow blood flow in a proximal-to-distal direction and inhibit blood flow in a distal-to-proximal direction. The valve assembly 90 preferably includes a plurality of valve leaflets 92, for example three leaflets 92, which are joined at commissures.

In some embodiments, the valve assembly 76 can include one or more intermediate components (not shown) which can be positioned between a portion of, or the entirety of, the leaflets 92 and the frame 71 such that at least a portion of the leaflets 92 are coupled to the frame 71 via the intermediate component. In this manner, a portion of, or the entirety of, the portion of the valve leaflets 92 at the commissures and/or an arcuate edge of the valve leaflets 92 are not directly coupled or attached to the frame 71 and are indirectly coupled or "float" within the frame 71. In some embodiments, the valve body 71 can include a liner (not shown). Further discussion on intermediate components and liners can be found in U.S. application Ser. No. 15/653,390, filed Jul. 18, 2017, and U.S. application Ser. No. 15/687,184, filed Aug. 25, 2017, the entirety of each of which is hereby incorporated by reference and made part of this specification.

Figure 33:
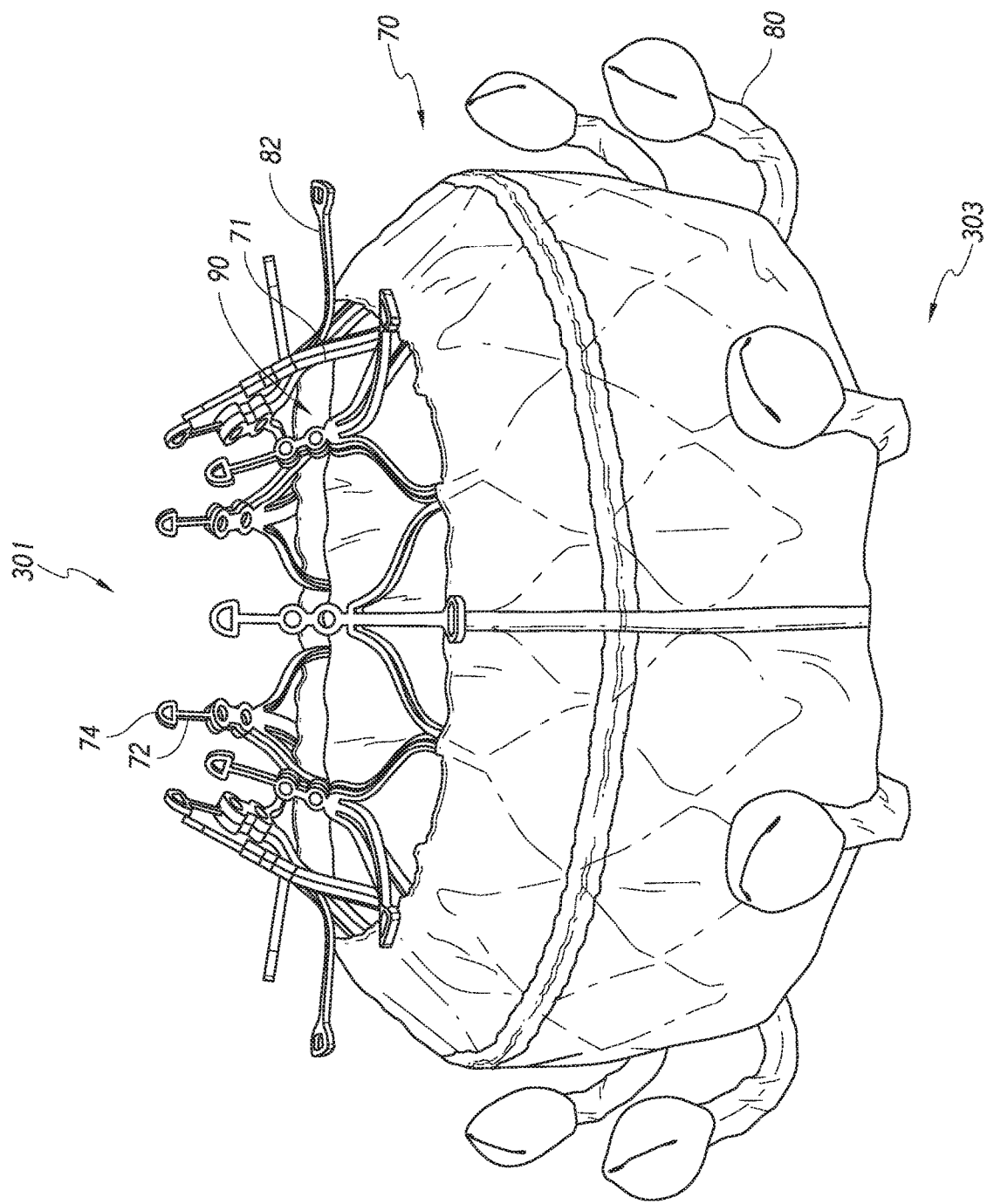
FIG. 33 shows a side view of an embodiment of a valve prosthesis that may be delivered using the delivery systems described herein.
Figure 34:
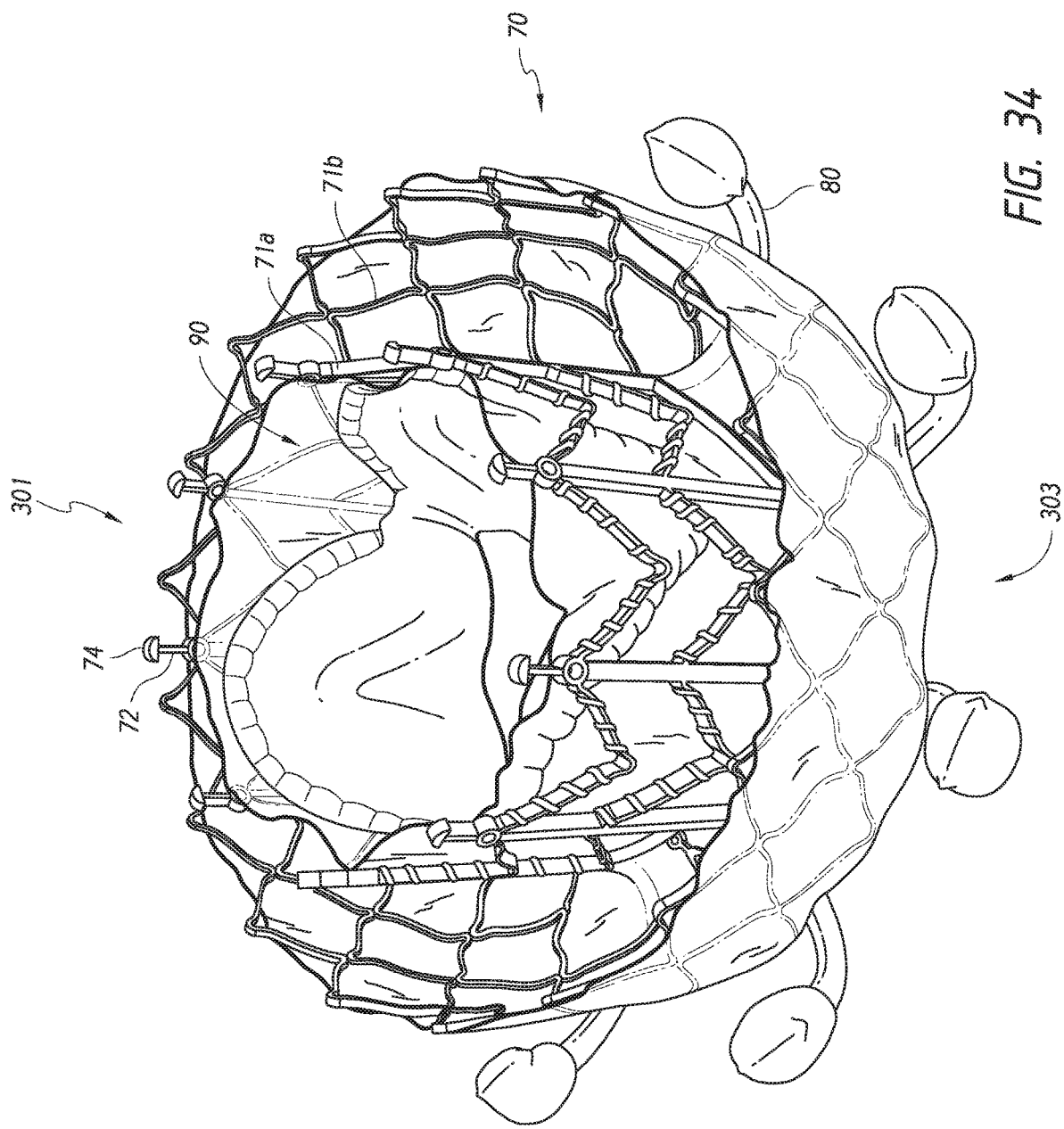
FIG. 34 shows a side view of an embodiment of a valve prosthesis that may be delivered using the delivery systems described herein.

FIGS. 32-34 illustrate alternative embodiment of a prosthesis 70 that can used with the disclosed delivery system 10 and methodology discussed herein. These embodiments can have similar or the same features to the prostheses discussed herein. In some embodiments, the prosthesis may be a single frame prosthesis. In some embodiments, the prosthesis may be a dual frame prosthesis. For example, as shown in FIG.

34A, a prosthesis 70 can include an inner frame 71a and an outer frame 71b. In some embodiments, the outer frame 71b can be conformable for placement in the native mitral valve annulus and the inner frame 71a can support the valve assembly 90. Further details on these specific embodiments can be found in U.S. patent application Ser. No. 15/653,390, filed Jul. 18, 2017 and Ser. No. 15/687,184, filed Aug. 25, 2017, which have been incorporated by reference in their entirety.

Additional details and example designs for a prosthesis are described in U.S. Pat. Nos. 8,403,983, 8,414,644, 8,652,203 and U.S. Patent Publication Nos. 2011/0313515, 2012/0215303, 2014/0277390, 2014/0277422, 2014/0277427, and 2016/0317301 the entirety of these patents and publications are hereby incorporated by reference and made a part of this specification. Further details and embodiments of a replacement heart valve or prosthesis and its method of implantation are described in U.S. patent application Ser. No. 14/716,507, filed May 19, 2015 the entirety of which is hereby incorporated by reference and made a part of this specification.

As will be discussed below, the inner retention member 32, the outer retention ring 40 and the outer sheath assembly 22 can cooperate to hold the prosthesis 70 in a compacted configuration. The inner retention member 32 is shown engaging struts 72 at the proximal end of the prosthesis 70. For example, slots located between radially extending teeth on the inner retention member 32 can receive and engage the struts 72 which may end in mushroom-shaped tabs 74 on the proximal end of the prosthesis 70. The outer retention ring 40 can be positioned over the inner retention member 32 so that the first end 301 of the prosthesis 70 is trapped therebetween, securely attaching it to the delivery system 10.

As shown in FIG. 2A, the ventricular anchors 80 can be located in a delivered configuration where the ventricular anchors 80 point generally distally (as illustrated, axially away from the main body of the prosthesis frame and away from the handle of the delivery system). The ventricular anchors 80 can be restrained in this delivered configuration by the outer sheath assembly 22. Accordingly, when the outer sheath 22 is withdrawn proximally, the ventricular anchors 80 can flip positions to a deployed configuration (e.g., pointing generally proximally). FIG. 2A also shows the atrial anchors 82 extending distally in their delivered configuration within the outer sheath assembly 22 and within the outer retention ring 40. In other embodiments, the ventricular anchors 80 can be held to point generally proximally in the delivered configuration and compressed against the body of the prosthesis frame.

The delivery system 10 may be provided to users with a prosthesis 70 preinstalled. In other embodiments, the prosthesis 70 can be loaded onto the delivery system shortly before use, such as by a physician or nurse.

Figure 6:
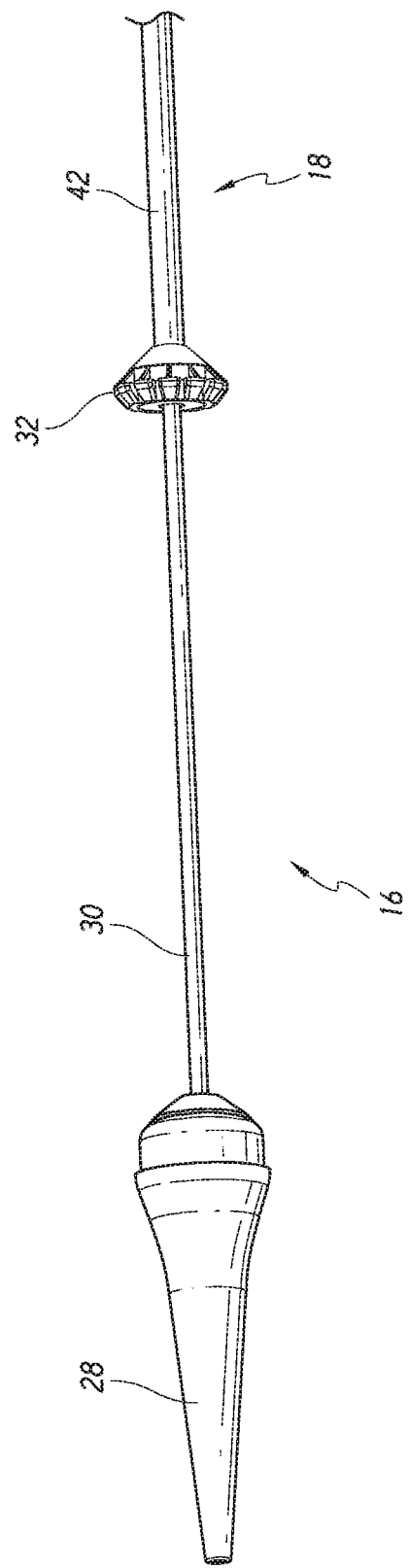
FIG. 6 show components of the delivery system of FIG. 5 with the mid shaft assembly moved proximally and out of view.

FIGS. 4-6 illustrate further views of delivery system 10 with different assemblies translated proximally and described in detail.

The outer sheath assembly 22 will now be described, which is shown in FIG. 4. Specifically, FIG. 4 shows an outer sheath assembly 22 in its distal most position relative to nose cone 28. Further, as shown, a live-on sheath 51 can be used to cover the outer sheath assembly 22 and provide structural support during bending, though its use is optional. The outer sheath assembly 22 is disposed so as to be slidable over the inner assembly 18, the mid shaft assembly 20, and the nose cone assembly 31. Like the nose cone assembly 31, inner assembly 18 and the mid shaft assembly 20, the outer sheath assembly 22 can be a single piece tube or multiple pieces connected together to provide different characteristics along different sections of the tube. As has been mentioned, in some embodiments it can be desirable, and/or needful, for the delivery system 10 to have greater flexibility at the distal end of the device, where flexibility is not as necessary for the proximal end. The illustrated outer sheath assembly 22 has a first segment 56, a second segment 58, and a third segment 60, where the first segment 56 is proximal to the second segment 58, and the second segment 58 is proximal to the third segment 60. The third segment 60 of the outer sheath is shown in contact with the proximal end of the nose cone 28. In this position, a prosthesis 70 can be held within the outer shaft assembly 22 for advancement of the same through the vasculature to a treatment location. The first segment 56 may be a tube and is preferably formed plastic, but could also be a metal hypotube or other material.

The second segment 58 can be a metal hypotube which in some embodiments may be cut or have slots. The tube 58 can be covered or encapsulated with a layer of ePTFE, PTFE, or other material so that the outer surface of the outer sheath assembly is generally smooth. The covered second segment 58 is shown in FIG. 4. The third segment 60 can be a tube formed of a plastic or metal material. In a preferred embodiment, the third segment is formed of ePTFE or PTFE. In some embodiments this sheathing material can be relatively thick to prevent tearing and to help maintain a self-expanding implant in a compacted configuration. In some embodiments the material of the third segment 60 is the same material as the coating on the cut hypotube 1058.

In some embodiments the third segment 60 can include one or more wings or tabs 63, shown in FIG. 4, extending distally from a distal end of the third segment 60. The tabs 63 can be configured to bend, curve, or fold radially outward from the third segment 60. The one or more tabs 63 can facilitate loading of a replacement valve within the third segment 60 when the replacement valve is initially loaded into the delivery system 10. In some embodiments, the one or more tabs 63 can be removed prior to use within a patient, such as shown in U.S. application Ser. No. 15/141,684 filed Apr. 28, 2016. The one or more tabs 63 can be formed by cutting the third segment 60 via methods including, but not limited to, laser cutting.

FIG. 5 illustrates the system 10 with the outer sheath assembly 22 removed (e.g., by pulling the outer sheath assembly 22 proximally), thus partially exposing the mid shaft assembly 20 including a portion of or all of a prosthesis (not shown) in the implant retention area 16. Like the nose cone assembly 31, inner assembly 18, and outer sheath assembly 22, the mid shaft assembly 20 can be a single piece tube or multiple pieces connected together to provide different characteristics along different sections of the tube. As has been mentioned, in some embodiments it can be desirable, and/or needful, for the delivery system 10 to have greater flexibility at the distal end of the device, where flexibility is not as necessary for the proximal end. The illustrated mid shaft assembly 20 has a first segment 53, a second segment or mid shaft 50 distal to the first segment, and a third segment 40 distal the mid-shaft 50 being the outer retention ring 40. The first segment can extend distally away from the handle and be connected to the second segment or mid shaft 50 at the distal end of the first segment. As shown in FIG. 5, the distal end of the second segment 50 can attach to the outer retention ring 40 (e.g., third segment). Each of the segments can be a tube, for example a metal or polymer tube, such as described with respect to the outer sheath assembly 22.

Through the use of the handle 14, the mid shaft assembly 20 can translate or slide over the inner assembly 18, which thereby causes the outer retention ring 40 to slide over the inner assembly 18 and encircle the inner retention member 32 described below. As shown in FIG. 2A, the outer retention ring 40 encircles a portion of the prosthesis 70, in particular the proximal portion, thus preventing the prosthesis 70 from expanding. The outer retention ring 40 can also circumferentially surround the inner retention member 32. Further, the mid shaft assembly 20 can be translated proximally with respect to the inner assembly 18 into the proximally-retracted outer sheath assembly 22, thus exposing a proximal portion of the prosthesis 70 held within the outer retention ring 40. A taper 61 may be provided at the proximal end of the outer retention ring 40 to allow it to more easily slide into the outer sheath assembly 22. In this way the outer retention ring 40 can be used to help secure a prosthesis to or release it from the delivery system 10. The outer retention ring 40 can have a cylindrical or elongate tubular shape.

Further, as shown in FIG. 2A, the outer retention ring 40 can cover a substantial length of the prosthesis 70. For example, the outer retention ring 40 can cover over ⅛, ¼, ⅓, or ½ of the prosthesis 70. In addition, the outer retention ring 40 can cover a substantial length of the atrial anchors 82. For example, the outer retention ring 40 can cover over 75%, over 80%, over 85%, or over 90% of the atrial anchors 82. The outer retention ring 40 can be about 15, 17, 17, 18, 19, or 20 mm in length or a range between those lengths. In some embodiments, the outer retention ring 40 can be between about 10 and about 30 mm in length.

FIG. 6 shows approximately the same view as FIG. 5, but with the mid shaft assembly 20, including the outer retention ring 40 and mid shaft 50, removed, thereby partially exposing the inner assembly 18 (including the inner retention member 32 attached to inner retention shaft 42) and nose cone assembly 31 (including the nose cone shaft 30 attached to the nose cone 28).

As mentioned the inner assembly 18 can be composed of the inner retention shaft 42 with the inner retention member 32 attached to the distal end of the inner retention shaft 42. Similar to the assemblies above, the inner retention shaft 42 can comprise a tube, such as a hypodermic tube or hypotube (not shown). The tube can be made from one of any number of different materials including nitinol, stainless steel, and medical grade plastics. The tube can be a single piece tube or multiple pieces connected together. Using a tube made of multiple pieces can allow the tube to provide different characteristics along different sections of the tube, such as rigidity and flexibility.

In some embodiments a first segment (now shown) of the inner assembly 18 can be made of a hypotube can extend along a majority of the length of the inner assembly 18. For example, metal hypotube extends from within the handle 16 at the proximal end towards the distal end up until a second segment (or inner retention shaft) 42 of the inner assembly 18 before the implant retention area 16. The hypotube can provide column strength (pushability) to the inner assembly. Further, the handle 16 can allow for rotation of the second segment 42, which can allow for rotation of the prosthesis 70. A second segment 42 of the inner assembly 18 can be made of a more flexible material. For example, the second segment 42 can comprise a wire such as a multi-stranded wire, wire rope, or wire coil. The wire can surround a more flexible tube, such as a plastic tube, or it may be formed as a tube without any additional inner materials or core. Thus, in some embodiments, the wire can be a hollow core wire rope. The wire can provide the inner assembly 18 with strength, but it can also provide more flexibility to allow for navigating the tight curves of the vasculature, such as within the heart.

The inner assembly 18 can also include a prosthesis retention mechanism such as an inner retention member 32 at a distal end of the second segment 42 that can be used to engage with the prosthesis, as discussed with respect to FIG. 2A. For example, the inner retention member 32 may be a ring and can include a plurality of slots configured to engage with struts 72 on the prosthesis 70. The inner retention member 32 can also be considered to be part of the implant retention area 16, and may be at the proximal end of the implant retention area 16. With struts or other parts of a prosthesis 70 engaged with the inner retention member 32, an outer retention member such as outer retention ring 40 can cover both the prosthesis and the inner retention member 32 to secure the prosthesis on the delivery system 10.

Further, as shown in FIG. 6, the nose cone assembly 31 may be an elongate member, and in some embodiments, may have a nose cone 28 on its distal end. The nose cone 28 can be made of polyurethane for atraumatic entry and to minimize injury to venous vasculature. The nose cone 28 can also be radiopaque to provide for visibility under fluoroscopy.

The nose cone shaft 30 may include a lumen sized and configured to slidably accommodate a guide wire so that the delivery system 10 can be advanced over the guide wire through the vasculature. However, embodiments of the system 10 discussed herein may not use a guide wire and thus the nose cone shaft 30 can be solid. The nose cone shaft 30 may be connected from the nose cone 28 to the handle, or may be formed of different segments such as the other assemblies. Further, the nose cone shaft 30 can be formed of different materials, such as plastic or metal, similar to those described in detail above.

This view also illustrates that the nose cone shaft 36 can be slidably disposed within the inner assembly 18, thus allowing the nose cone shaft 28 (and thus nose cone 28) and the inner retention member 32 to move separately from one another during deployment and use.

The inner retention member 32 and outer retention ring 40 and the delivery system 10 generally may be similar to those disclosed in U.S. Pat. Nos. 8,414,644 and 8,652,203, the entire contents of both of which are hereby incorporated by reference herein and made a part of this specification. This is inclusive of the entire disclosure, including other apparatuses and methods described therein, and is not in any way limited to the disclosure of the inner and outer retentions and/or the delivery system.

Delivery Method

Methods of use of the delivery system in connection with any of the replacement mitral valves discussed herein will now be described. In particular, the delivery system 10 can be used in a method for percutaneous delivery of the replacement mitral valve to treat patients with moderate to severe mitral regurgitation. The below methods are just a few examples of the how the delivery system may be used. It will be understood that the delivery systems described herein can be used as part of other methods as well.

Figure 7:
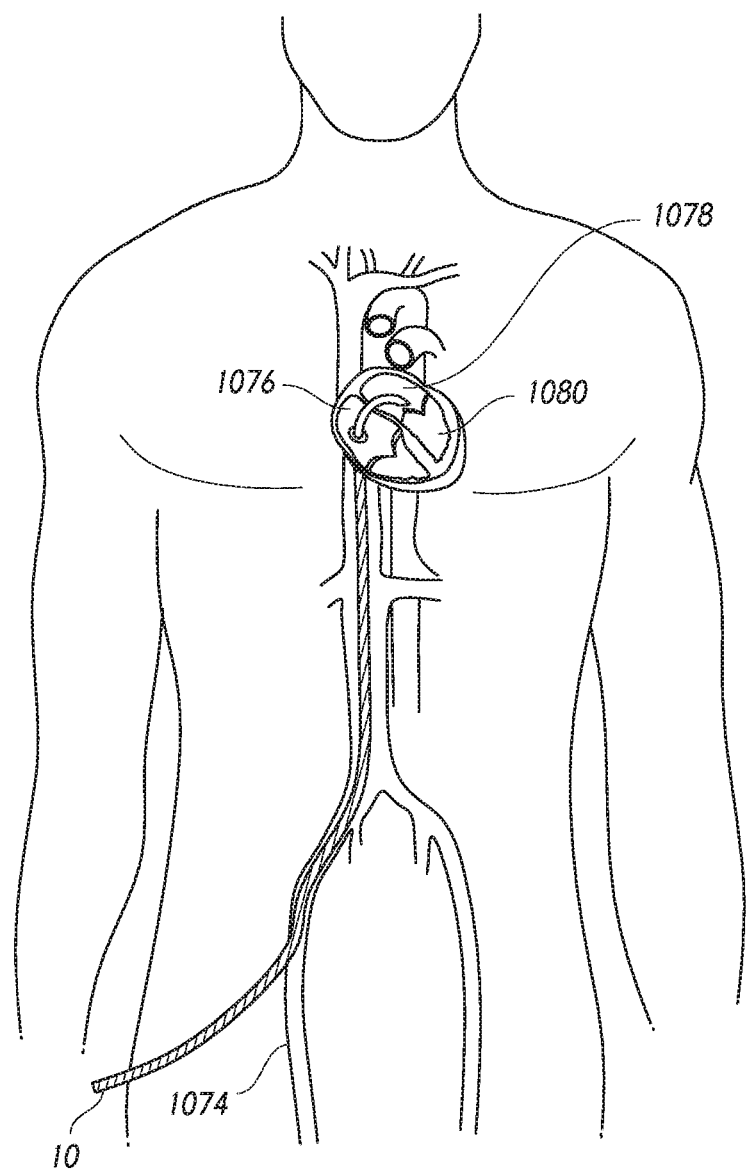
FIG. 7 illustrates a schematic representation of a transfemoral delivery approach.

As shown in FIG. 7, in one embodiment the delivery system 10 can be placed in the ipsilateral femoral vein 1074 and advanced to the right atrium 1076. A transseptal puncture using known techniques can then be performed to obtain access to the left atrium 1078. The delivery system 10 can then be advanced in to the left atrium 1078 and then to the left ventricle 1080. FIG. 7 shows the delivery system 10 extending from the ipsilateral femoral vein 1074 to the left atrium 1078. In embodiments of the disclosure, a guide wire is not necessary to position the delivery system 10 in the proper position, although in other embodiments, one or more guide wires may still be used.

Accordingly, it can be advantageous for a user to be able to steer the delivery system 10 through the complex areas of the heart in order to place a replacement mitral valve in line with the native mitral valve. This task can be performed with or without the use of a guide wire with the above disclosed system. The distal end of the delivery system can be inserted into the left atrium 1078. A user can then turn the steering knob 610 on the handle 14 in order to cause bending of the mid shaft 50, and thus the distal end of the delivery system 10. A user can then continue to pass the bent delivery system through the transseptal puncture and into the left atrium 1078. A user can then further manipulate the steering knob 610 to create an even greater bend in the mid shaft 50. Further, a user can torque the entire delivery system 10 to further manipulate and control the position of the delivery system 10. In the fully bent configuration, a user can then place the replacement mitral valve in the proper location. This can advantageously allow delivery of a replacement valve to an in situ implantation site, such as a native mitral valve, via a wider variety of approaches, such as a transseptal approach.

Further descriptions of the delivery methodology, as well of a discussion of a guide wire which can be used in some embodiments, can be found in U.S. Patent Publication No. 2017/0277670.

Figure 8:
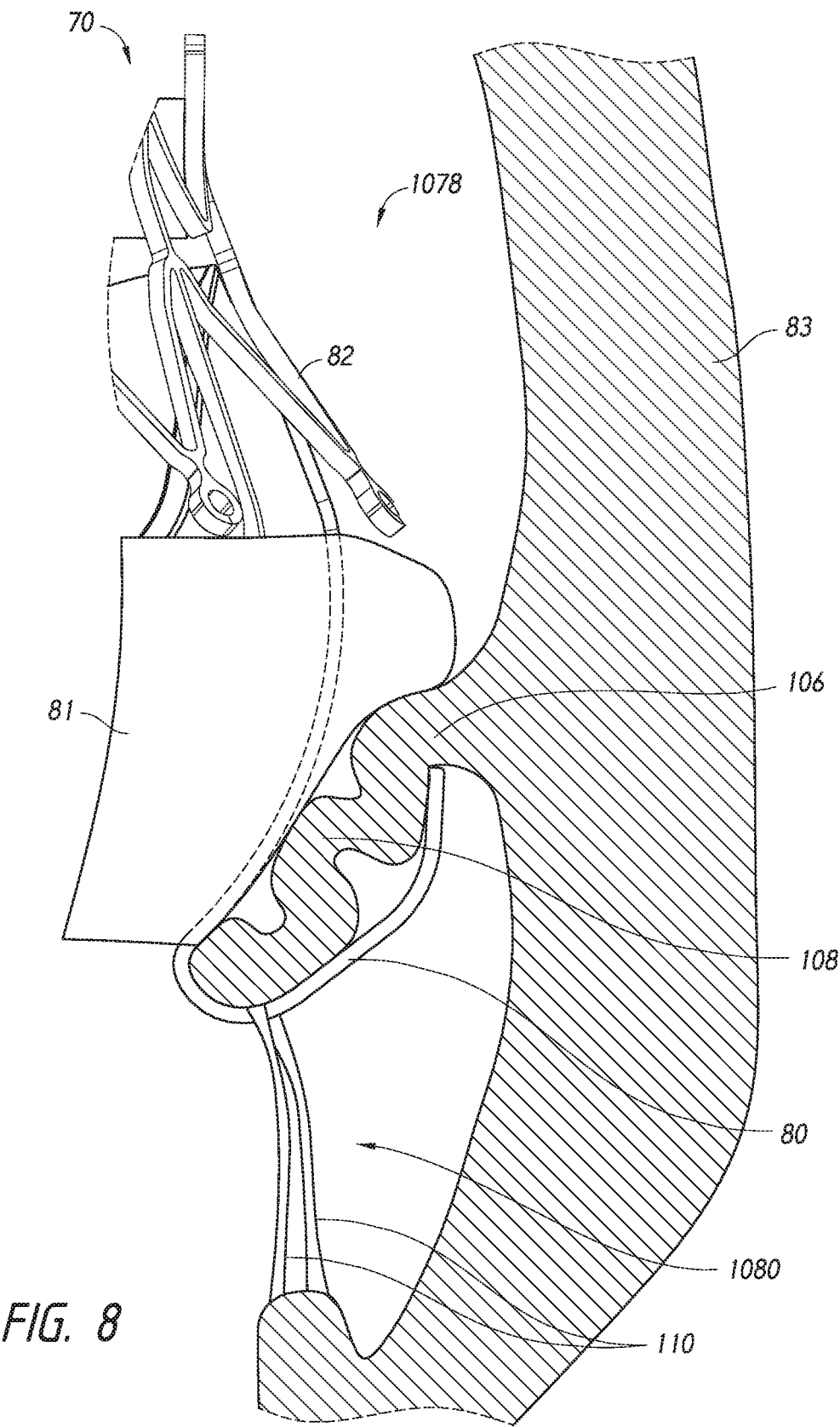
FIG. 8 illustrates a schematic representation of a valve prosthesis positioned within a native mitral valve.

Reference is now made to FIG. 8 which illustrates a schematic representation of an embodiment of a replacement heart valve (prosthesis 70) positioned within a native mitral valve of a heart 83. Further details regarding how the prosthesis 70 may be positioned at the native mitral valve are described in U.S. Publication No. 2015/0328000, published on Nov. 19, 2015, the entirety of which is hereby incorporated by reference, including but not limited to FIGS. 13A-15 and paragraphs [0036]-[0045]. A portion of the native mitral valve is shown schematically and represents typical anatomy, including a left atrium 1078 positioned above an annulus 106 and a left ventricle 1080 positioned below the annulus 106. The left atrium 1078 and left ventricle 1080 communicate with one another through a mitral annulus 106. Also shown schematically in FIG. 8 is a native mitral leaflet 108 having chordae tendineae 110 that connect a downstream end of the mitral leaflet 108 to the papillary muscle of the left ventricle 1080. The portion of the prosthesis 70 disposed upstream of the annulus 106 (toward the left atrium 1078) can be referred to as being positioned supra-annularly. The portion generally within the annulus 106 is referred to as positioned intra-annularly. The portion downstream of the annulus 106 is referred to as being positioned sub-annularly (toward the left ventricle 1080).

As shown in the situation illustrated in FIG. 8, the replacement heart valve (e.g., prosthesis 70) can be disposed so that the mitral annulus 106 is between the ventricular anchors 80 and the atrial anchors 82. In some situations, the prosthesis 70 can be positioned such that ends or tips of the ventricular anchors 80 contact the annulus 106 as shown, for example, in FIG. 8. In some situations, the prosthesis 10 can be positioned such that ends or tips of the ventricular anchors 80 do not contact the annulus 106. In some situations, the prosthesis 70 can be positioned such that the ventricular anchors 80 do not extend around the leaflet 108. Further, the prosthesis 70 can be at least partially surrounded by an annular flap 81 between the distal anchors 82 and the atrial anchors 82. This flap 81 can wrap around the frame of the prosthesis 70 and help position the prosthesis 70 in the desired position in the body.

As illustrated in FIG. 8, the replacement heart valve 70 can be positioned so that the ends or tips of the ventricular anchors 80 are on a ventricular side of the mitral annulus 106 and the ends or tips of the atrial anchors 82 are on an atrial side of the mitral annulus 106. The ventricular anchors 80 can be positioned such that the ends or tips of the ventricular anchors 80 are on a ventricular side of the native leaflets beyond a location where chordae tendineae 110 connect to free ends of the native leaflets. The ventricular anchors 80 may extend between at least some of the chordae tendineae 110 and, in some situations such as those shown in FIG. 8, can contact or engage a ventricular side of the annulus 106. It is also contemplated that in some situations, the ventricular anchors 80 may not contact the annulus 106, though the ventricular anchors 80 may still contact the native leaflet 108. In some situations, the ventricular anchors 80 can contact tissue of the left ventricle 104 beyond the annulus 106 and/or a ventricular side of the leaflets.

During delivery, the ventricular anchors 80 (along with the frame) can be moved toward the ventricular side of the annulus 106 with the ventricular anchors 80 extending between at least some of the chordae tendineae 110 to provide tension on the chordae tendineae 110. The degree of tension provided on the chordae tendineae 110 can differ. For example, little to no tension may be present in the chordae tendineae 110 where the leaflet 108 is shorter than or similar in size to the ventricular anchors 80. A greater degree of tension may be present in the chordae tendineae 110 where the leaflet 108 is longer than the ventricular anchors 80 and, as such, takes on a compacted form and is pulled proximally. An even greater degree of tension may be present in the chordae tendineae 110 where the leaflets 108 are even longer relative to the ventricular anchors 80. The leaflet 108 can be sufficiently long such that the ventricular anchors 80 do not contact the annulus 106.

The atrial anchors 82 can be positioned such that the ends or tips of the atrial anchors 82 are adjacent the atrial side of the annulus 106 and/or tissue of the left atrium 1078 beyond the annulus 106. In some situations, some or all of the atrial anchors 82 may only occasionally contact or engage atrial side of the annulus 106 and/or tissue of the left atrium 1078 beyond the annulus 106. For example, as illustrate in FIG. 8, the atrial anchors 82 may be spaced from the atrial side of the annulus 106 and/or tissue of the left atrium 1078 beyond the annulus 106. The atrial anchors 82 could provide axial stability for the prosthesis 10. In some situations, some or all of the atrial anchors 82 may not contact an annular flap 81. This may occur when the annular flap 81 is in a collapsed configuration although it may also occur when the annular flap 81 is in an expanded configuration. In some situations, some or all of the atrial anchors 82 may contact the annular flap 81. This may occur when the annular flap 81 is in an expanded configuration although it may also occur when the annular flap 81 is in a collapsed configuration. It is also contemplated that some or all of the atrial anchors 82 may contact the atrial side of the annulus 106 and/or tissue of the left atrium 1078 beyond the annulus 106

The annular flap 81 can be positioned such that a proximal portion of the annular flap 81 is positioned along or adjacent an atrial side of the annulus 106. The proximal portion can be positioned between the atrial side of the annulus 106 and the atrial anchors 82. The proximal portion can extend radially outward such that the annular flap 81 is positioned along or adjacent tissue of the left atrium 1078 beyond the annulus 106. The annular flap 81 can create a seal over the atrial side of the annulus 106 when the flap 81 is in the expanded state.

Alternate Valve Prosthesis

Figure 9:
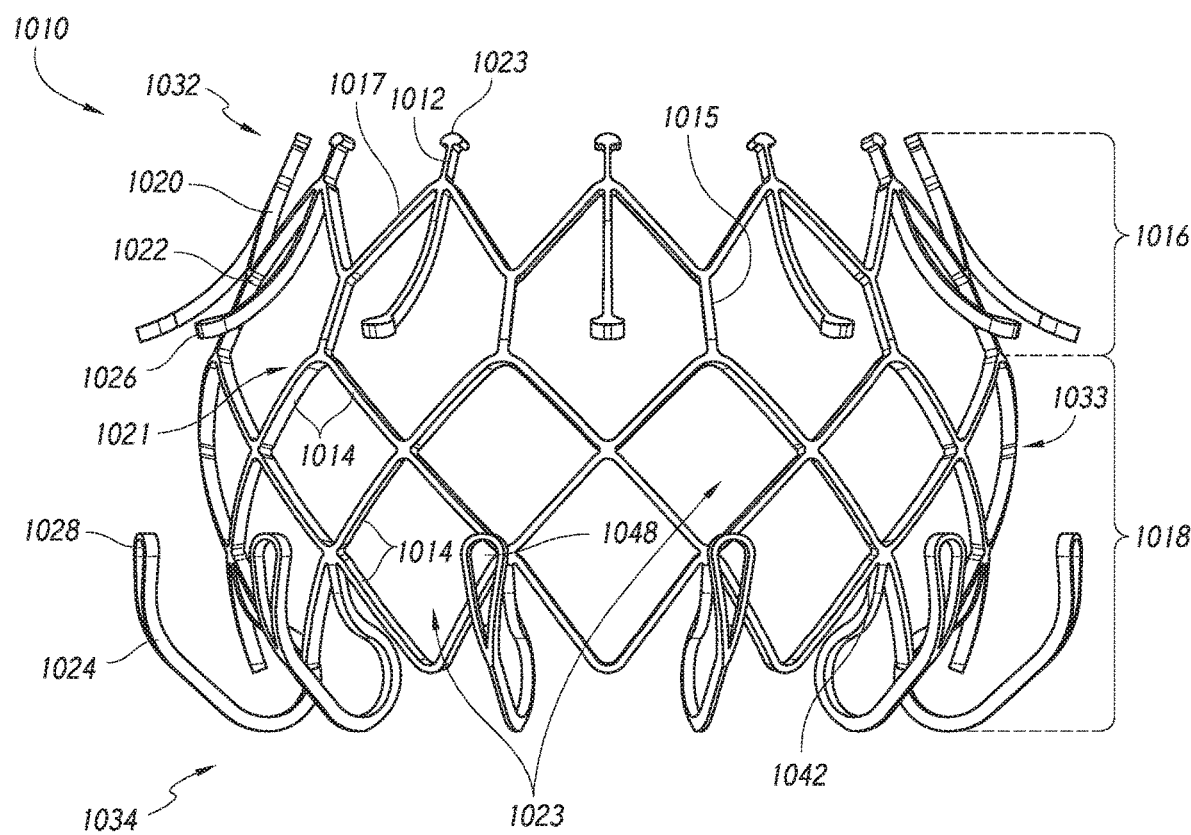
FIG. 9 shows a side view of an alternate embodiment of a valve prosthesis that may be delivered using the delivery systems described herein.
Figure 10:
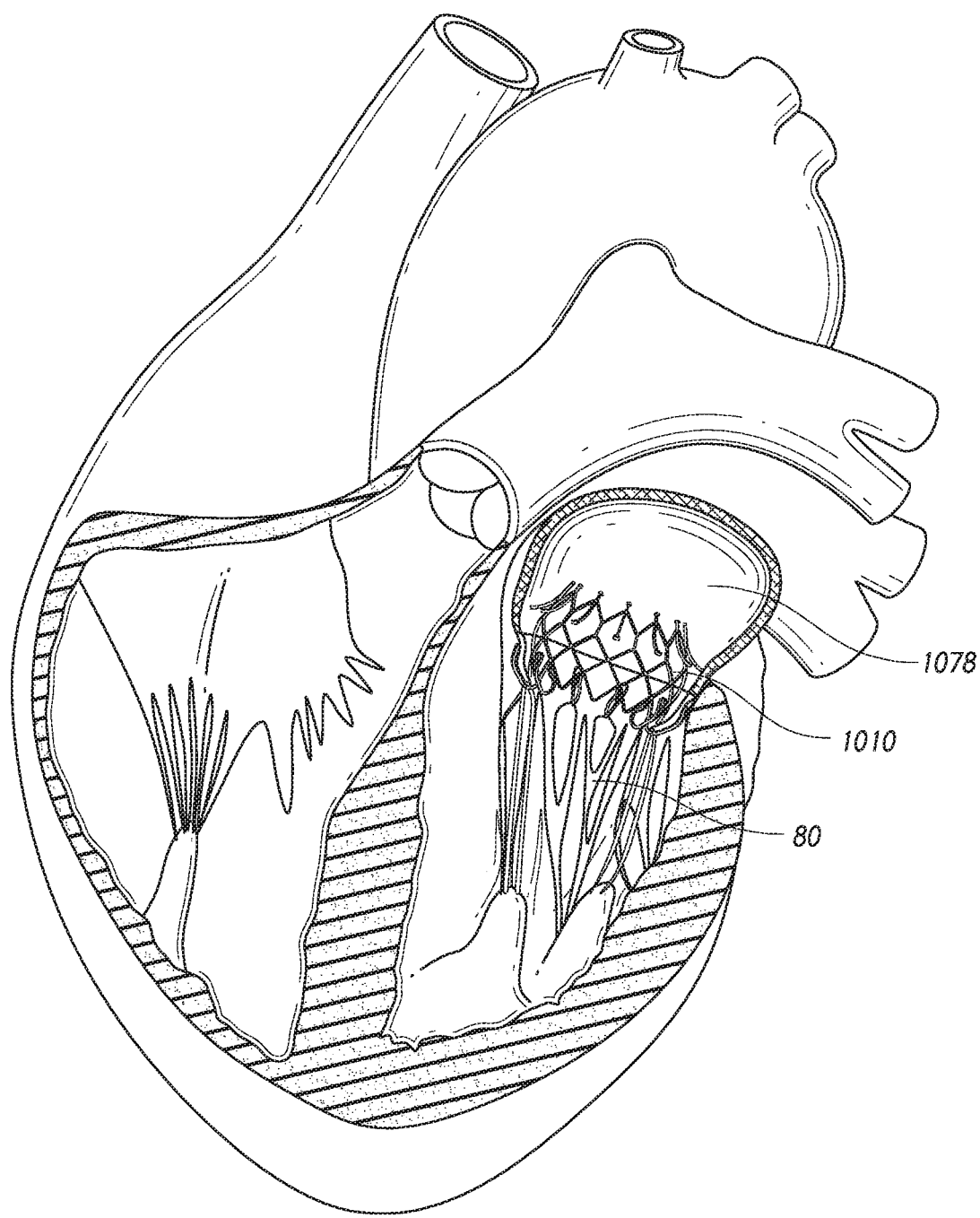
FIG. 10 shows the valve prosthesis frame of FIG. 9 located within a heart.
Figure 11:
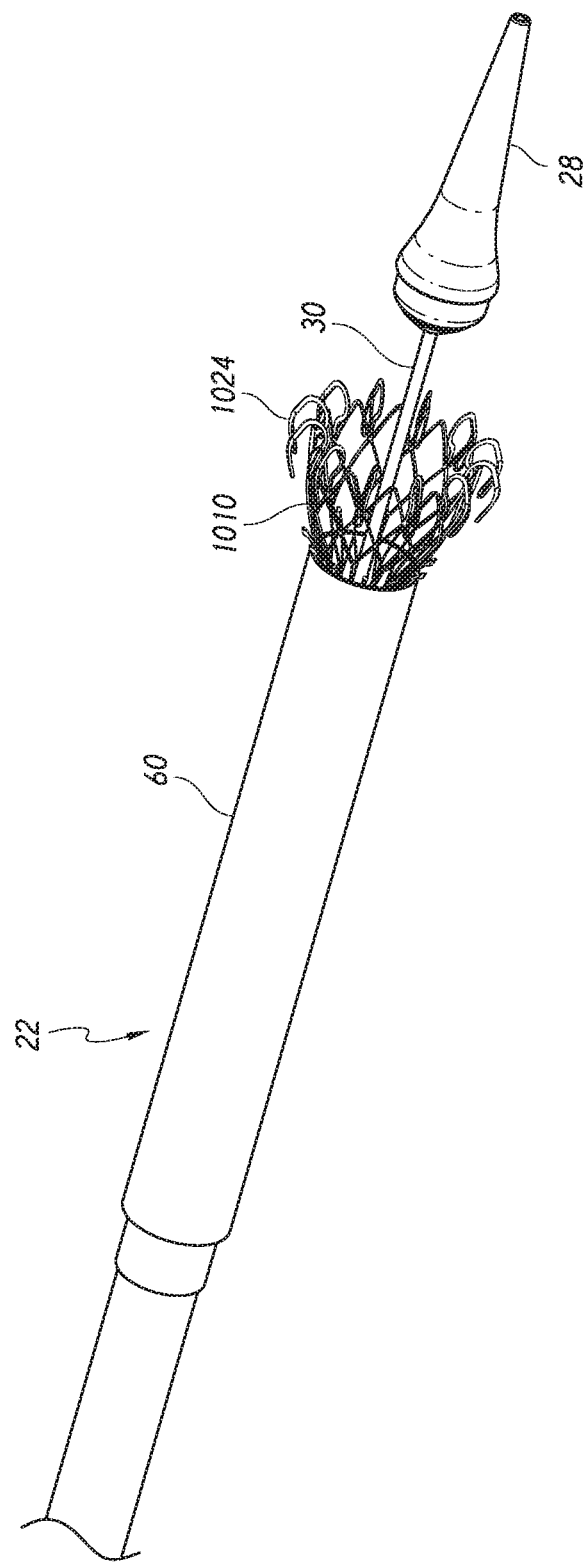
FIGS. 11-14 show steps of a method for delivery of the valve prosthesis of FIG. 9 to an anatomical location.

FIG. 9 illustrates an alternate embodiment of a valve prosthesis 1010 which can be used in conjunction with the delivery systems disclosed herein. The illustrated prosthesis 1010 includes a frame 1020 that may be self-expanding or balloon expandable. The prosthesis 1010 may be a replacement valve that can be designed to replace a damaged or diseased native heart valve such as a mitral valve, as discussed above. The additional features of the replacement valve are not shown in FIG. 9 in order to more clearly illustrate features of the frame 1020. It will also be understood that the prosthesis 1010 is not limited to being a replacement valve. In addition, it will be understood in FIG. 9, that only a front portion of the frame 1020 is shown for further ease of illustration. FIG. 10 illustrates the frame 1020 located within a heart.

Delivery Method

FIGS. 11-14 illustrate a method of delivery of the prosthesis 1010 to a desired anatomical position in a patient, such as to replace a mitral valve, to illustrate how the delivery system 10 is utilized to release the prosthesis. While the below disclosure is discussed with relation to prosthesis 1010, similar or the same procedure can be performed with respect to prosthesis 70. During the initial insertion of the prosthesis 1010 and the delivery system 10 into the body, the prosthesis 1010 can be located within the system 10, similar to as shown in FIG. 2A. The distal end 1034 of the prosthesis 1010, and specifically the distal anchors 1024, are restrained within the third segment 60 of the outer sheath assembly 22, thus preventing expansion of the prosthesis 1010. Similar to what is shown in FIG. 2A, the distal anchors 1024 can extend distally when positioned in the third segment 60. The proximal end 1032 of the prosthesis 1010 is restrained within the outer retention ring 40 and within a portion of the inner retention member 32.

The system 10 can first be positioned to a particular location in a patient's body, such as at the native mitral valve, through the use of the steering mechanisms discussed herein or other techniques. With reference next to the step of FIG. 11 once the system 10 has positioned the prosthesis 1010 at the in situ target location, e.g. the native mitral valve, the outer sheath assembly 22 can be moved relatively proximally away from the nose cone 28 to uncover at least a portion of the prosthesis 1010, in particular the distal end 1034 of the prosthesis 1010. At this point, the distal anchors 1024 can flip proximally and the distal end 1034 begins to expand radially outward. For example, if the system 10 has been delivered to a native mitral valve location through a transseptal approach, the nose cone is positioned in the left ventricle, thus having the prosthesis 1010 be generally perpendicular to the plane of the mitral annulus. The distal anchors 1024, which may be considered ventricular anchors, expand radially outward within the left ventricle. The distal anchors 1024 can be located above the papillary heads, but below the mitral annulus and mitral leaflets. In some embodiments, the distal anchors 1024 may contact and/or extend between the chordae in the left ventricle, as well as contact the leaflets, as they expand radially. In some embodiments, the distal anchors 1024 may not contact and/or extend between the chordae or contact the leaflets. Depending on the position of the prosthesis 1010, the distal ends of the distal anchors 1024 may be at or below where the chordae connect to the free edge of the native leaflets.

Figure 12:
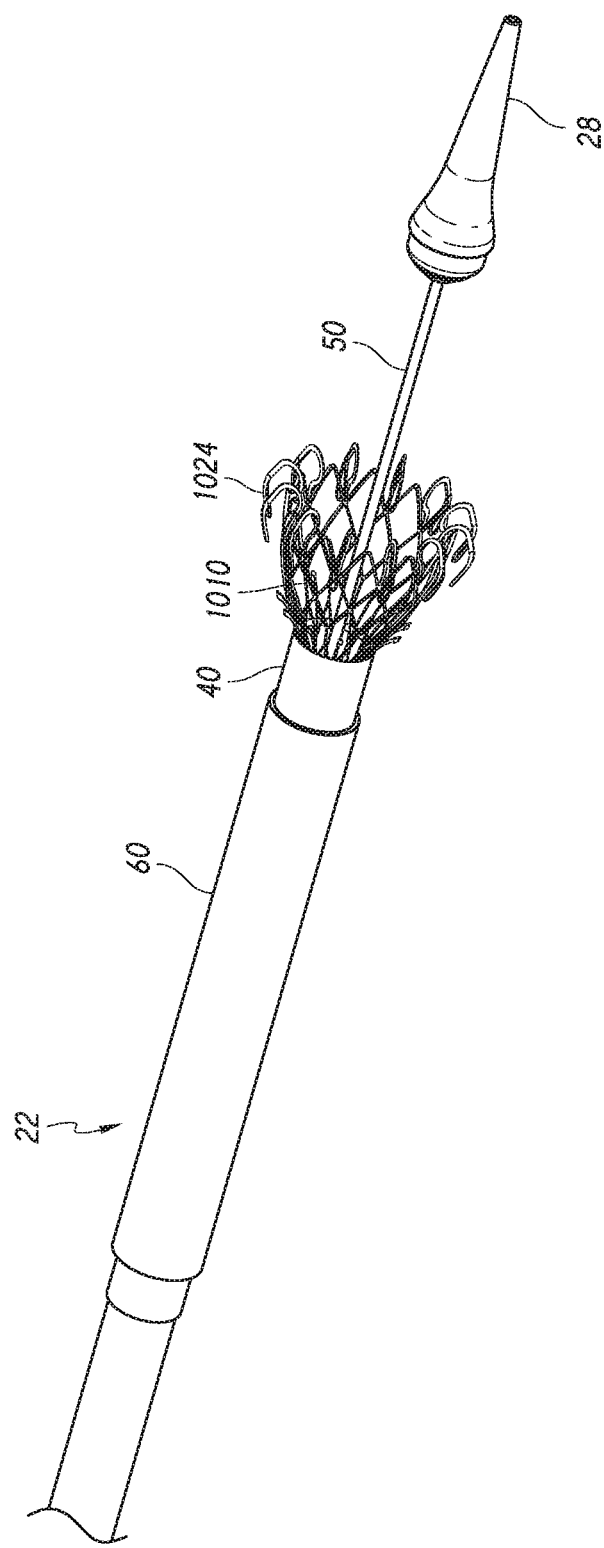

With reference next to the step of FIG. 12, outer sheath assembly 22 can be further moved relatively away from the nose cone 28 to further uncover the prosthesis 1010. As shown in the illustrated embodiment, the distal end 1034 of the prosthesis 1010 is expanded outwardly. It should be noted that the proximal end 1032 of the prosthesis 1010 can remain covered by the outer retention ring 40 during this step such that the proximal end 1032 remains in a radially compacted state. At this time, the system 10 may be withdrawn proximally so that the distal anchors 1024 capture and engage the leaflets of the mitral valve, or may be moved proximally to reposition the prosthesis 1010. Further, the system 10 may be torqued, which may cause the distal anchors 1024 to put tension on the chordae through which at least some of the distal anchors may extend between. However, in some embodiments the distal anchors 1024 may not put tension on the chordae. In some embodiments, the distal anchors 1024 may capture the native leaflet and be between the chordae without any further movement of the system 10 after withdrawing the outer sheath assembly 22.

Accordingly, during this step the system 10 may be moved proximally or distally to cause the distal or ventricular anchors 1024 to properly capture the native mitral valve leaflets. In particular, the tips of the ventricular anchors 1024 may be moved proximally to engage a ventricular side of the native annulus, so that the native leaflets are positioned between the anchors 1024 and the body of the prosthesis 1010. When the prosthesis 1010 is in its final position, there may or may not be tension on the chordae, though the distal anchors 1024 can be located between at least some of the chordae.

Figure 13:
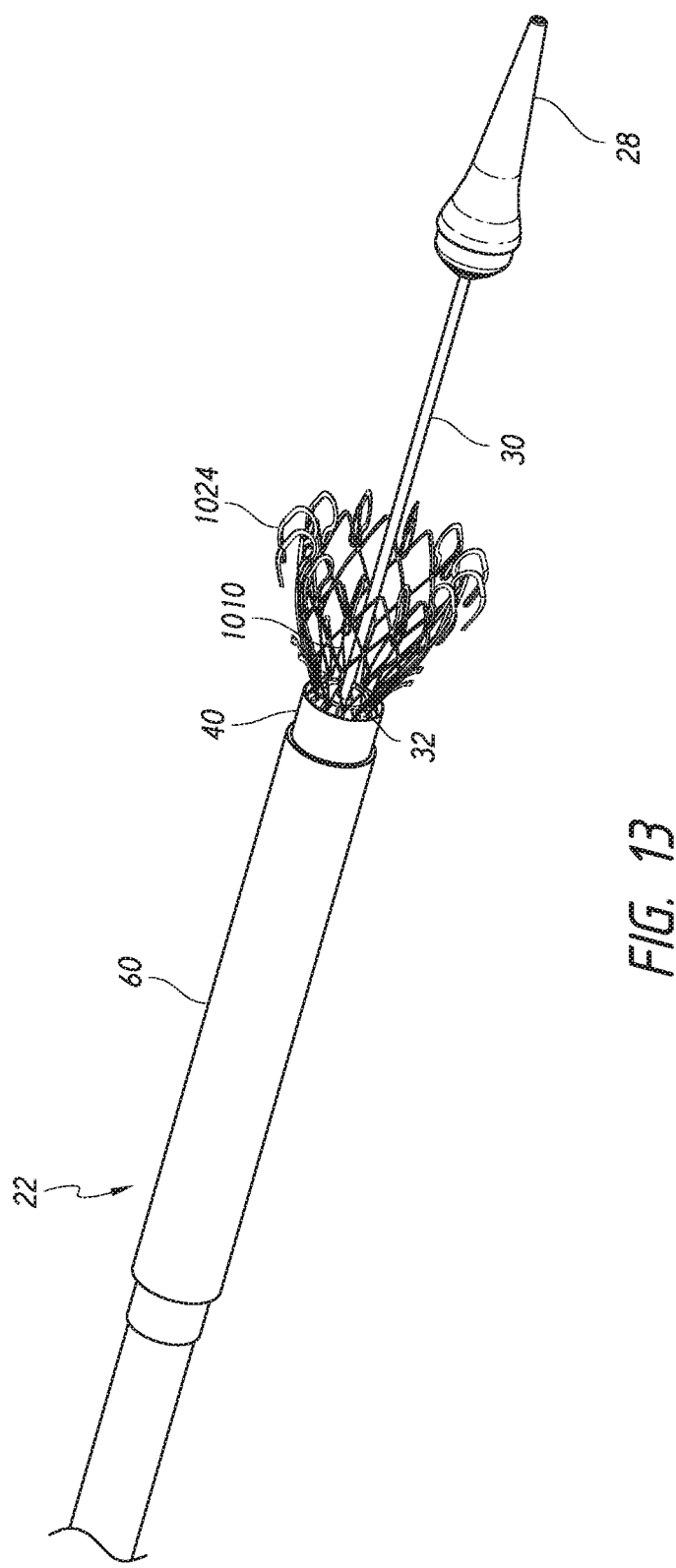

As shown in FIG. 13, once the distal end 1034 of the prosthesis 1010 is fully expanded (or as fully expanded as possible at this point), the outer retention ring 40 can be moved relatively proximally to expose the inner retention member 32, thus beginning the expansion of the proximal end 1032 of the prosthesis 1010. For example, in a mitral valve replacement procedure, after the distal or ventricular anchors 1024 are positioned between at least some of the chordae tendineae and/or engage the native mitral valve annulus, the proximal end 1032 of the prosthesis 1010 may be expanded within the left atrium.

Figure 14:
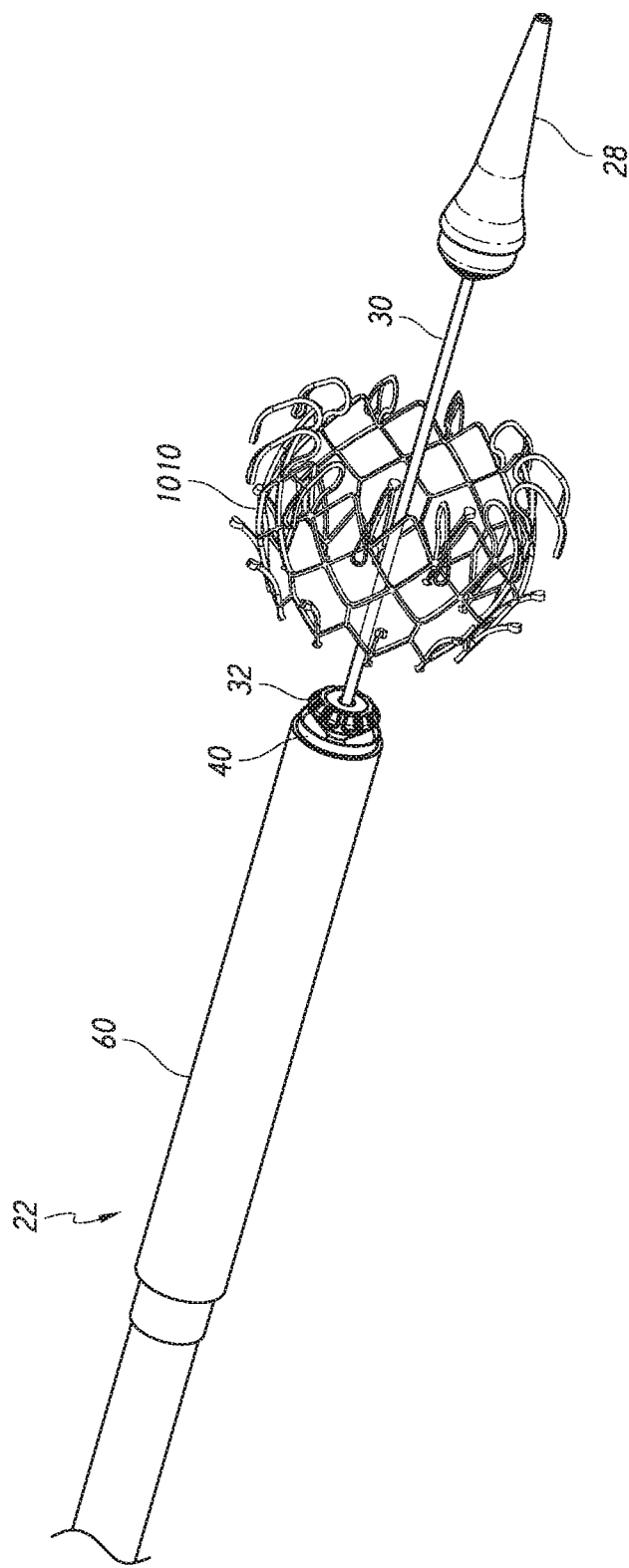

With reference next to the step of FIG. 14, the outer retention ring 40 can continue to be moved proximally such that the proximal end 1032 of the prosthesis 1010 can radially expand to its fully expanded configuration. After expansion and release of the prosthesis 1010, the nose cone 28 can be withdrawn through the center of the expanded prosthesis 1010 and into the outer sheath assembly 22. The system 10 can then be removed from the patient.

In some embodiments, the prosthesis 1010 can be delivered under fluoroscopy so that a user can view certain reference points for proper positioning of the prosthesis 1010. Further, echocardiography can be used for proper positioning of the prosthesis 1010.

FIGS. 15-17B show different steps of embodiments of a method of delivering the prosthesis 1010, or any other prosthesis disclosed herein, to the proper position in the heart.

Figure 15:
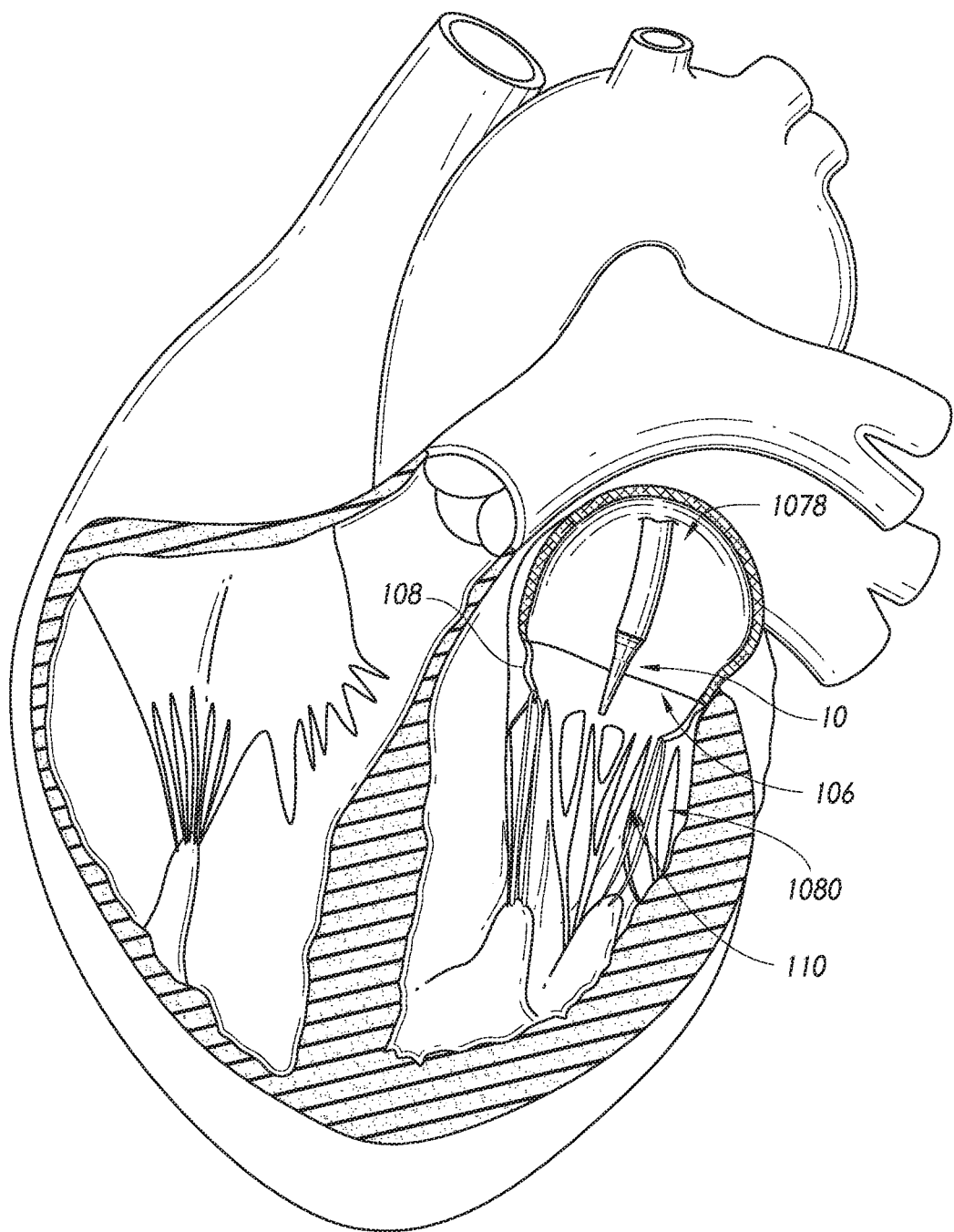
FIGS. 15-17B illustrate steps of embodiments of a transseptal method for delivery of a valve prosthesis to replace a mitral valve.

Prior to insertion of the delivery system 10, the access site into the patient can be dilated. Further, a dilator can be flushed with, for example, heparinized saline prior to use. The delivery system 10 can then be inserted over a guide wire. In some embodiments, any flush ports on the delivery system 10 can be pointed vertically. Further, if an introducer tube is used, integrated or otherwise, this can be stabilized. The delivery system 10 can be advanced through the septum until a distal end of the delivery system 10 is positioned across the septum into the left atrium 1078. Thus, the distal end of the delivery system 10 can be located in the left atrium 1078 as shown in FIG. 15. In some embodiments, the delivery system 10 can be rotated, such as under fluoroscopy, into a desired position. If a flexible system is being used, it can be operated to flex a distal end of the delivery system 10 towards the septum and mitral valve. The position of the delivery system 10, and the prosthesis 1010 inside, can be verified using echocardiography and fluoroscopic guidance.

In some embodiments, the prosthesis 1010 can be located, prior to release, above the mitral annulus 106, in line with the mitral annulus 106, or below the mitral annulus 106. In some embodiments, the prosthesis 1010 can be located, prior to expansion, fully above the mitral annulus 106, in line with the mitral annulus 106, just below the mitral annulus 106, or fully below the mitral annulus 106. In some embodiments, the prosthesis 1010 can be located, prior to expansion, partially above the mitral annulus 106, in line with the mitral annulus 106, or partially below the mitral annulus 106. In some embodiments, a pigtail catheter can be introduced into the heart to perform a ventriculogram for proper viewing.

In some embodiments, the position of the mitral plane and the height of any papillary muscles 2004 on the fluoroscopy monitor can be marked to indicate an example target landing zone. If needed, the delivery system 10 can be unflexed, reduced in rotation, and retracted to reduce tension on the delivery system 10 as well as reduce contact with the left ventricular wall, the left atrial wall, and/or the mitral annulus 106.

Further, the delivery system 10 can be positioned to be coaxial to the mitral annulus 106, or at least as much as possible, while still reducing contact with the left ventricular wall, the left atrial wall, and/or the mitral annulus 106 and reducing delivery system tension. An echo probe can be positioned to view the anterior mitral leaflet (AML), the posterior mitral leaflet (PML) (leaflets 108), mitral annulus 106, and outflow tract. Using fluoroscopy and echo imaging, the prosthesis 1010 can be confirmed to be positioned at a particular depth and desired alignment (e.g., coaxial alignment) with the mitral annulus 106.

Afterwards, the outer sheath assembly 22 can be retracted to expose the ventricular anchors 1024, thereby releasing them. In some embodiments, once exposed, the outer sheath assembly 22 can be reversed in direction to relieve tension on the outer sheath assembly 22. In some embodiments, reversing the direction could also serve to partially or fully capture the prosthesis 1010.

Figure 16A:
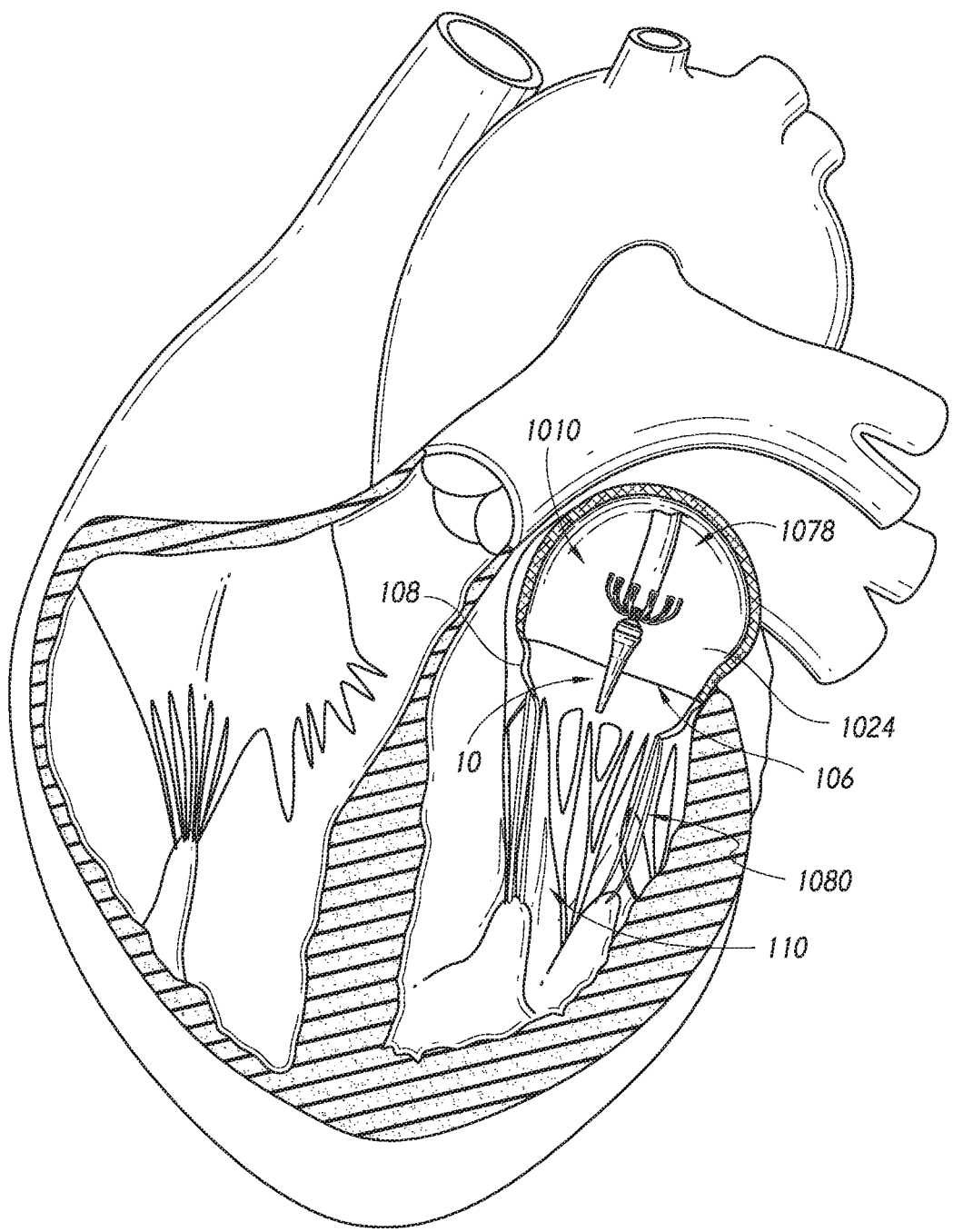

An embodiment of the position of the delivery system 10 for release of the ventricular anchors 1024 is shown in FIG. 16A. As shown, the distal anchors 1024 can be released in the left atrium 1078. Further, as shown the proximal anchors 1022 are not yet exposed. Moreover, the body of the prosthesis 1010 has not undergone any expansion at this point. However, in some embodiments, one or more of the distal anchors 1024 can be released in either the left atrium 1078 (e.g., super-annular release) or generally aligned with the mitral valve annulus 106 (e.g., intra-annular release), or just below the mitral valve annulus 106 (e.g., sub-annular release). In some embodiments, all of the distal anchors 1024 can be released together. In other embodiments, a subset of the distal anchors 1024 can be released while at a first position and another subset of the distal anchors 1024 can be released while at a second position. For example, some of the distal anchors 1024 can be released in the left atrium 1078 and some of the distal anchors 1024 can be released while generally aligned with the mitral valve annulus 106 or just below the mitral valve annulus 106.

If the distal anchors 1024 are released "just below" the mitral valve annulus 106, the may be released at 1 inch, ¾ inch, ½ inch, ¼ inch, ⅛ inch, 1/10 inch or 1/20 inch below the mitral valve annulus 106. In some embodiments, the distal anchors 1024 the may be released at less than 1 inch, ¾ inch, ½ inch, ¼ inch, ⅛ inch, 1/10 inch or 1/20 inch below the mitral valve annulus 106. This may allow the distal anchors 1024 to snake through the chordae upon release. This can advantageously allow the prosthesis 70 to slightly contract when making the sharp turn down toward the mitral valve. In some embodiments, this may eliminate the need for a guide wire assisting to cross the mitral valve. In some embodiments, the guide wire may be withdrawn into the delivery system 10 before or following release of the distal anchors 1024.

In some embodiments, the ventricular anchors 1024 can be released immediately after crossing the septum, and then the final trajectory of the delivery system 10 can be determined. Thus, the delivery system 10 can cross the septum, release the ventricular anchors 1024, establish a trajectory, and move into the left ventricle to capture the leaflets.

As discussed in detail above, upon release from the delivery system 10, the distal anchors 1024 can flip from extending distally to extending proximally as shown in FIG. 16A. This flip can be approximately 180°. Accordingly, in some embodiments, the distal anchors 1024 can be flipped in either the left atrium 1078 (e.g., super-annular flip), generally aligned with the mitral valve annulus 106 (e.g., intra-annular flip), or just below the mitral valve annulus 106 (e.g., sub-annular flip). The proximal anchors 1022 can remain within the delivery system 10. In some embodiments, all of the distal anchors 1024 can be flipped together. In other embodiments, a subset of the distal anchors 1024 can be flipped while at a first position and another subset of the distal anchors 1024 can be released while at a second position. For example, some of the distal anchors 1024 can be flipped in the left atrium 1078 and some of the distal anchors 1024 can be flipped while generally aligned with the mitral valve annulus 106 or just below the mitral valve annulus 106.

In some embodiments, the distal anchors 1024 may be positioned in line with the annulus 106 or just below the annulus 106 in the non-flipped position. In some embodiments, the distal anchors 1024 may be position in line with the annulus 106 or just below the annulus 106 in the flipped position. In some embodiments, prior to flipping the distal-most portion of the prosthesis 1010 can be located within or below the mitral valve annulus 106, such as just below the mitral valve annulus 106. However, flipping the anchors can cause, without any other movement of the delivery system 10, the distalmost portion of the prosthesis 1010/anchors 1024 to move upwards, moving it into the left atrium 1078 or moving it in line with the mitral annulus 106. Thus, in some embodiments the distal anchors 1024 can begin flipping at the annulus 106 but be fully within the left atrium 1078 upon flipping. In some embodiments the distal anchors 1024 can begin flipping below the annulus 106 but be fully within the annulus 106 upon flipping.

In some embodiments, the distal anchors 1024 can be proximal (e.g., toward the left atrium 1078) of a free edge of the mitral leaflets 108 upon release and flipping, such as shown in FIG. 16A. In some embodiments, the distal anchors 1024 can be aligned with (e.g., toward the left atrium 1078) a free edge of the mitral leaflets 108 upon release and flipping. In some embodiments, the distal anchors 1024 can be proximal (e.g., toward the left atrium 1078) of a free edge of the mitral valve annulus 106 upon release and flipping. In some embodiments, the distal anchors 1024 can be aligned with (e.g., toward the left atrium 1078) a free edge of the mitral valve annulus 106 upon release and flipping.

Thus, in some embodiments the distal anchors 1024 can be released/flipped above where the chordae 110 attach to the free edge of the native leaflets 108. In some embodiments the distal anchors 1024 can be released/flipped above where some the chordae 110 attach to the free edge of the native leaflets 108. In some embodiments the distal anchors 1024 can be released/flipped above where all the chordae 110 attach to the free edge of the native leaflets 108. In some embodiments, the distal anchors 1024 can be released/flipped above the mitral valve annulus 106. In some embodiments, the distal anchors 1024 can be released/flipped above the mitral valve leaflets 108. In some embodiments, the distal anchors 1024 can be released/flipped generally in line with the mitral valve annulus 106. In some embodiments, the distal anchors 1024 can be released/flipped generally in line with the mitral valve leaflets 108. In some embodiments, the tips of the distal anchors 1024 can be released/flipped generally in line with the mitral valve annulus 106. In some embodiments, the tips of the distal anchors 1024 can be released/flipped generally in line with the mitral valve leaflets 108. In some embodiments the distal anchors 1024 can be released/flipped below where some the chordae 110 attach to the free edge of the native leaflets 108. In some embodiments the distal anchors 1024 can be released/flipped below where all the chordae 110 attach to the free edge of the native leaflets 108. In some embodiments, the distal anchors 1024 can be released/flipped below the mitral valve annulus 106. In some embodiments, the distal anchors 1024 can be released/flipped below the mitral valve leaflets 108.

Figure 16B:
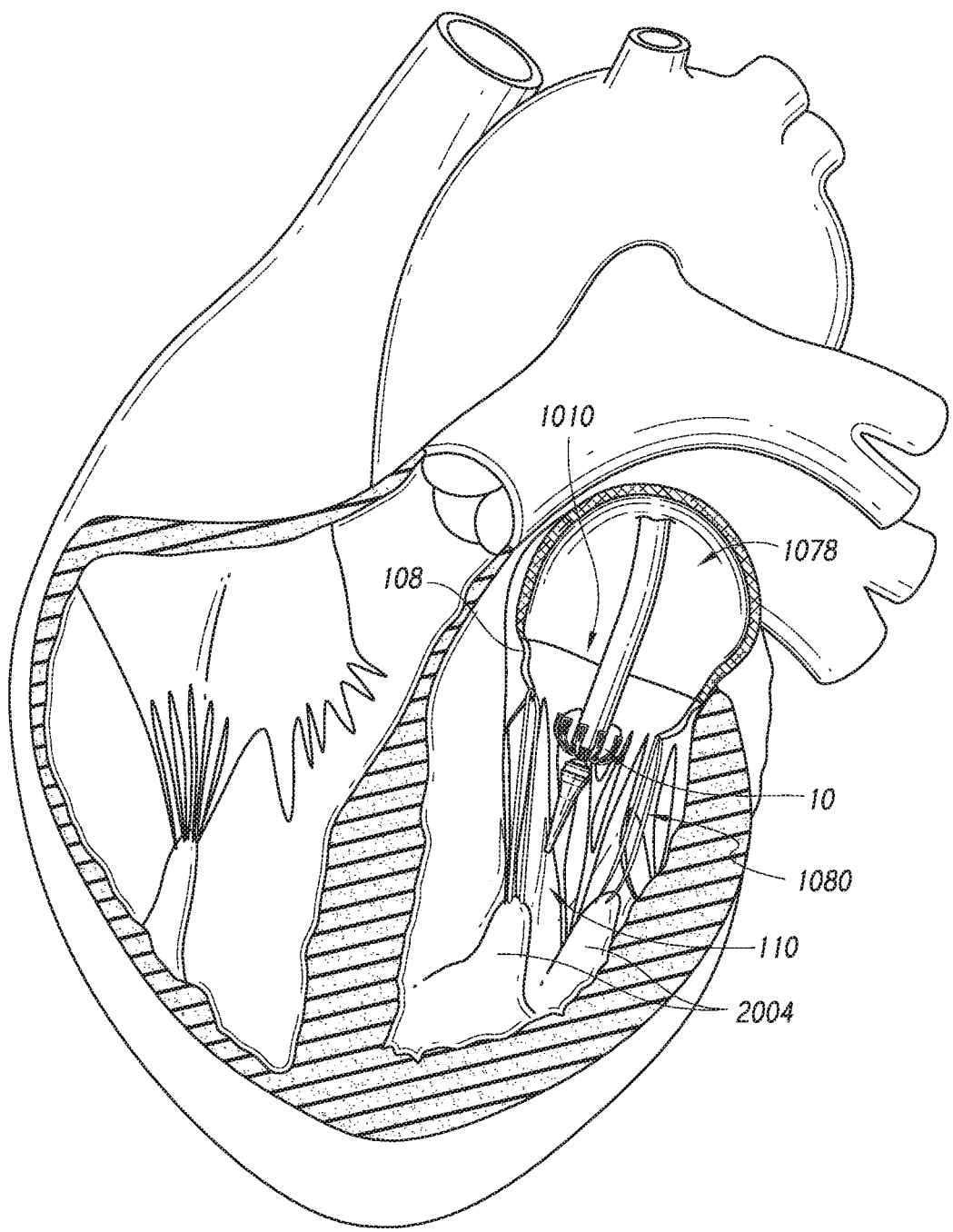

Once the distal anchors 1024 are released and flipped, the delivery system 10 can be translated towards the left ventricle 1080 through the mitral valve annulus 106 so that the distal anchors 1024 enter the left ventricle 1080 as shown in FIG. 16B. In some embodiments, the distal anchors 1024 can compress when passing through the mitral valve annulus 106. In some embodiments, the prosthesis 1010 can compress when passing through the mitral valve annulus 106. In some embodiments, the prosthesis 1010 does not compress when it passes through the mitral annulus 106. The distal anchors 1024 can be delivered anywhere in the left ventricle 1080 between the leaflets 108 and the papillary heads 2004. Thus, the system 10 may be directed more towards the papillary heads 2004 than shown in FIG. 16B to capture the leaflets 108. The particular location is not limiting.

In some embodiments, the distal anchors 1024 are fully expanded prior to passing through the mitral valve annulus 106. In some embodiments, the distal anchors 1024 are partially expanded prior to passing through the mitral valve annulus 106 and continued operation of the delivery system 10 can fully expand the distal anchors 1024 in the left ventricle 1080.

When the distal anchors 1024 enter the left ventricle 1080, the distal anchors 1024 can pass through the chordae 110 and move behind the mitral valve leaflets 108, thereby capturing the leaflets 108. In some embodiments, the distal anchors 1024 and/or other parts of the prosthesis 1010 can push the chordae 110 and/or the mitral valve leaflets 108 outwards.

Thus, after release of the distal anchors 1024, the delivery system 10 can then be repositioned as needed so that the ends of the left distal anchors 1024 are at the same level of the free edge of the native mitral valve leaflets 108 as shown in FIG. 16B. The delivery system 10 can also be positioned to be coaxial to the mitral annulus 106 if possible while still reducing contact with the left ventricular wall, the left atrial wall, and/or the annulus 106.

Figure 16C:
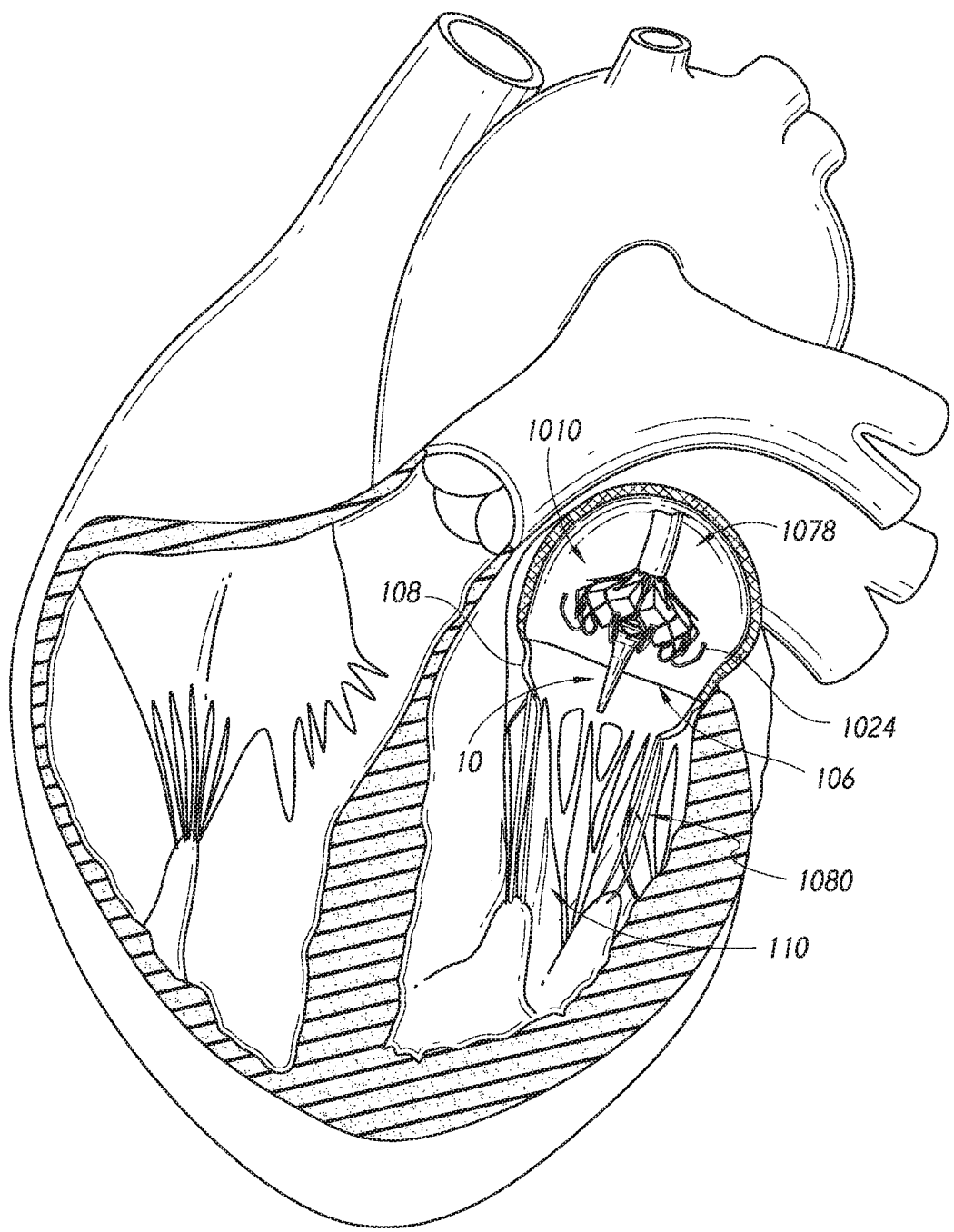
Figure 16D:
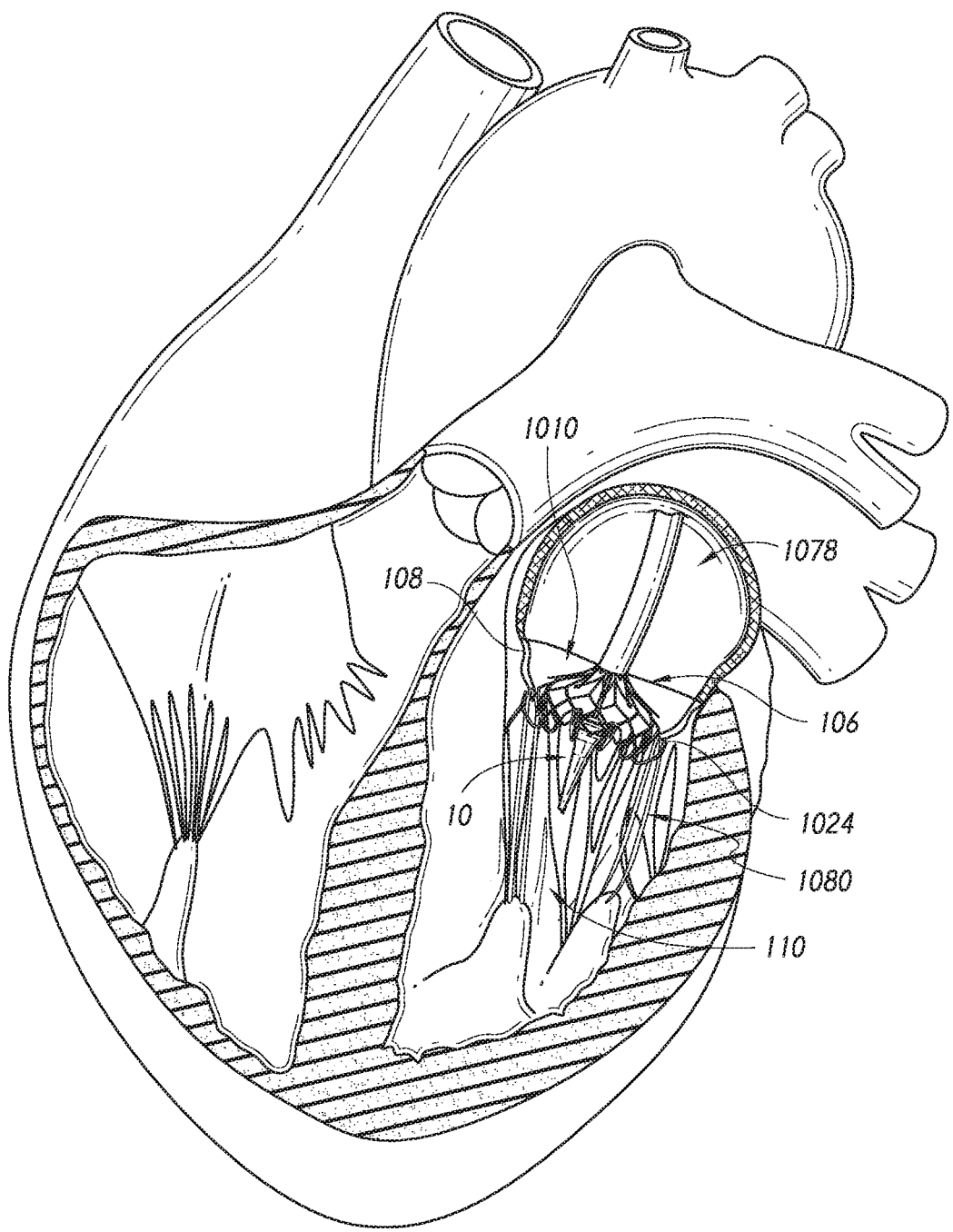

As shown above, in some embodiments, only the distal anchors 1024 are released in the left atrium 1078 before the prosthesis 1010 is move to a position within, or below, the annulus. In some alternate embodiments, the distal end of the prosthesis 1010 can be further expanded in the left atrium 1078, as shown in FIG. 16C. Thus, instead of the distal anchors 1024 flipping and no portion of the prosthesis 1010 body expanding, a portion of the prosthesis 1010 can be exposed and allowed to expand in the left atrium 1078. This partially exposed prosthesis 1010 can then be passed through the annulus 106 into the left ventricle 1080, such as shown in FIG. 16D. Further, the proximal anchors 1022 can be exposed. This is an alternative methodology as compared to FIGS. 16A-B. In some embodiments, the entirety of the prosthesis 1010 can be expanded within the left atrium 1078.

To facilitate passage through the annulus 106, the delivery system 10 can include a leader element (not shown) which passes through the annulus 106 prior to the prosthesis 10 passing through the annulus 106. For example, the leader element can include an expandable member, such as an expandable balloon, which can help maintain the shape, or expand, the annulus 106. The leader element can have a tapered or rounded shape (e.g., conical, frustoconical, semi-spherical) to facilitate positioning through and expansion of the annulus 106. In some embodiments, the delivery system 10 can include an engagement element (not shown) which can apply a force on the prosthesis 1010 to force the prosthesis 1010 through the annulus 106. For example, the engagement element can include an expandable member, such as an expandable balloon, positioned within or above the prosthesis 1010.

In some embodiments, to facilitate passage through the annulus 106, a user can re-orient the prosthesis 1010 prior to passing the prosthesis 1010 through the annulus 106. For example, a user can re-orient the prosthesis 1010 such that it passes through the annulus 106 sideways.

However, if only the distal anchors 1024 are flipped, and no other expansion occurs such as shown in FIGS. 16A-B, the expansion shown in FIG. 16C can be skipped and the prosthesis can instead be partially expanded in the ventricle 1080 to the position shown in FIG. 16D. Thus, when the prosthesis 1010 is in the proper location, the distal end can be allowed to expand to capture the leaflets 108. If the distal end is already expanded, such as from FIG. 16C, no more expansion may take place or the distal end can be further expanded.

Further, the PML and AML 106 can be captured, for example by adjusting the depth and angle of the prosthesis 1010. If a larger prosthesis diameter is needed to capture the leaflets 106, the outer sheath assembly 22 can be retracted until the desired diameter of the prosthesis 1010 is achieved. Capture of the leaflets 106 can be confirmed through echo imaging. In some embodiments, a user can confirm that the prosthesis 1010 is still in the appropriate depth and has not advanced into the left ventricle 1080. The position can be adjusted as needed.

Figure 16E:
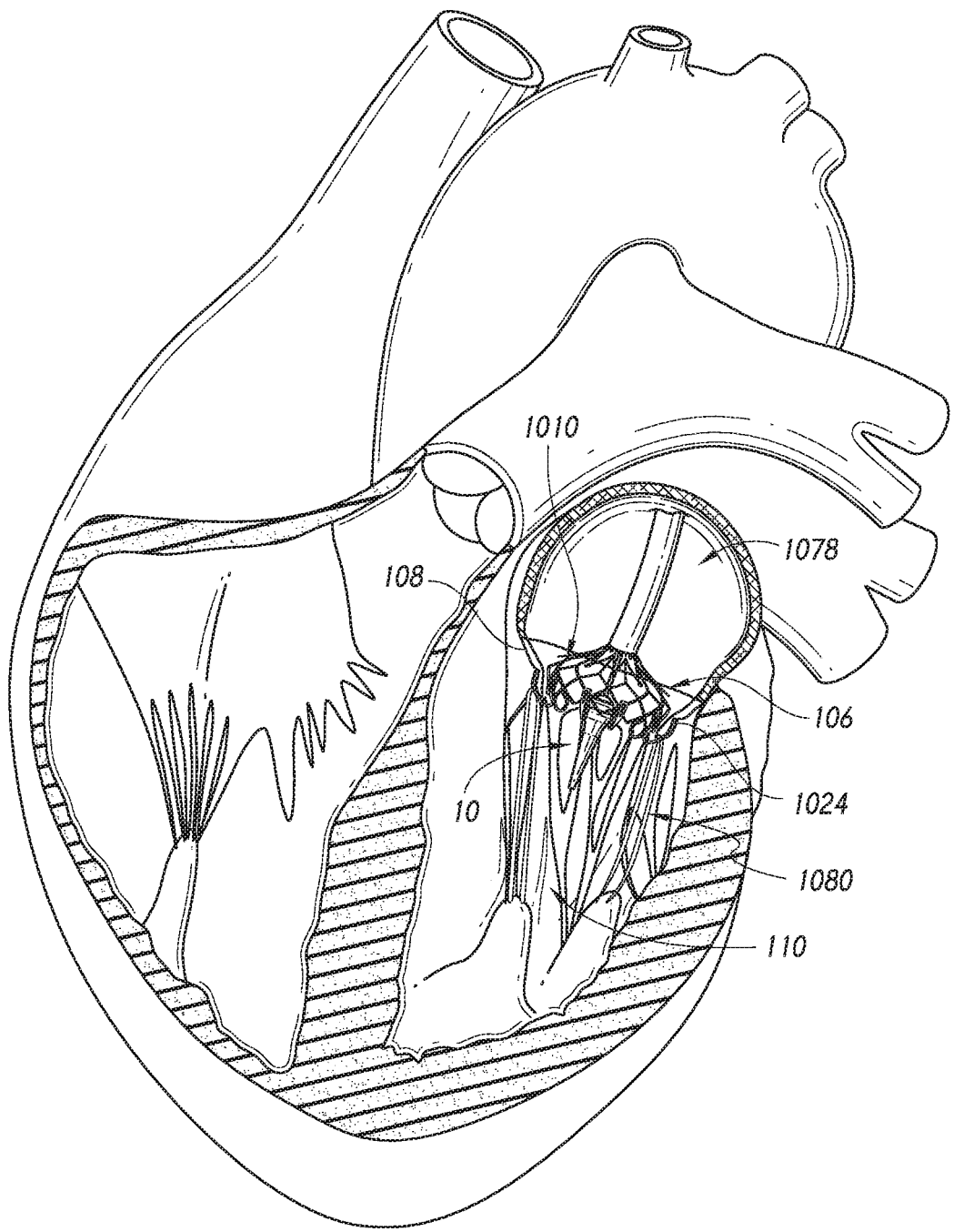

In some embodiments, once the distal anchors 1024 enter the left ventricle 1080 the system 10 can be pulled backwards (e.g., towards the left atrium 1078) to fully capture the leaflets 108 as shown in FIG. 16E. In some embodiments, the system 10 does not need to be pulled backwards to capture the leaflets 108. In some embodiments, systolic pressure can push the leaflets 108 upwards to be captured by the distal anchors 1024. In some embodiments, systolic pressure can push the entire prosthesis 1010 up towards the mitral annulus 106 after the leaflets 108 are captured and the prosthesis 1010 is fully or partially released. In some embodiments, a user can rotate the delivery system 10 and/or prosthesis 1010 prior to and/or while pulling the delivery system 10 backwards. In some instances, this can beneficially engage a greater number of chordae tendineae.

The outer sheath assembly 22 can be further retracted to fully expand the prosthesis. Once the prosthesis 1010 is fully exposed, the delivery system 10 can be maneuvered to be coaxial and height relative to the mitral annulus 106, such as by flexing, translating, or rotating the delivery system 10. As needed, the prosthesis 1010 can be repositioned to capture the free edge of the native mitral valve leaflets 108. Once full engagement of the leaflets 108 is confirmed, the prosthesis 1010 can be set perpendicular (or generally perpendicular) to the mitral annular plane.

Figure 16F:
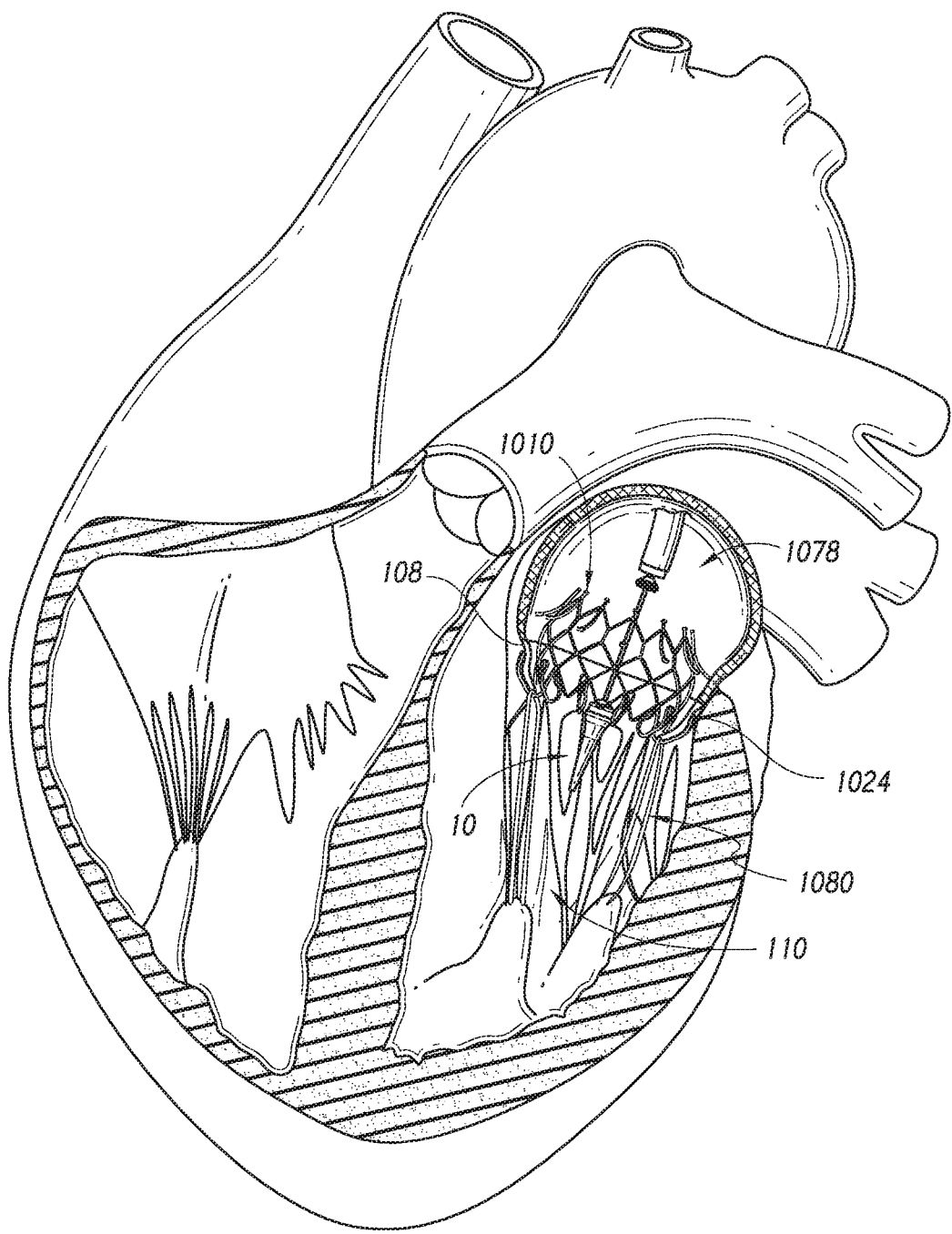

Following, the mid shaft 50 can be withdrawn until the left proximal anchors 1022 are exposed as shown in FIG. 16F. The mid shaft 50 can then be reversed in direction to relieve any tension on the delivery system 10.

In some embodiments, proximal anchors 1022 may not be released from the system 10 until the distal anchors 1024 have captured the leaflets 108. In some embodiments, proximal anchors 1022 may be released from the system 10 prior to the distal anchors 1024 capturing the leaflets 108. In some embodiments, the proximal anchors 1022 can be released when the distal anchors 1024 are super or intra annular and the expanded prosthesis 1010 (either partially or fully expanded) can be translated through the mitral annulus 106. In some embodiments, the proximal anchors 1022 could be released when the distal anchors 1024 are sub-annular and the entire prosthesis 1010 can be pulled up into the left atrium 1078 such that the proximal anchors 1022 are supra-annular prior to release. In some embodiments, the proximal anchors 1022 could be intra-annular prior to release and the systolic pressure could push the prosthesis 1010 toward the atrium such that the proximal anchors 1022 end up supra-annular.

After, the leaflet capture and positioning of the prosthesis 1010 can be confirmed, along with the relatively perpendicular position with respect to the mitral annular plane. In some embodiments, the nosecone 28 can be withdrawn until it is within the prosthesis 1010. The mid shaft 50 can be further retracted until the prosthesis 1010 is released from the delivery system 10. Proper positioning of the prosthesis 1010 can be confirmed using TEE and fluoroscopic imaging.

Following, the delivery system 10 can be centralized within the prosthesis 1010. The nosecone 28 and delivery system 10 can then be retracted into the left atrium 1078 and removed.

This intra-super annulus release can have a number of advantages. For example, this allows the distal anchors 1024 to be properly aligned when contacting the chordae 110. If the distal anchors 1024 were released in the left ventricle 1080, this could cause misalignment or damage to heart tissue, such as the leaflets 108 or chordae 110.

Figure 17A:
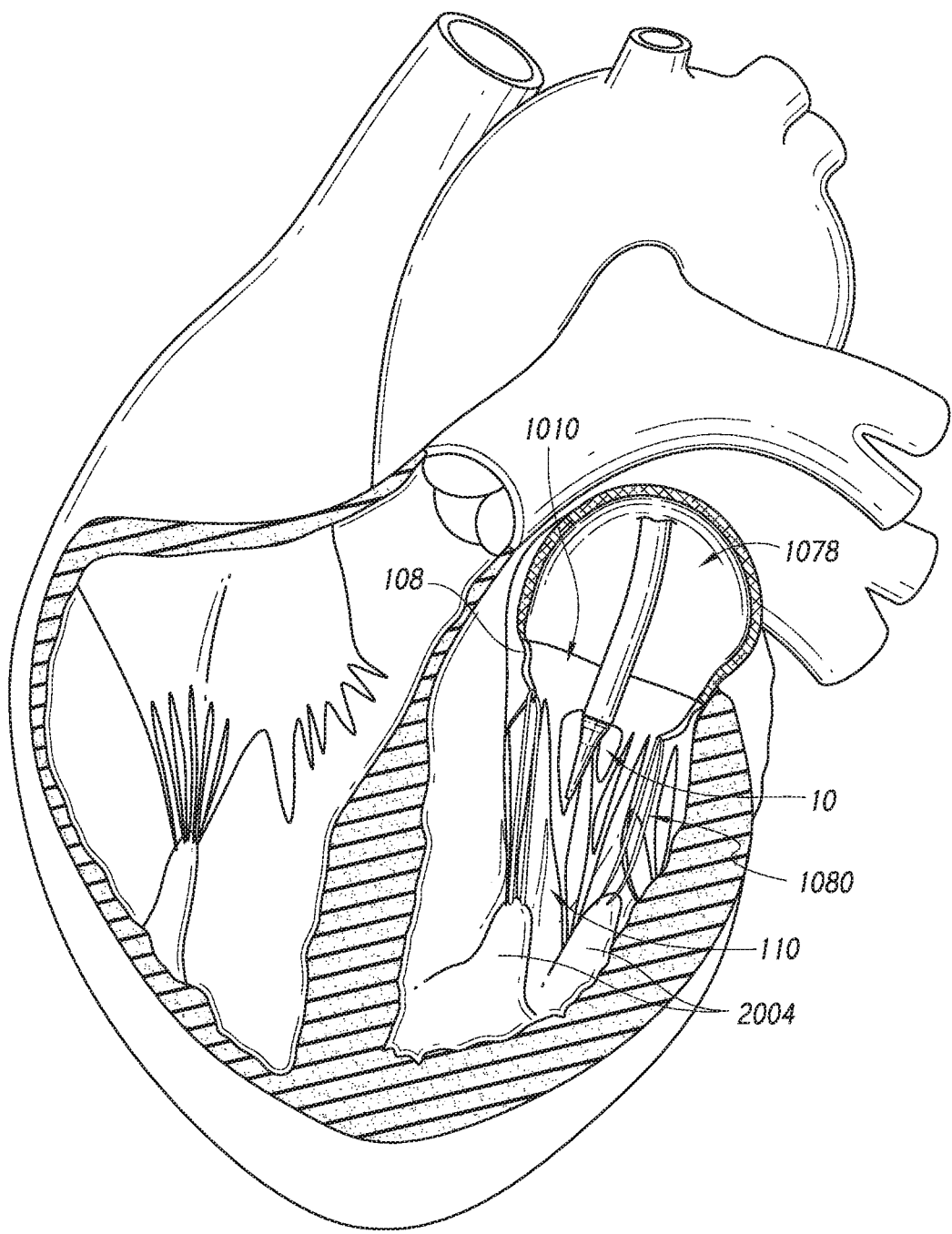
Figure 17B:
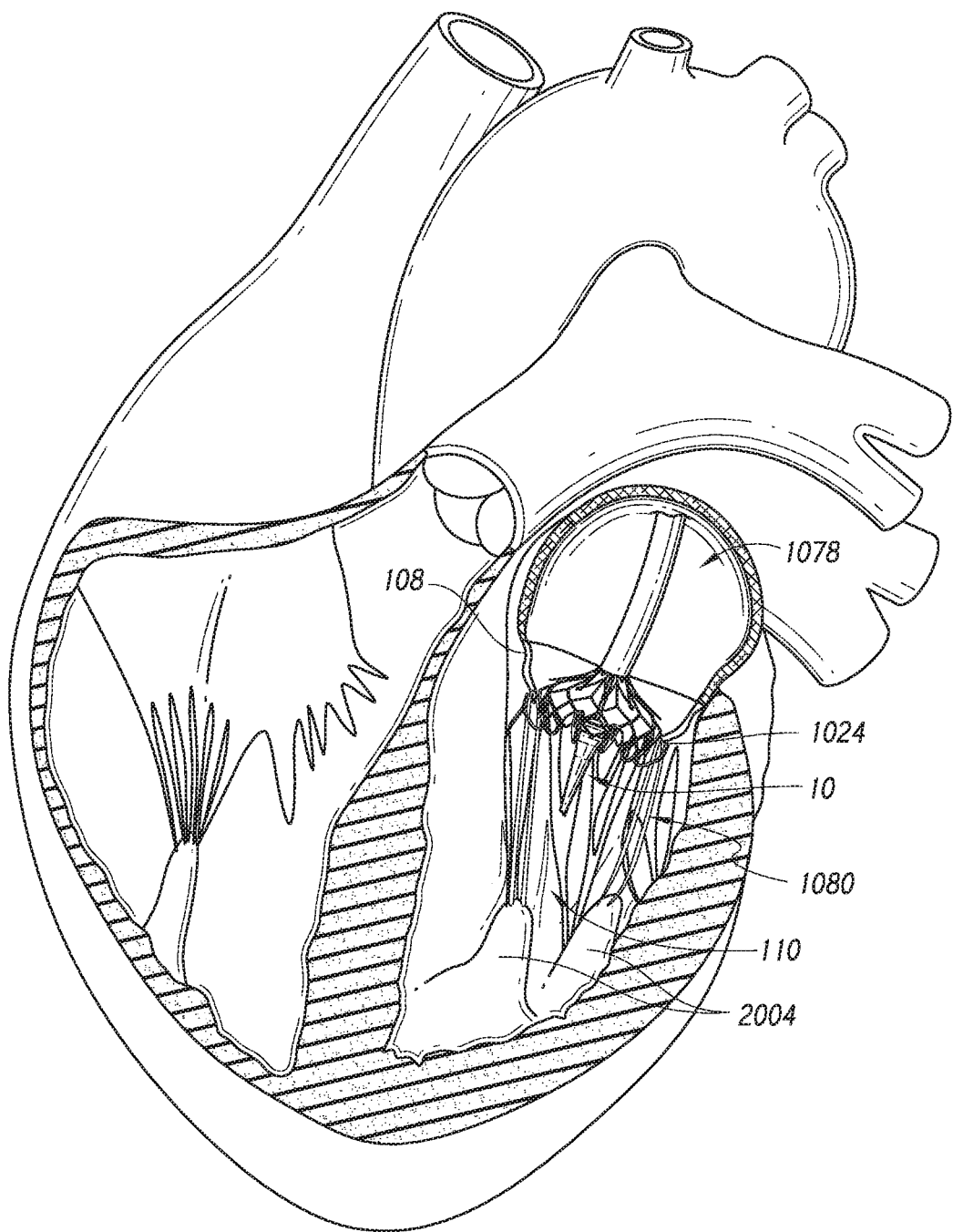

FIGS. 17A-B illustrate an alternate approach to releasing the prosthesis 1010. As shown in FIG. 17A, the delivery system 10 can be translated into the left ventricle 1080 prior to release of the prosthesis 1010. Thus, the distal end of the prosthesis 1010, and thus the distal anchors 1024, can be released and flipped partially, or fully within the left ventricle 1080 as shown in FIG. 17A. Accordingly, in some embodiments the anchors 1024 can be released/flipped below the mitral annulus 106, just below the mitral annulus 106, and/or below the free edges of the leaflets 108. Further, the anchors 1024 can be released above the papillary heads 2004. Similar methodology as discussed above can then be used to properly position the prosthesis 1010 and remove the delivery system 10 to deliver the prosthesis 1010 into the position shown in FIG. 16F. Further, in some embodiments the distal anchors 1024 can be released without expanding the prosthesis initially in the ventricle 1080, such as described above with respect to FIGS. 16A-B.

Transapical Delivery System

Figure 18:
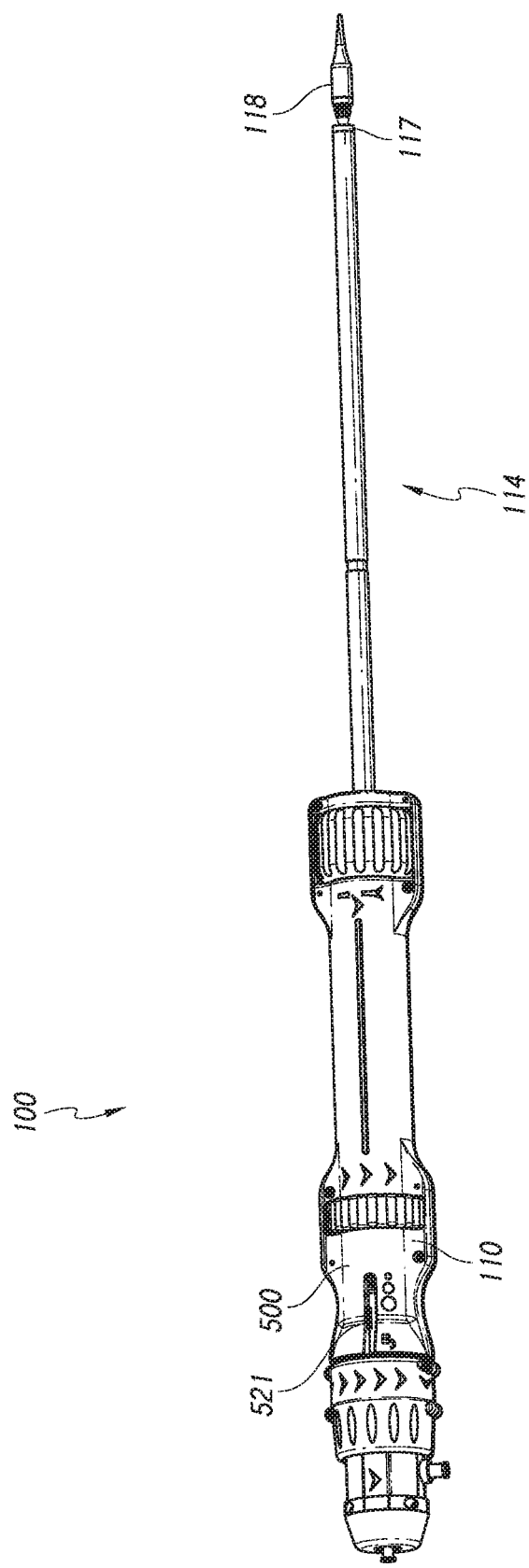
FIG. 18 illustrates an embodiment of a delivery device for a valve.

FIG. 18 illustrates an embodiment of a delivery device or system 100. The delivery system 100 can be used to deploy a prosthesis/implant, such as a replacement heart valve as described elsewhere in this specification, within the body. The delivery system 100 can receive and/or cover portions of the prosthesis such as a first end and second end of the implant. For example, the delivery system 100 may be used to deliver an expandable implant such as replacement mitral valve prosthesis 30 illustrated in FIG. 3, wherein the second end 303 is configured to be deployed or expanded before the first end 301. Replacement heart valves can be delivered to a patient's heart mitral valve annulus or other heart valve location in various ways, such as by open surgery, minimally-invasive surgery, and percutaneous or transcatheter delivery through the patient's vasculature. The delivery system 100 illustrated in FIG. 18 can be relatively short to more easily be used in an open heart procedure or other more direct procedures than the percutaneous procedure starting at the leg. At the same time, the delivery system 100 can still be relatively flexible to allow, for example, advancement through the pulmonary veins or the wall of the left atrium and then bending of the delivery device for proper placement at the mitral valve. In some embodiments, the delivery system 100 is particularly suitable for delivering a replacement heart valve to a mitral valve location through a transapical approach (e.g., through the apex of the heart).

With reference first to the embodiment illustrated in FIG. 18, the delivery system 100 can include a handle 110 and a plurality of sheaths and/or shafts such as the illustrated outer elongate hollow member shaft 114. As will be described in further detail below, the plurality of shafts can be sized and shaped to be slidable relative to each other. Accordingly, it should be understood that one or more of the plurality of shafts can be concentric with respect to another of the shafts to facilitate slidable movement of the shafts relative to each other. The plurality of shafts can be coupled to one or more other components of the delivery system 100. In some embodiments, the handle 110 can include a plurality of switches, levers, or other actuatable mechanisms which can be used to control the movement of the one or more shafts of the delivery system 100 and/or to control the operation of other components of the delivery system 100. A discussion of the handle 110 can be found below.

With continued reference to the embodiment of FIG. 18, the delivery system 100 can include an outer elongate hollow member such as the outer elongate hollow member shaft 114 having a proximal and distal end. As used to describe the components of the delivery system, "proximal" refers to a location of the component that is closer to the handle 110, and "distal" refers to a location of the component that is further from the handle 110. In some embodiments, the proximal end of the outer elongate hollow member shaft 114 can be coupled to the handle 110. In some embodiments, the outer elongate hollow member shaft 114 can be fixed relative to the handle 110. In some embodiments, the outer elongate hollow member shaft 114 can be movable relative to the handle 110. The outer elongate hollow member shaft 114 can include sheath and/or capsule, and may be made of one or multiple members. The outer elongate hollow member shaft 114 can have the same diameter from the proximal to distal end, or the diameter may vary. The outer elongate hollow member shaft 114 can be formed from a variety of materials, including ePTFE and PEEK, as well as other biocompatible materials. Further, the outer elongate hollow member shaft 114 can include a coating, such as a hydrophilic coating.

In some embodiments, the outer elongate hollow member shaft 114 can cover at least a portion of a collapsed or compressed implant 70 while the implant 70 is being delivered to the deployment site. For example, the outer elongate hollow member shaft 114 can cover at least the second end 303 of the implant 70 while the first end 301 of the implant 70 is received within a hollow nose cone 118, described further below. In some embodiments, the outer elongate hollow member shaft 114 can also cover the first end 301 of the implant 70. The outer elongate hollow member shaft 114 can be sized and shaped such that the outer elongate hollow member shaft 114 can retain the implant 70 in a compressed state as it is delivered to the deployment site. Accordingly, the outer elongate hollow member shaft 114 can function as a capsule for receiving the implant 70. As shown in the illustrated embodiment, the outer elongate hollow member shaft 114 can have a constant or substantially constant outer diameter throughout the entirety, or a substantial portion of the entirety, of its length. The outer elongate hollow member shaft 114 can be moveable relative to the nose cone 118 to uncover the second end 303 of the implant 70 while the first end 301 of the implant 70 remains engaged to an inner retention member (described below) within the nose cone 118 and remains covered by the nose cone 118.

The outer elongate hollow member shaft 114 can include a marker 117 positioned proximate the distal end, such as a radiopaque marker that allows for visualization by a physician. In some embodiments, the outer elongate hollow member shaft 114 can be formed of multiple layers of material, such that the outer elongate hollow member shaft 114 includes at least a first radial portion and a second radial portion. This can advantageously allow for the use of two types of material for the outer elongate hollow member shaft 114. For example, at least a portion of the first portion can be positioned radially outward from the second portion relative to a central longitudinal axis of the outer elongate hollow member shaft 114. The first portion, which may be considered an outer layer, can be formed from a relatively rigid material, such as PEBAX, ULTEM, PEAK and any other biocompatible material as desired. This can advantageously provide some degree of rigidity for the outer portion of the elongate hollow member shaft 114. The second portion, which may be considered an inner layer, can be formed from a more compliant material, such as PTFE, ePTFE and any other biocompatible material as desired. This can advantageously provide a more compliant inner surface for the outer elongate hollow member shaft 114, which can be beneficial when contacting other components of the delivery system 100 and the prosthesis. In some embodiments, the second portion can be a liner which is applied to the first portion.

While the outer elongate hollow member shaft 114 can be formed with multiple portions formed from multiple materials, it is also contemplated that the outer elongate hollow member shaft 114 can be formed from a single material.

Figure 21:
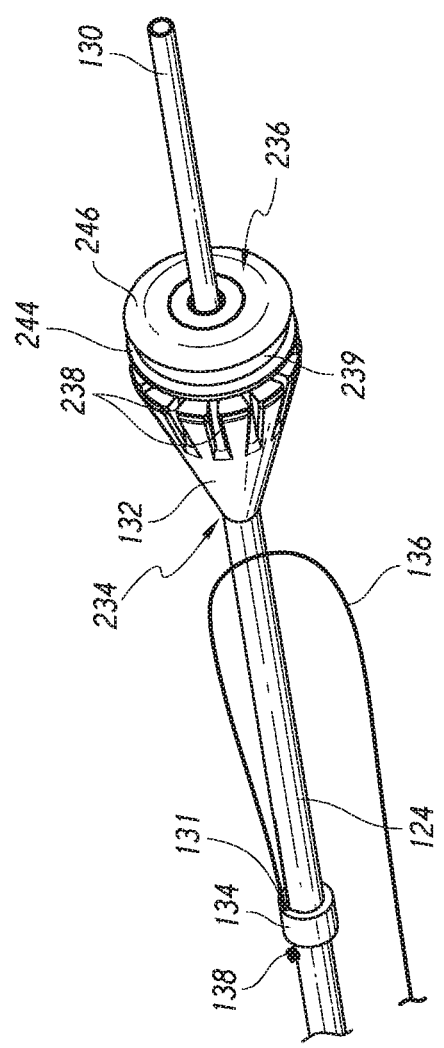
FIG. 21 illustrates a distal end of an embodiment of the delivery device of FIGS. 18-20 with the nosecone removed.

With reference now to FIGS. 19-21 (where FIGS. 19 and 21 illustrate delivery system 100 without the outer elongate hollow member shaft 114 being shown), the delivery system 100 can include, from radially inside to radially outside, a nose cone shaft 130, an inner retention shaft 124 provided concentrically over the nose cone shaft 130, and a locking shaft 122 provided concentrically over the inner retention shaft 124. Each of the shafts can move axially with relation to one another, and in some embodiments, some of these shafts may be moved together. In FIGS. 19 and 21, it will be noted that the locking shaft 122 has been withdrawn proximally for convenience of viewing portions of the inner retention shaft 124, while in FIG. 20, the locking shaft 122 is illustrated as being advanced more distally along the inner retention shaft 124. FIG. 21 as illustrated has the nose cone 118 removed.

The nose cone shaft 130 has a proximal end operably connected to the handle 110 and a distal end coupled to nose cone 118. The nose cone shaft 130 may be hollow along its length to receive a guide wire. Nose cone 118 comprises an elongate, hollow portion 119 with a proximally facing opening 121, and a tapered distal portion 123 (as shown in FIG. 20). The nose cone shaft 130 may be coupled to the nose cone 118 at a distal end of the elongate, hollow portion 119, such that the nose cone shaft 130 extends through the proximal opening 121 and ends at the intersection 125 between the elongate, hollow portion 119 and the tapered distal portion 123 at nose cone lock 129. The nose cone 118 can further contain a lumen 127 extending from the distal end of the nose cone shaft 130 to the distal end of the nose cone 118, which can allow a guide wire to pass through. The nose cone 118 can be formed from a relatively rigid, high durometer material. The nose cone 118, including both the elongate, hollow portion and the tapered, distal portion, can have a length, measured from the distalmost end to a proximalmost end, of between approximately 5 mm to 50 mm, between approximately 10 mm to approximately 40 mm, between approximately 15 mm to approximately 25 mm, approximately 20 mm, any other lengths within these ranges, and any other lengths as desired.

As shown in FIGS. 19 and 20, the tapered distal portion can have a concave outer surface thereby forming a more defined distal tip of the nose cone 118. As shown more clearly in the cross-section of FIG. 20, the nose cone 118 can include an outer portion 219 and a nose cone insert 220, the nose cone insert 220 being generally tubular in shape and forming a cavity within the nose cone 118 and the outer portion 219 forming the general shape of the nose cone 118 and extending from the proximal to the distal portion of the nose cone 118. The nose cone insert 220 may only be located in the proximal portion of the nose cone 118. This can advantageously allow for the use of two types of material for the nose cone 118. For example, as shown in the illustrated embodiment, at least a portion of the outer portion 219 can be positioned radially outward from the nose cone insert 220 relative to a central longitudinal axis of the nose cone 118. The outer portion 219 can be formed from a lower durometer material such as urethane, PEBAX, polysilicone and any other biocompatible material as desired. The nose cone insert 220 can be formed from higher durometer materials such as stainless steels, titanium, and any other biocompatible material as desired. This can advantageously provide additional structural support for the nose cone 118. The nose cone insert 220 can have an inner diameter of about 0.2, 0.25, 0.3, 0.343, 0.35, or 0.4 inches and a length of about 0.6, 0.65, 0.7, 0.709, 0.75, or 0.8 inches. The nose cone insert 220 can have an inner diameter of greater than about 0.2, 0.25, 0.3, 0.343, 0.35, or 0.4 inches and a length of greater than about 0.6, 0.65, 0.7, 0.709, 0.75, or 0.8 inches. The nose cone insert 220 can have an inner diameter of less than about 0.2, 0.25, 0.3, 0.343, 0.35, or 0.4 inches and a length of less than about 0.6, 0.65, 0.7, 0.709, 0.75, or 0.8 inches. In some embodiments, the nose cone insert 220 can include threading for attachment to a shaft, such as nose cone shaft 130. The threading can be located towards the distal end of the nose cone 118, and can be a separate piece such as nose cone lock 129. In some embodiments, the outer portion 219 can be overmolded onto the nose cone insert 220 and/or attached using mechanical fasteners such as screws, bolts, rivets, and threaded couplings, chemical fasteners, such as adhesives, or other types of fastening techniques such as welding. In some embodiments, the nose cone 118 can be a single unit formed from a single material. Further, the nose cone 118 can be flexible and self-dilating.

With reference particularly to the cross-sectional view of FIG. 20, the outermost diameter of the nose cone 118, such as the outer diameter of the elongate, hollow portion 119, can be similar to, or equal to, the outer diameter of an outer shaft and/or outer component, such as the outer elongate hollow member shaft 114. As shown in the illustrated embodiment, the elongate, hollow portion 119 has an outer diameter which is similar to that of the outer elongate hollow member shaft 114. This can form a generally smooth transition in diameter between the nose cone 118 and the outer shaft and/or outer component if and when the nose cone 118 is brought into contact with the outer shaft and/or the outer component. In some embodiments, the elongate, hollow portion 119 of the nose cone 118 can have an outer diameter of approximately 31 Fr or 32 Fr and the outer shaft and/or outer component can have an outer diameter of approximately 31 Fr or 32 Fr.

In some embodiments, the outer diameter of the nose cone 118, such as the elongate, hollow portion 119, can be similar to, or equal to, the inner diameter of the outer elongate hollow member shaft 114 such that nose cone 118 can be partially received within the outer elongate hollow member shaft 114. In some embodiments, the elongate, hollow portion of the nose cone 118 can have an outer diameter of approximately 30 Fr and the outer shaft and/or outer component can have an inner diameter of approximately 30 Fr. In some embodiments, the outer shaft can be an outermost shaft of the delivery system.

With continued reference to the embodiment of FIGS. 19-21, the inner retention shaft 124 is slidable over the nose cone shaft 130, such that the nose cone shaft 130 can be moved within the inner retention shaft 124 and the inner retention shaft 124 can be moved over the nose cone shaft 130. The distal end of the inner retention shaft 124 can be coupled to at least a portion of an inner retention member 132 that can be positioned within and be removed from the proximally-facing opening of the nose cone 118. The inner retention member 132 can be attached to the inner retention shaft 124 with threading 135 (shown in FIG. 20). Further, the inner retention member 132 can have an elongated and proximally tapered design. The inner retention member 132 can be formed of a single material, or a plurality of different materials.

Further, as shown in FIG. 19, the inner retention member 132 can have a proximal end 234 and a distal end 236 with a plurality of slots 238 sized and shaped to receive portions of a first end 301 of the implant 70 positioned proximate the proximal end 234. For example, the inner retention member 132 may comprise a ring surrounding the inner retention shaft 124 with slots 238 configured to receive longitudinally-extending struts 72 on the implant 70 that are located just distal to enlarged, mushroom-shaped locking tabs 74 (shown in FIG. 3). Slots 238 can be circumferentially-spaced from each other extend along a longitudinal axis of the inner retention member 232. In some embodiments, the inner retention member 132 can include a cavity 239 positioned distal the slots 238. The cavity 239 can be sized and shaped to receive portions of the first end 301 of the implant 70, such as the locking tabs 74. As shown in the illustrated embodiment, the cavity 239 can have an annular shape or may be considered to extend circumferentially around the inner retention member 132. In some embodiments, the inner retention member 132 can include a taper towards the proximal end 234. This can facilitate removal of the inner retention member 132 from the heart by reducing the diameter at the proximalmost end of the inner retention member 132 and reducing the likelihood of snagging on tissue.

Figure 22:
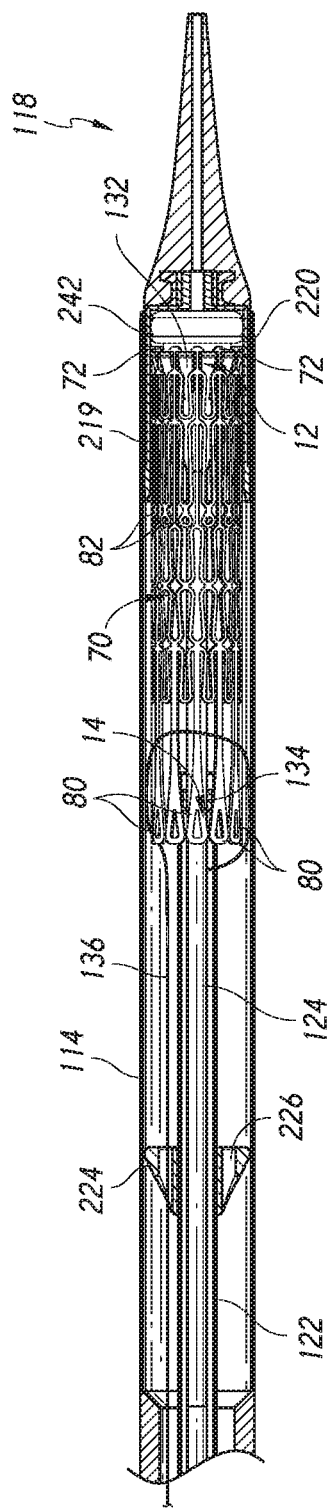
FIG. 22 illustrates a cross section of an embodiment of the delivery device including the replacement valve of FIG. 21.

The inner retention shaft 124 can cooperate with the inner retention member 132 and the nose cone 118 to release a first end of the prosthesis from the nose cone 118. As shown in FIG. 22, the first end 12 of the implant 70 can be placed in a compressed state such that the first end 301 of the implant 70 is retained between the inner retention member 132 and the nose cone 118 when the inner retention member 132 is received within and covered by the nose cone 118. Proximal movement of the inner retention shaft 124 with respect to the nose cone 118 can result in proximal movement of the inner retention member 132 relative to the nose cone 118 which can release the first end 301 of the prosthesis 30 from the nose cone 118. Similarly, distal movement of the nose cone 118 relative to the inner retention shaft 124, and thus the inner retention member 132, can also release the first end 301 of the prosthesis 30 from the nose cone 118. If the implant 70 is not covered by the outer elongate hollow member shaft 114, once the inner retention shaft 124 is moved relative to the nose cone 118 to uncover the first end 301 of the implant 70, the first end 301 of the implant 70 may self-expand from its compressed state to an expanded configuration.

Further, the inner retention member 132 can include a circumferential cavity proximate the distal end 236. The cavity can be formed between one or more radially extending protrusions, such as ridges 244, 246, illustrated in FIG. 20. As shown in the illustrated embodiment of FIGS. 19 and 20, the cavity can have an annular shape. A compressible member 242, such as an O-ring, can be received at least partially within the cavity 240 as shown in FIG. 20. The compressible member 242 can act as a seal between the inner retention member 132 and the nose cone 118 to keep the components together during retraction and allow for smooth sheathing into the outer elongate hollow member shaft 114. Moreover, the compressible member 242 can ensure that there is no gap between the nose cone 118 and the inner retention member 132 to prevent a portion of the implant 70 from being caught during removal of the nose cone 118 and inner retention member 132. Further, the compressible member 242 can keep the nose cone 118 from coming into contact with the inner retention member 132.

Further, the inner retention shaft 124 can include a tether retention member 134 proximal to the inner retention member 132. As shown in the illustrated embodiment of FIG. 21, the tether retention member 134 can be a C-lock mounted on the inner retention shaft 124 having a longitudinal opening or slot 131 through which a tether or lasso 136, such as a nitinol wire having a suture crimped on the end, can pass. In order to retain the tether 136 within the tether retention member 134, the end 138 of the tether 136 can be sized and shaped such that the end 138 is prevented from passing distally through the opening of the tether retention member 134 when the end 138 is located proximal to the opening.

For example, the end 138 of the tether 136 can be knotted such that at least one dimension of the end 138 prevents the end 138 from passing distally through the opening. The locking shaft 122, described below, will further restrain the tether 136 from moving radially outwards through the slot in the tether retention member 134 and thus the locking shaft 122 and tether retention member 134 cooperate to releasably engage the tether 136.

In the illustrated embodiment, provided over the inner retention shaft 124 is a locking shaft 122. In some embodiments, inner retention shaft 124 can be sized and shaped such that inner retention shaft 124 is slidable within the locking shaft 122. For example, in some embodiments, the inner retention shaft 124 can be moved within the locking shaft 122. In some embodiments, the locking shaft 122 can be moved over the inner retention shaft 124. As shown in FIGS. 19 and 20, the locking shaft 122 may slide over the inner retention shaft 124 and cover the tether retention member 134. The locking shaft 122 can cooperate with the tether retention member 134 to retain a tether, or lasso, 136 (shown in FIG. 21) attached to an implant 70 until the locking shaft 122 is translated proximally to release the tether 136. Moreover, locking shaft 122 can be sized and shaped such that the outer elongate hollow member shaft 114 is slidable over the locking shaft 122.

When the tether 136 is positioned in the tether retention member 134, the tether 136 can be released by translating the locking shaft 122 proximally. Thus, a radially outwards tension force will pull the end 138 of the tether 136 out of the tether retention member 134. The tether 136 can be tensioned and angled such that the tether 136 would pass over the tether retention member 134 when tether retention member 134 is uncovered from the locking shaft 122. It should be understood that other mechanisms can be used for tether retention assembly in lieu of the lock and tether retention member 134 including, but not limited to, clamps which engage the tether 136. As shown in FIG. 22, the tether 136 can engage at least a portion of the prosthesis, such as the second end 303 of the implant 70. For example, in some embodiments, the tether 136 can extend distally from the tether retention member 134, wrap around at least some portion of the implant 70 when the implant is compressed within outer elongate hollow member shaft 114 and nose cone 118, and extend at least proximally through the outer elongate hollow member shaft 114. The end opposite end 138 can be attached to a component of the delivery system 100 such that the tether 136 can be retracted into the delivery system 100 upon release of the tether 136 from the tether retention assembly 128.

In some embodiments such as that illustrated in FIG. 20, the locking shaft 122 can include a centering ring/radial protrusion 224, such as an annular and/or tapered disc, positioned proximal to its distal end. The centering ring 224 can assist in maintaining the locking shaft 122 in a desired radial alignment relative to the shaft within which the locking shaft 122 is positioned (e.g., the outer elongate hollow member shaft 114). For example, as shown in the illustrated embodiment, the centering ring 224 can assist in maintaining concentricity between the locking shaft 122 and another shaft such as the outer elongate hollow member shaft 114. The centering ring 224 can be tapered on its proximal end, as shown, for ease of the centering ring 224 entering the outer elongate hollow member shaft 114 during retrieval of the system 100. In some embodiments, the centering ring 224 can include a plurality of apertures/guide members 226 positioned circumferentially around the locking shaft 122 and circumferentially spaced from one another for the tether, wire or suture 136 to pass through. Any one of the guide members 226 can be used for the tether 136 as is convenient for a user. As shown in the illustrated embodiment, each guide member 226 can be formed as a hole or aperture on the centering ring 224.

The embodiments of FIGS. 22-27 illustrates steps of a method of operating the delivery system 100 and releasing an intralumenal frame assembly, such as implant 70, to intralumenal tissue at an in situ target location. The steps of this method can be carried out while the implant is in a radially compacted state within the outer elongate hollow member shaft 114. In some embodiments, the longitudinal axis of the implant 70, which runs between the first 301 and second ends 303 of the implant 70, can be parallel to and/or concentric with the longitudinal axis of one or more shafts of the delivery system 100. The steps of this method can be used to transapically deliver a replacement heart valve to a mitral valve location.

FIG. 22 shows a cross section of the delivery system 100 with the implant 70 located in the delivery position. For ease of illustration, the implant 70 is shown in FIG. 22 with only its metal frame illustrated. As shown, the outer elongate hollow member shaft 114 covers the implant 70, thus preventing expansion of the implant 70, in particular the second end 303. Further, the ventricular anchors 80 of the implant extend proximally toward the handle 110, with the outer elongate hollow member shaft 114 radially restraining the ventricular anchors 80 pointing proximally. The outer elongate hollow member shaft 114 extends distally to the nose cone 118, which covers the inner retention member 134. The first end 301 of the implant 70 is positioned within the inner retention member 134, with struts 72 located within the slots of the inner retention member 134 and covered by the nose cone 118. Further, the tether 136 extends distally from the handle 110, within the outer elongate hollow member shaft 114, through one of the guide members 226, and is wrapped around the implant, more preferably wrapping around the ventricular anchors 80 that extend proximally. The tether 136 then extends proximally to the tether retention member 134 located within the locking shaft 122, where the end of the tether 136 is locked in position as described above.

Figure 23:
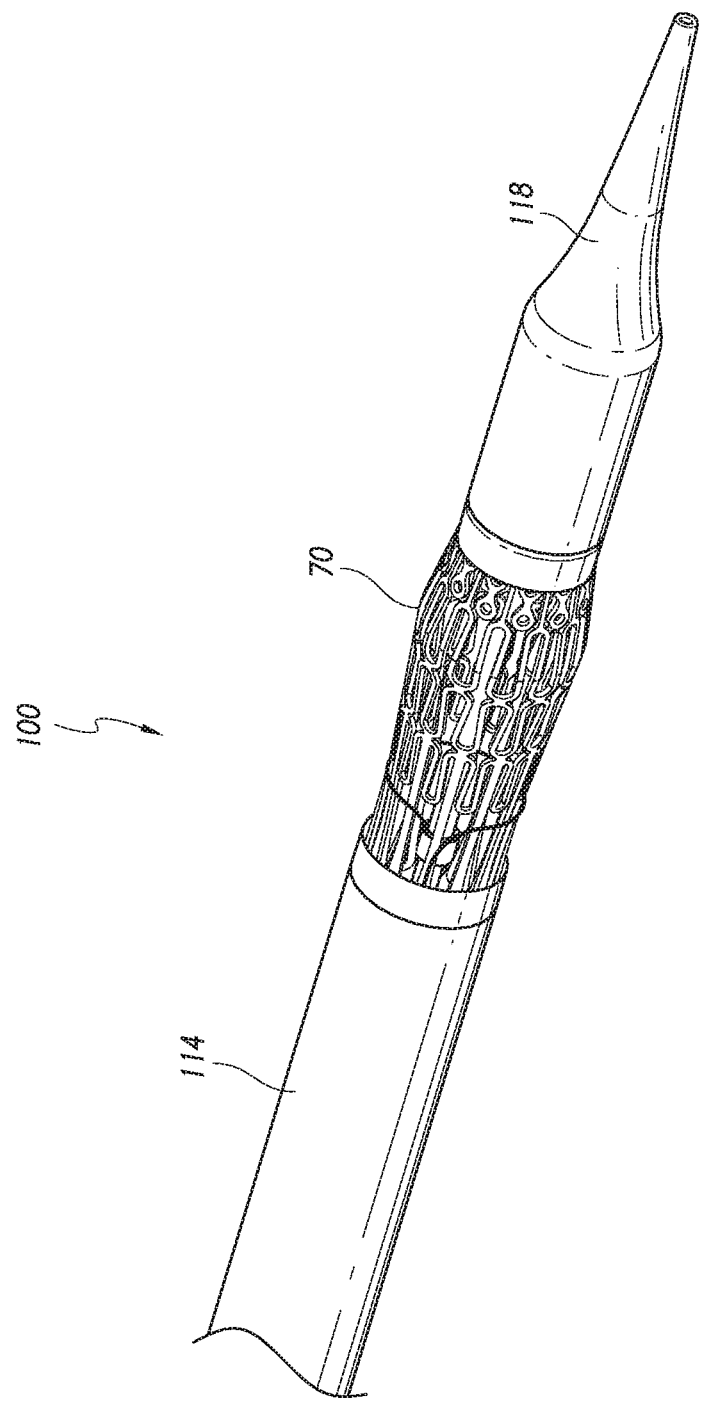
FIGS. 23-27 illustrate an embodiment of an implantation procedure of a replacement valve using the delivery device.

With reference next to the step of FIG. 23, once the delivery system 100 has positioned the implant at the in situ target location, the outer elongate hollow member shaft 114 can be moved relatively away from the nose cone 118, either by proximally retracting the outer elongate hollow member shaft 114 and/or distally advancing the nose cone 118, nose cone shaft 130, inner retention shaft 124, and inner retention member 132, to uncover at least a portion of the implant 70, in particular the second end 303 of the implant 70. As shown in FIG. 23, there may be a slight bulge in the implant 70 during this phase.

Figure 24:
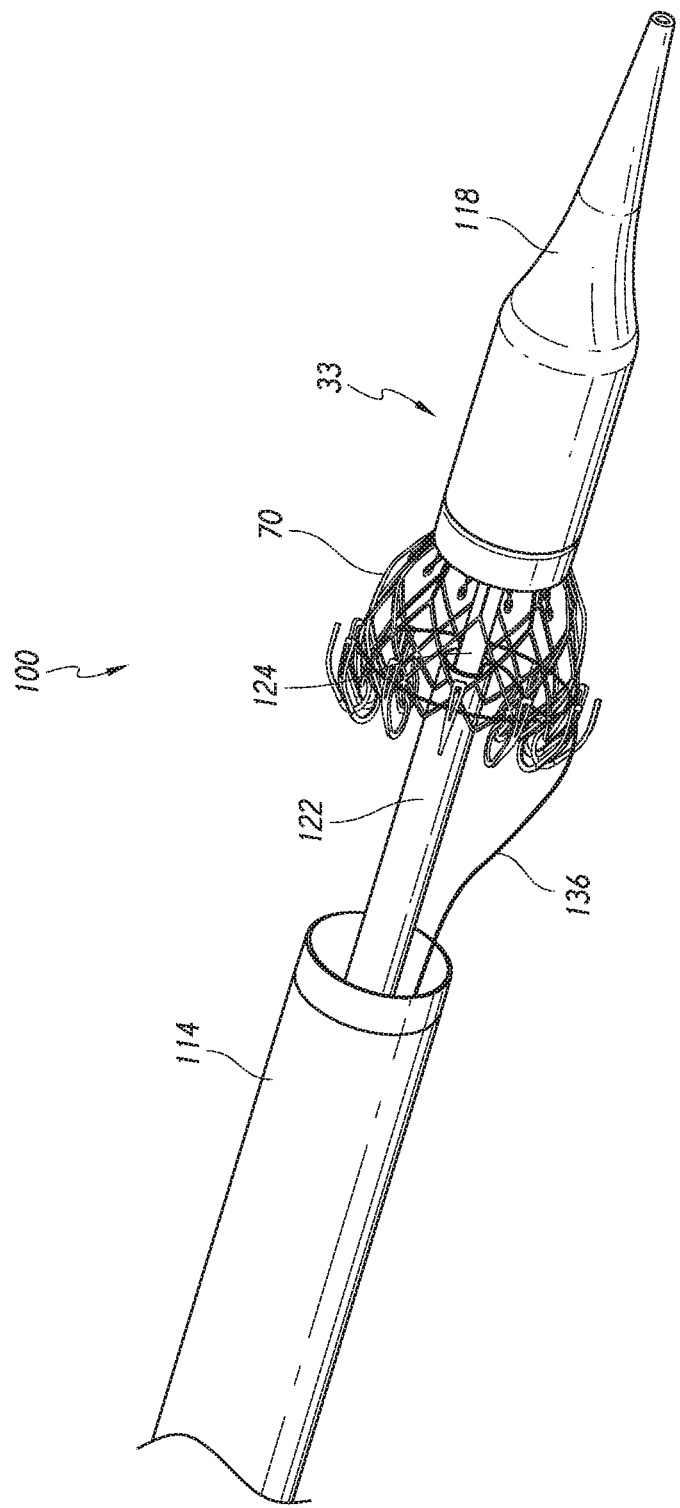

With reference next to the step of FIG. 24, the outer elongate hollow member shaft 114 can be further moved relatively away from the nose cone 118 to further uncover the implant 70. As shown in the illustrated embodiment, the second end of the implant 70 has been uncovered with the tether 136 being the only component restraining the radial dimension of the frame of the implant 70. By maintaining tension on the tether 136, the tether 136 can continue to at least partially restrain the radial dimension of the second end and can advantageously reduce the speed at which the second end radially expands. The tether 136 can be continuously released by the user at the handle 110 until the second end 303 of the implant 70 is fully expanded. In some embodiments, the tether 136 can be configured such that the first end 301 remains in the fully compacted state when the second end 303 is fully uncovered.

It should be noted that the first end 301 of the implant 70 can remain covered by the nose cone 118 during this step such that the first end 301 remains in a radially compacted state. Moreover, as shown in the illustrated embodiment, the second end 303 of the implant 70 has at least partially expanded in the radial dimension with the ventricular anchors 80 having been flipped to extend distally away from the second end of the implant 70 (and distally away from the handle 110). By controlling the expansion of the second end 303 of the implant 70 with the tether 136, the user can minimize the risk of the ventricular anchors 80 catching on surrounding tissue when the ventricular anchors 80 flip from extending proximally to extending distally.

Figure 25:
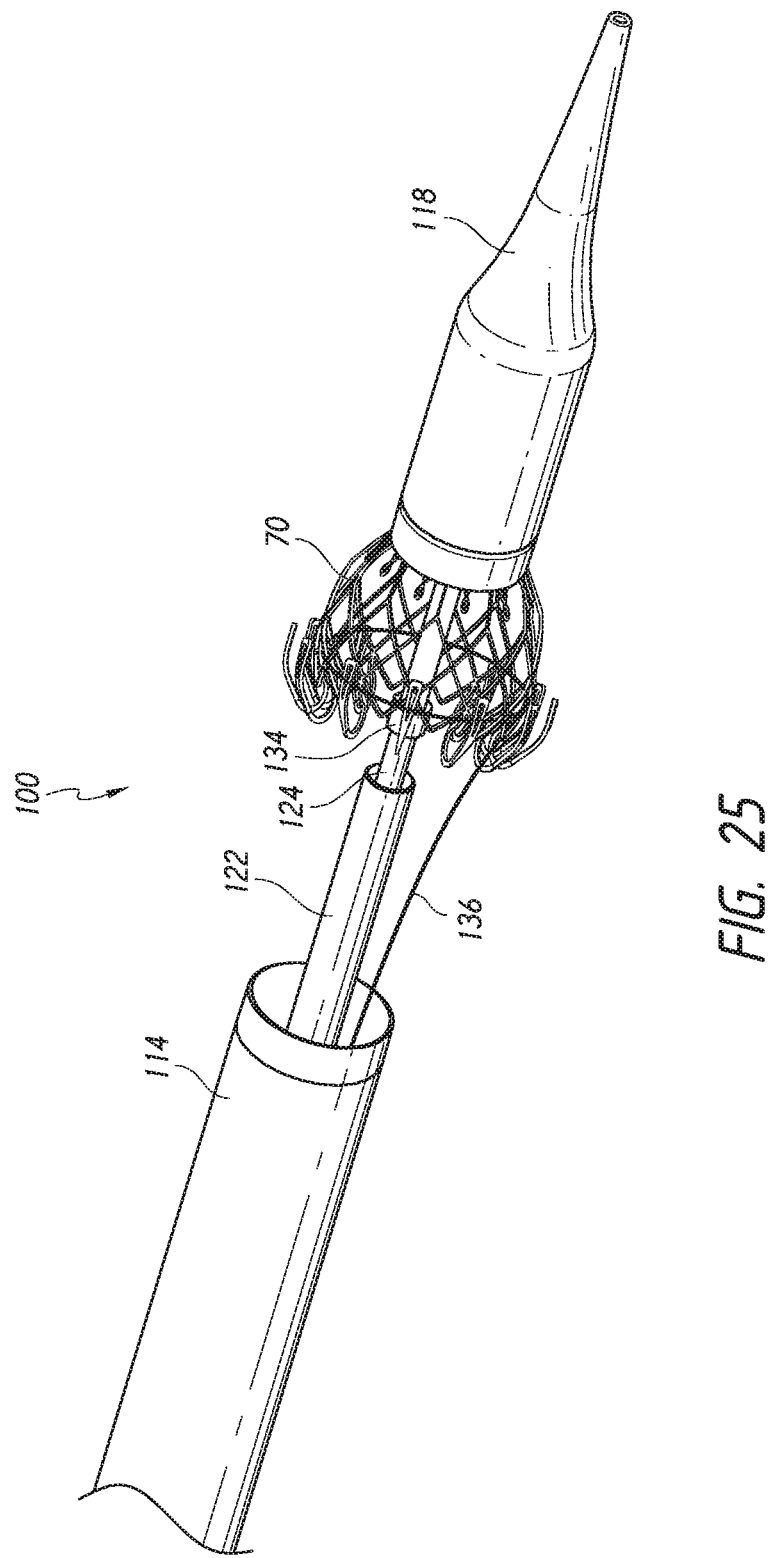

As shown in FIG. 25, once the second end 303 of the implant 70 is fully expanded, the locking shaft 122 can be moved relatively proximally to expose the tether retention member 134, thus allowing the tether 136 to fully release from the tether retention member 134.

Figure 26:
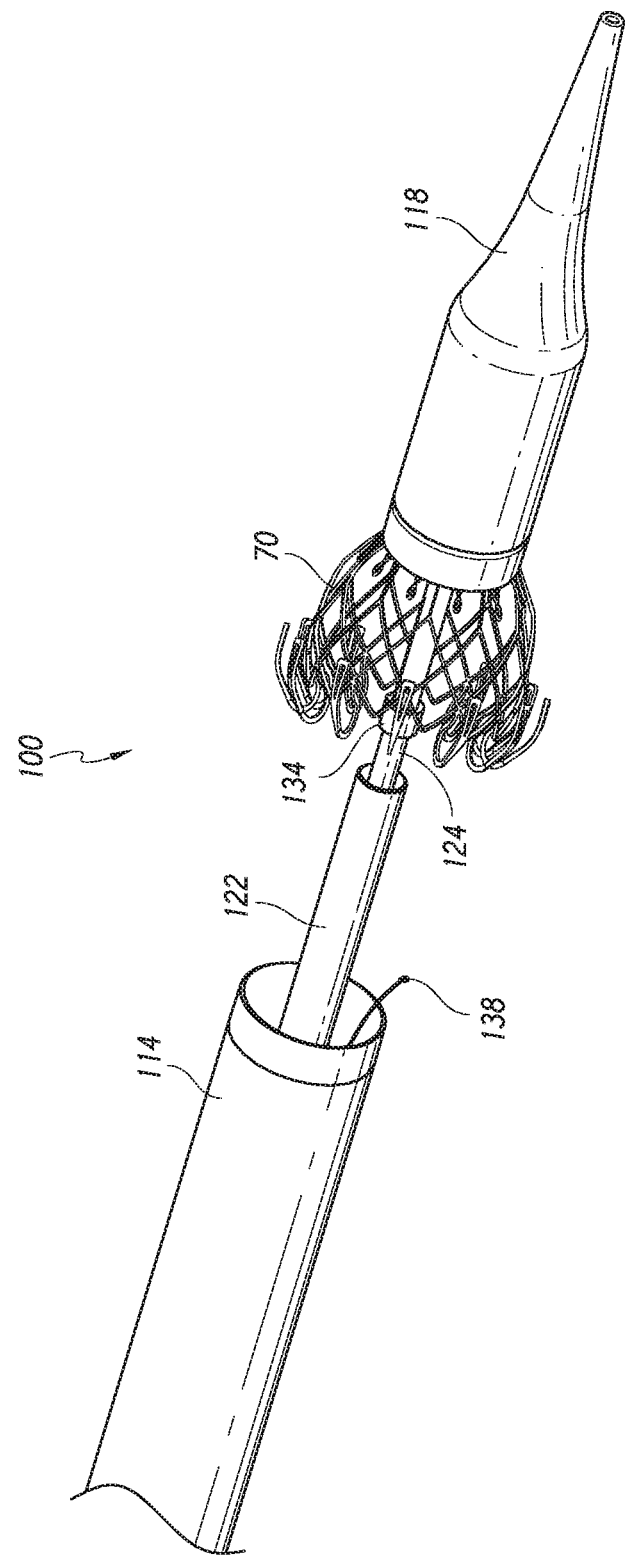

Next, as shown in FIG. 26, the tether retention member 134 has released the end 138 of the tether 136. It should be noted that the first end of the implant 70 can remain covered by the nose cone 118 during this step such that the first end remains in a radially compacted state. As discussed below, the tether 136 and end 138 can be retracted proximally into the delivery system 100 at this point.

Figure 27:
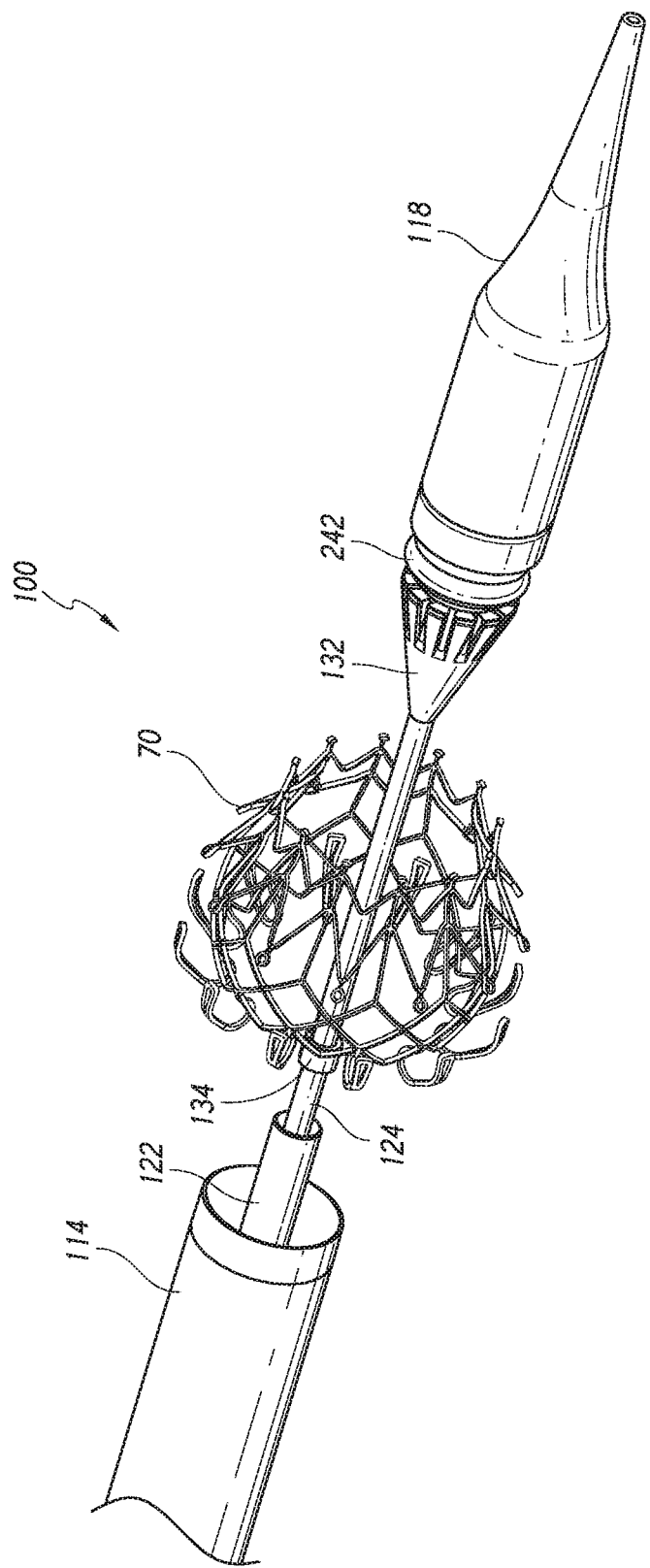

With reference next to the step of FIG. 27, the inner retention member 132 can be moved relatively away from the nose cone 118 such that the first end of the implant 70 can radially expand to its fully expanded configuration. This can be achieved by either distally moving the nose cone 118 relative to the inner retention member 132 and/or moving the inner retention member 132 proximally relative to the nose cone 118. After expansion and release of the implant 70, the inner retention member 132 and the nose cone 118 can be withdrawn through the center of the implant 70 and into the outer elongate hollow member shaft 114. Advantageously, as shown and discussed above, the inner retention member 132 can be tapered on the proximal end in order to more easily slide into the outer elongate hollow member shaft 114. Prior to withdrawing, the nose cone shaft 130 can be translated proximally to abut again the distal end of the inner retention member 132, which provides a tapered surface for the nose cone 118 to enter the outer elongate hollow member shaft 114 as well. In some embodiments, the locking shaft 122, the inner retention shaft 124 and the nose cone shaft 130 are moved proximally together so that the inner retention member 132 enters the outer elongate hollow member shaft 114 and the nose cone 118 abuts the distal end of the outer elongate hollow member shaft 114, and then the delivery system 100 is removed from the patient The delivery system 100 may be provided to users with an implant 70 preinstalled, such as illustrated in FIG. 22. In other embodiments, the implant 70 can be loaded onto the delivery device 100 shortly before use, such as by a physician or nurse.

Insertion Methodology

Figure 28:
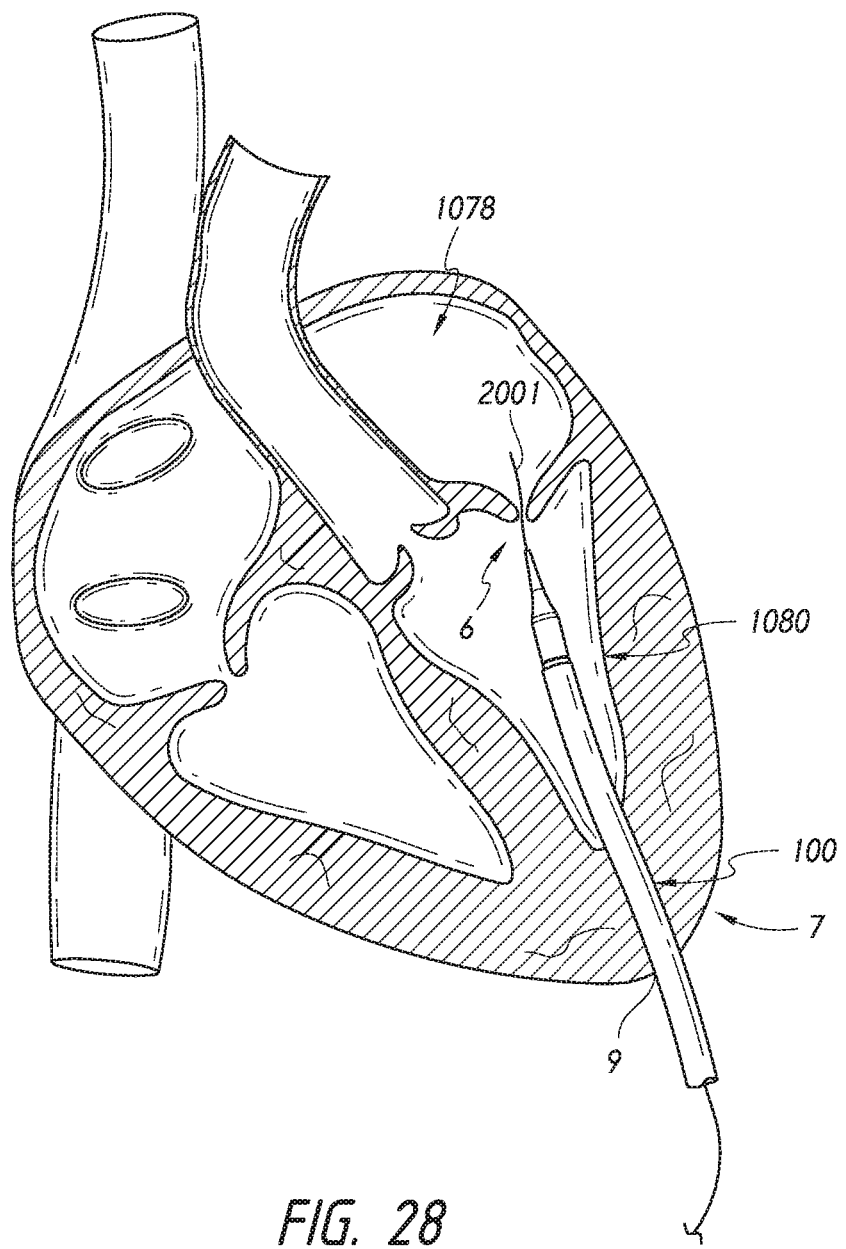
FIG. 28 illustrates a transapical approach for a delivery device.
Figure 29:
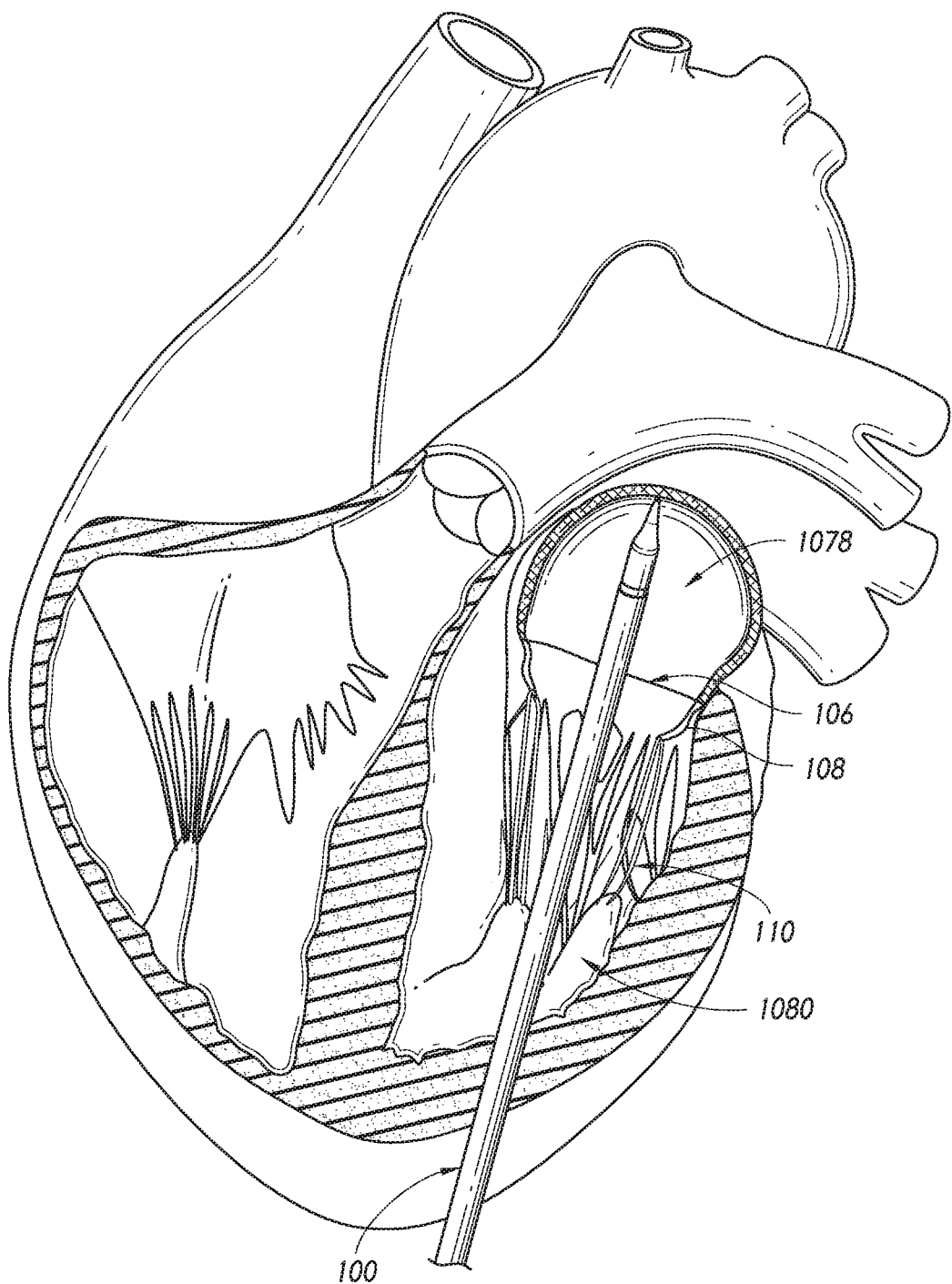
FIGS. 29-31B illustrate steps of a transapical method for delivery of a valve prosthesis to replace a mitral valve.

FIG. 28 illustrates a transapical approach for use with the delivery device 100. As shown, the delivery device 100 can access a mitral valve through the apex 7 of the heart. As depicted in FIG. 28, a guide wire 2001 is advanced into the left ventricle 6 of the heart through a puncture or opening 9 near the apex 7. The heart may be accessed through a limited thoracotomy, small trocar puncture, or small catheter puncture. With the guide wire 2001 in place, the physician can insert the device 100 to the left ventricle 6 and deploy the heart valve as disclosed above. In some embodiments, a guide wire is not used. FIG. 8, discussed above, illustrates a schematic representation of the position of the implant 70 as a replacement mitral valve. A balloon can be inserted into the left atrium 1078 and expanded to confirm that the guide wire 2001 has not been advanced through any of the chordae 110 or papillary muscles.

In some embodiments, the implant 70 can be delivered under fluoroscopy so that a user can view certain reference points for proper positioning of the implant 70. Further, echocardiography can be used for proper positioning of the implant 70.

FIGS. 29-31B show different steps of embodiments of a method of delivering the implant 70 to the proper position in the heart.

Prior to insertion of the delivery system 100, the access site into the patient can be dilated. Further, a dilator can be flushed with, for example, heparinized saline prior to use. The delivery system 100 can then be inserted over a guide wire 2001.

The delivery system 100 can be advanced until a distal end of the delivery system 10 through the left ventricle 1070 and mitral annulus 106 into the left atrium 1078. Thus, the distal end of the delivery system 100 can be located in the left atrium 1078 as shown in FIG. 19. In some embodiments, the delivery system 100 can be rotated, such as under fluoroscopy, into a desired position. The position of the delivery system 100, and the implant 70 inside, can be verified using echocardiography and fluoroscopic guidance.

In some embodiments, the implant 70 can be located, prior to release, above the mitral annulus 106, in line with the mitral annulus 106, just below the mitral annulus 106, or below the mitral annulus 106. In some embodiments, the implant 70 can be located, prior to expansion, fully above the mitral annulus 106, in line with the mitral annulus 106, just below the mitral annulus 106, or fully below the mitral annulus 106. In some embodiments, the implant 70 can be located, prior to expansion, partially above the mitral annulus 106, in line with the mitral annulus 106, or partially below the mitral annulus 106.

In some embodiments, the position of the mitral plane and the height of any papillary muscles 2004 on the fluoroscopy monitor can be marked to indicate an example target landing zone.

Further, the delivery system 100 can be positioned to be coaxial to the mitral annulus 106, or at least as much as possible, while still reducing contact with the left ventricular wall, the left atrial wall, and/or the mitral annulus 106 and reducing delivery system tension. An echo probe can be position to view the anterior mitral leaflet (AML), the posterior mitral leaflet (PML) (leaflets 108), mitral annulus 106, and outflow tract. Using fluoroscopy and echo imaging, the implant 70 can be confirmed to be positioned at a particular depth and desired alignment (e.g., coaxial alignment) with the mitral annulus 106.

Afterwards the implant 70 is aligned to be generally perpendicular to the mitral annulus 106, the elongate hollow member shaft 114 can be retracted to expose the left ventricular anchors 80. In some embodiments, once exposed, the elongate hollow member shaft 114 can be reversed in direction to relieve tension on the elongate hollow member shaft 114. The tether 136 can keep the implant 70 from quickly expanding.

Figure 30A:
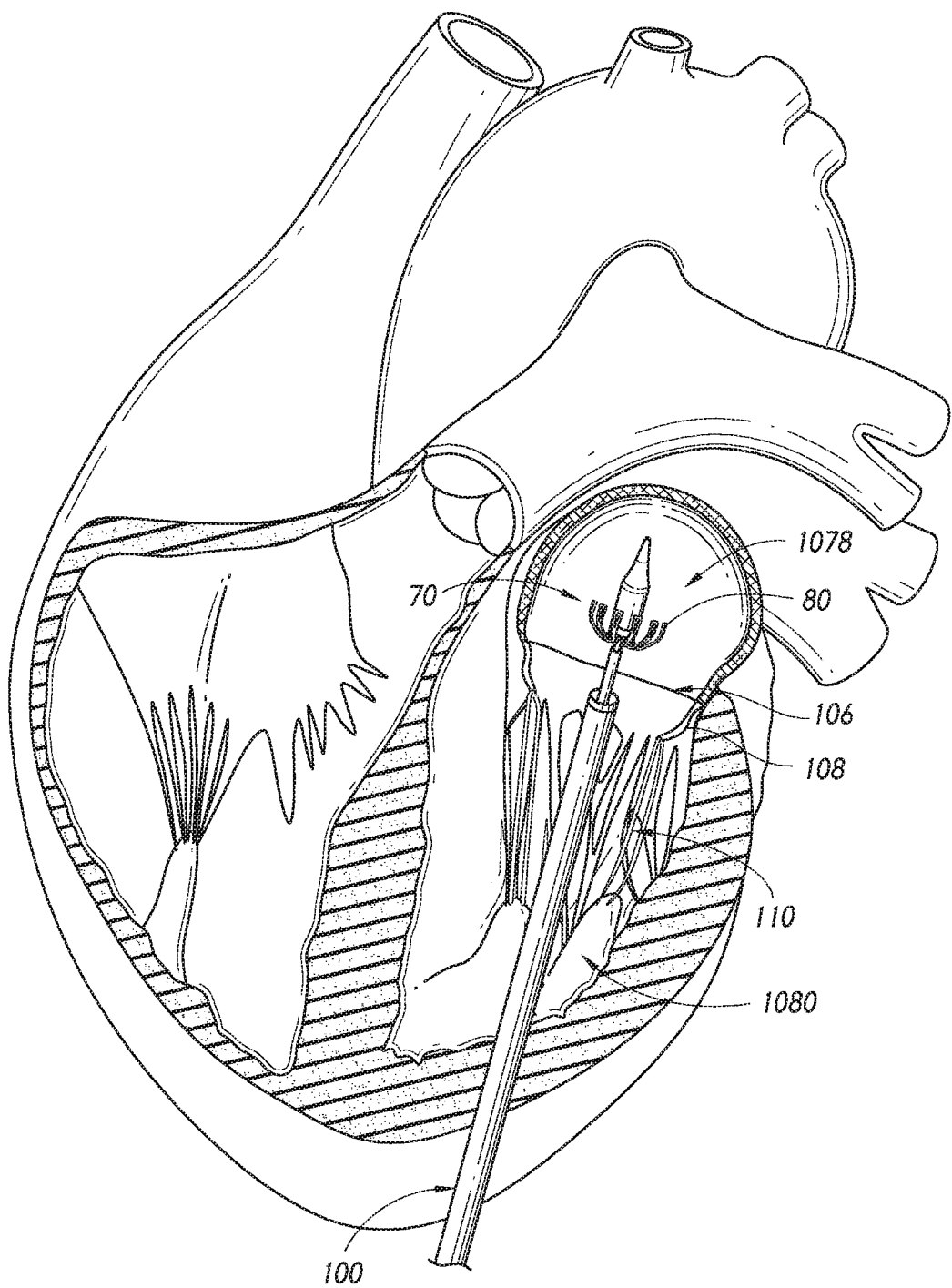

An embodiment of the position of the delivery system 100 for release of the ventricular anchors 80 is shown in FIG. 30A (tether 136 removed for clarity). As shown, the ventricular anchors 80 can be released in the left atrium 1078.

In some embodiments, only the ventricular anchors 80 are released from the delivery system 100. In some embodiments, the ventricular end of the implant 70 does not expand with released of the ventricular anchors 80. However, in some embodiments, one or more of the ventricular anchors 80 can be released in either the left atrium 1078 (e.g., super-annular release), generally aligned with the mitral valve annulus 106 (e.g., intra-annular release), or just below the mitral valve annulus 106 (e.g., sub-annular release). In some embodiments, all of the distal anchors 1024 can be released together. In other embodiments, a subset of the distal anchors 1024 can be released while at a first position and another subset of the distal anchors 1024 can be released while at a second position.

As discussed in detail above, upon release from the delivery system 10, the ventricular anchors 80 can flip from extending distally to extending proximally. Accordingly, in some embodiments, the ventricular anchors 80 can be flipped in either the left atrium 1078 (e.g., super-annular flip), generally aligned with the mitral valve annulus 106 (e.g., intra-annular flip), or below the mitral valve annulus 106 (e.g., sub-annular flip). The distal anchors 1024 can be released and flipped in the left atrium 1078 (or generally aligned with the mitral valve annulus 106) or in the left ventricle 1080. The atrial anchors 82 can remain within the delivery system 10. In some embodiments, all of the distal anchors 1024 can be flipped together. In other embodiments, a subset of the distal anchors 1024 can be flipped while at a first position and another subset of the distal anchors 1024 can be released while at a second position. For example, some of the distal anchors 1024 can be flipped in the left atrium 1078 and some of the distal anchors 1024 can be flipped while generally aligned with the mitral valve annulus 106 or just below the mitral valve annulus 106.

In some embodiments, the ventricular anchors 80 may be position in line with the annulus 106 in the non-flipped position. In some embodiments, the ventricular anchors 80 may be position in line with the annulus 106 in the flipped position. In some embodiments, the ventricular anchors 80 may be just below the annulus 106 in the non-flipped position. In some embodiments, the ventricular anchors 80 may be just below the annulus 106 in the flipped position. In some embodiments, prior to flipping the ventricular side of the implant 70 can be located within or below the mitral valve annulus 106. However, flipping the anchors can cause, without any other movement of the delivery system 100, the ventricular side of the implant 70/anchors 80 to move upwards, moving it into the left atrium 1078 or moving it in line with the mitral annulus 106. Thus, in some embodiments the ventricular anchors 80 can begin flipping at the annulus 106 but be fully within the left atrium 1078 upon flipping. In some embodiments the ventricular anchors 80 can begin flipping below the annulus 106 but be generally in line with the annulus 106 upon flipping.

In some embodiments, the ventricular anchors 80 can be distal (e.g., toward the left atrium 1078) of a free edge of the mitral leaflets 108 upon release and flipping, such as shown in FIG. 16A. In some embodiments, the ventricular anchors 80 can be aligned with (e.g., toward the left atrium 1078) a free edge of the mitral leaflets 108 upon release and flipping. In some embodiments, the ventricular anchors 80 can be distal (e.g., toward the left atrium 1078) of a free edge of the mitral valve annulus 106 upon release and flipping. In some embodiments, the ventricular anchors 80 can be aligned with (e.g., toward the left atrium 1078) a free edge of the mitral valve annulus 106 upon release and flipping. In some embodiments, the ventricular anchors 80 can be proximal (e.g., toward the left ventricle 1080) of a free edge of the mitral leaflets 108 upon release and flipping.

Thus, in some embodiments the ventricular anchors 80 can be released/flipped above where the chordae 110 attach to the free edge of the native leaflets 108. In some embodiments the ventricular anchors 80 can be released/flipped above where some the chordae 110 attach to the free edge of the native leaflets 108. In some embodiments the ventricular anchors 80 can be released/flipped above where all the chordae 110 attach to the free edge of the native leaflets 108. In some embodiments, the ventricular anchors 80 can be released/flipped above the mitral valve annulus 106. In some embodiments, the ventricular anchors 80 can be released/flipped above the mitral valve leaflets 108. In some embodiments, the ventricular anchors 80 can be released/flipped generally in line with the mitral valve annulus 106. In some embodiments, the ventricular anchors 80 can be released/flipped generally in line with the mitral valve leaflets 108. In some embodiments, the tips of the ventricular anchors 80 can be released/flipped generally in line with the mitral valve annulus 106. In some embodiments, the tips of the ventricular anchors 80 can be released/flipped generally in line with the mitral valve leaflets 108. In some embodiments the ventricular anchors 80 can be released/flipped below where some the chordae 110 attach to the free edge of the native leaflets 108. In some embodiments the ventricular anchors 80 can be released/flipped below where all the chordae 110 attach to the free edge of the native leaflets 108. In some embodiments, the ventricular anchors 80 can be released/flipped below the mitral valve annulus 106. In some embodiments, the ventricular anchors 80 can be released/flipped below the mitral valve leaflets 108.

Figure 30B:
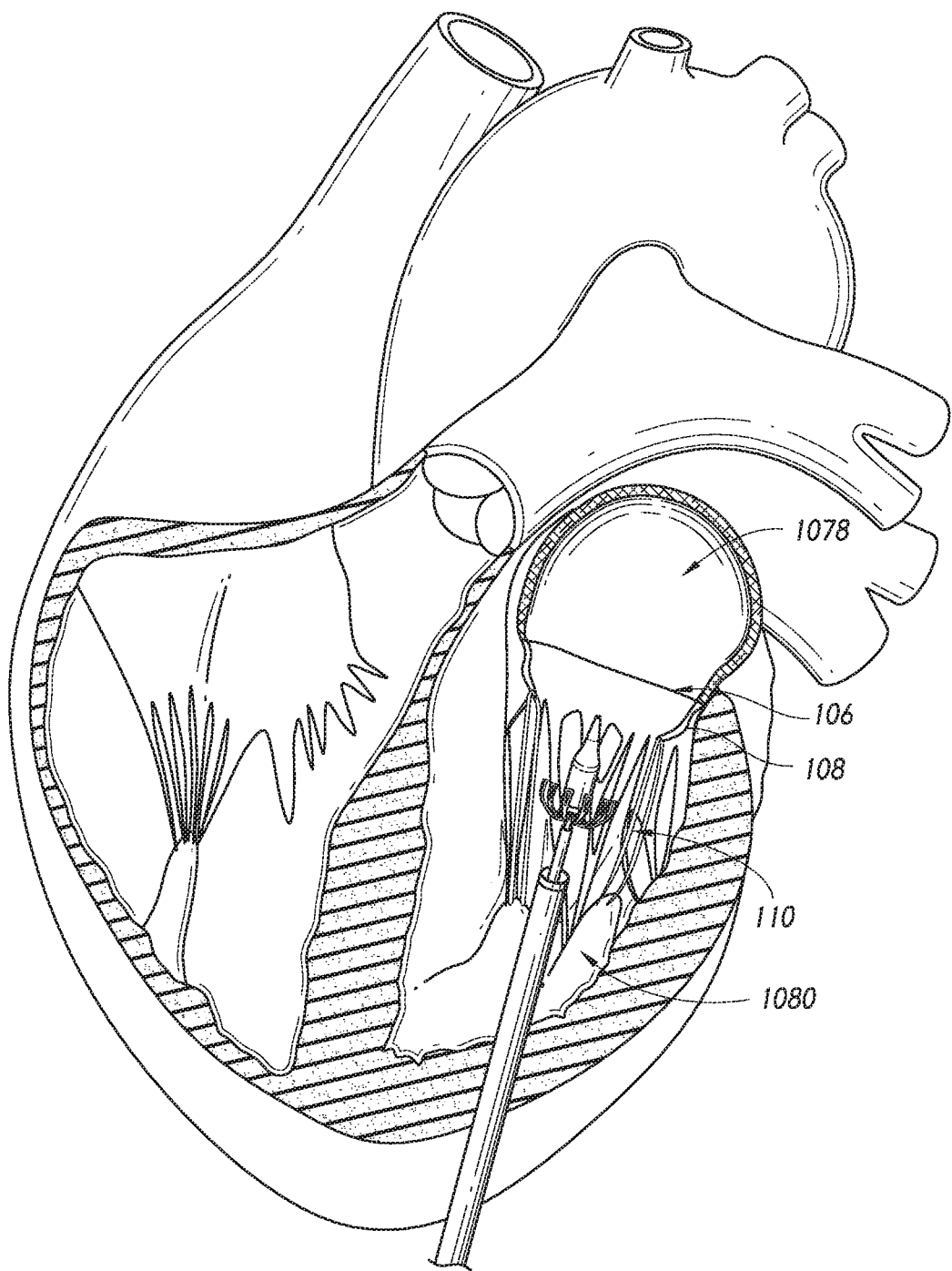

Once the ventricular anchors 80 are released and flipped, the delivery system 100 can be translated back towards the left ventricle 1080 through the mitral valve annulus 106 so that the ventricular anchors 80 enter the left ventricle 1080 as shown in FIG. 30B. In some embodiments, the ventricular anchors 80 compress when passing through the mitral valve annulus 106. In some embodiments, the implant 70 can compress when passing through the mitral valve annulus 106. In some embodiments, the implant 70 does not compress when it passes through the mitral annulus 106. The system 100 can be released anywhere within the left ventricle 1080 between the papillary heads and the leaflets 108.

In some embodiments, the ventricular anchors 80 are fully expanded prior to passing through the mitral valve annulus 106, such as the tether 136 being fully released. In some embodiments, the ventricular anchors 80 are partially expanded prior to passing through the mitral valve annulus 106, such as the tether 136 maintaining tension, and continued operation of the delivery system 100 can fully expand the ventricular anchors 80 in the left ventricle 1080.

When the ventricular anchors 80 enter the left ventricle 1080, the ventricular anchors 80 can pass through the chordae 110 and move behind the mitral valve leaflets 108, thereby capturing the leaflets 108. In some embodiments, the ventricular anchors 80 and/or other parts of the implant 70 can push the chordae 110 and/or the mitral valve leaflets 108 outwards.

Thus, after release of the ventricular anchors 80, the delivery system 100 can then be repositioned as needed so that the ends of the left ventricular anchors 80 are at the same level of the free edge of the native mitral valve leaflets as shown in FIG. 30B. The delivery system 10 can also be positioned to be coaxial to the mitral annulus 106 if possible while still reducing contact with the left ventricular wall, the left atrial wall, and/or the annulus 106.

Figure 30C:
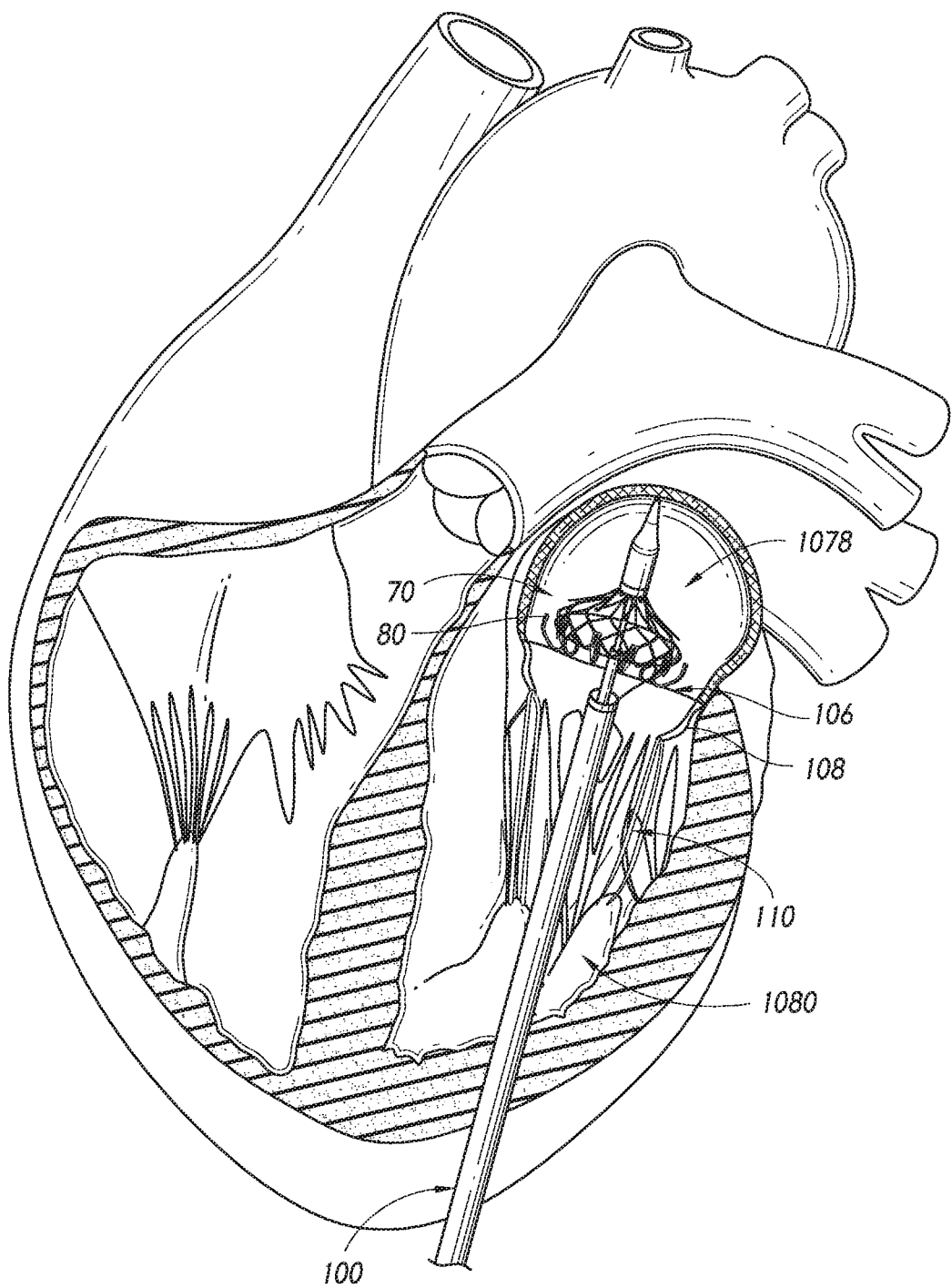
Figure 30D:
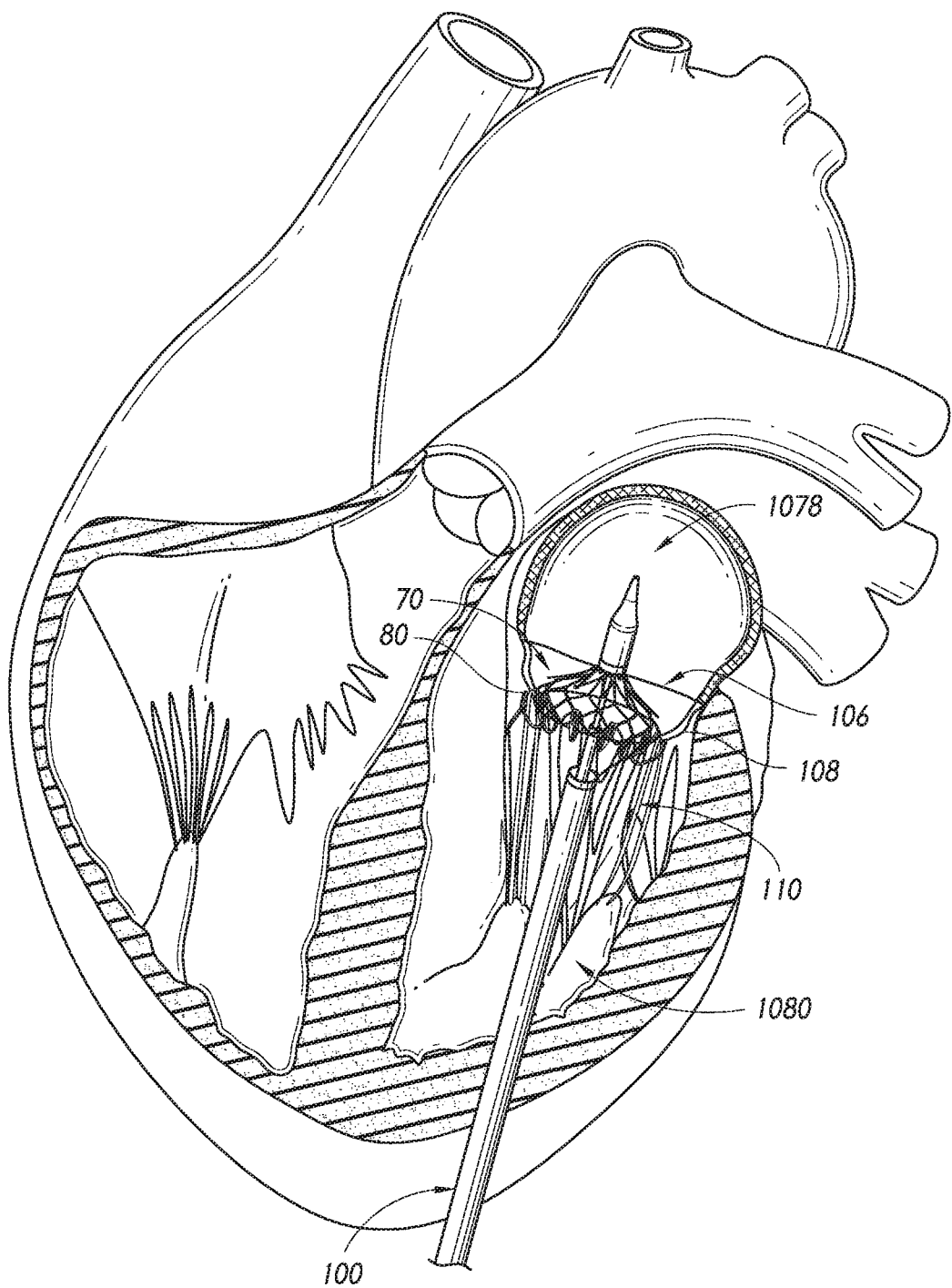

As shown above, in some embodiments, only the distal anchors 1024 are released in the left atrium 1078 before the prosthesis 1010 is move to a position within, or below, the annulus. In some alternate embodiments, the distal end of the implant 70 can be further expanded in the left atrium 1078, as shown in FIG. 30C. Thus, instead of the ventricular anchors 80 flipping and no portion of the implant 70 body expanding, a portion of the implant 70 can be exposed and allowed to expand in the left atrium 1078. This partially exposed implant 70 can then be passed through the annulus 106 into the left ventricle 1080, such as shown in FIG. 30D. Further, the atrial anchors 82 can be exposed. This is an alternative methodology as compared to FIGS. 30A-B. In some embodiments, the entirety of the prosthesis 1010 can be expanded within the left atrium 1078.

To facilitate passage through the annulus 106, the delivery system 10 can include a leader element (not shown) which passes through the annulus 106 prior to the prosthesis 10 passing through the annulus 106. For example, the leader element can include an expandable member, such as an expandable balloon, which can help maintain the shape, or expand, the annulus 106. The leader element can have a tapered or rounded shape (e.g., conical, frustoconical, semi-spherical) to facilitate positioning through and expansion of the annulus 106. In some embodiments, the delivery system 10 can include an engagement element (not shown) which can apply a force on the prosthesis 1010 to force the prosthesis 1010 through the annulus 106. For example, the engagement element can include an expandable member, such as an expandable balloon, positioned within or above the prosthesis 1010. In some embodiments, the engagement element can include one or more tethers.

However, if only the ventricular anchors 80 are flipped, and no other expansion occurs such as shown in FIGS. 30A-B, the expansion shown in FIG. 30C can be skipped and the prosthesis can instead be partially expanded in the ventricle 1080 to the position shown in FIG. 30D. Thus, when the implant 70 is in the proper location, the distal end can be allowed to expand to capture the leaflets 108. If the distal end is already expanded, such as from FIG. 30C, no more expansion may take place or the distal end can be further expanded.

Figure 30E:
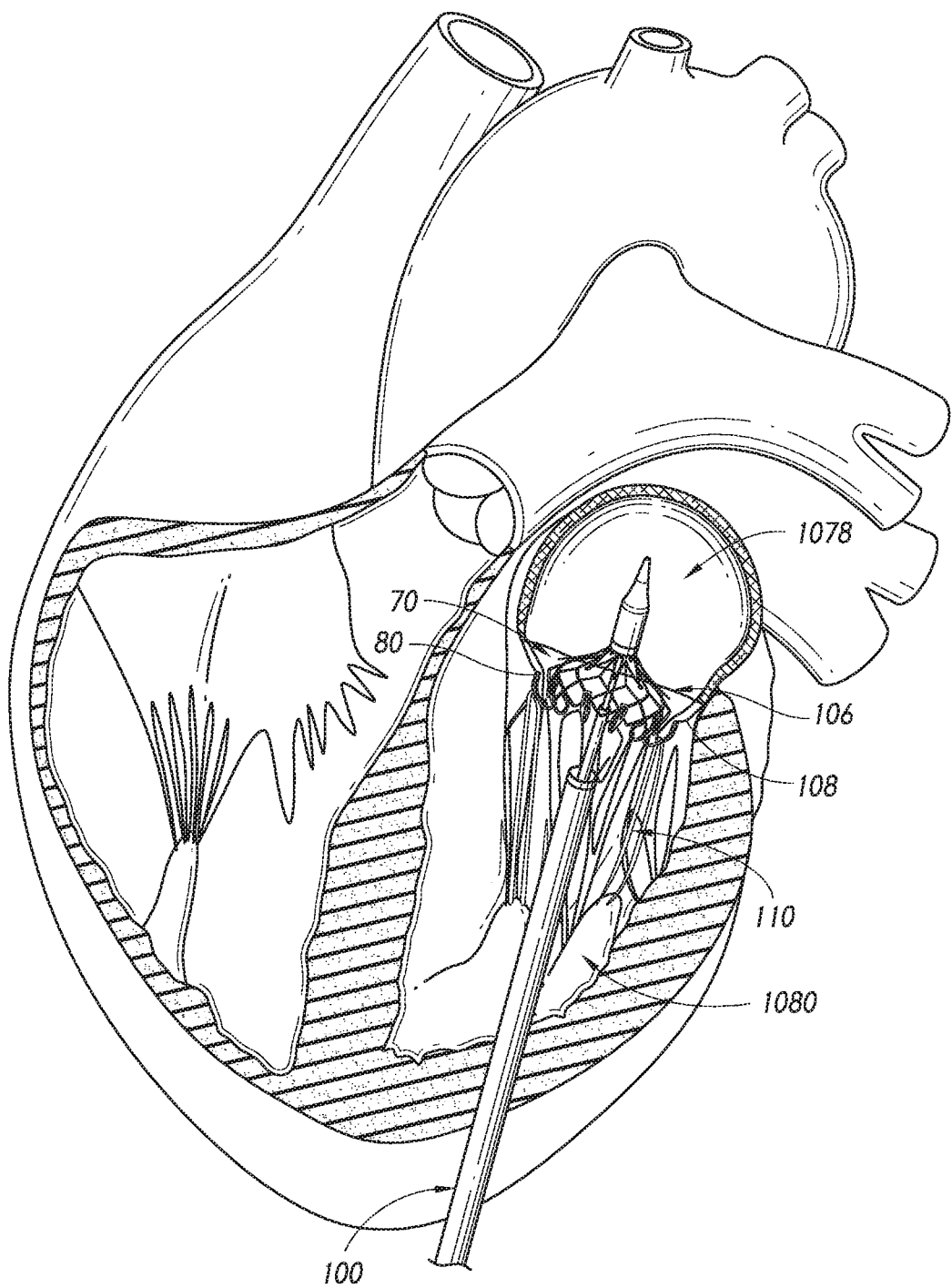

Further, the PML and AML 108 can be captured, for example by adjusting the depth and angle of the implant 70. FIG. 30E shows the position of the implant 70 after capturing the leaflets 108. If a larger prosthesis diameter is needed to capture the leaflets 108, the elongate hollow member shaft 114 can be retracted until the desired diameter of the implant 70 is achieved. Capture of the leaflets 108 can be confirmed through echo imaging. In some embodiments, a user can confirm that the implant 70 is still in the appropriate depth and has not advanced into the left ventricle 1080. The position can be adjusted as needed.

In some embodiments, once the ventricular anchors 80 enter the left ventricle 1080 the system 100 can be pushed upwards (e.g., towards the left atrium 1078) to fully capture the leaflets 108 as shown in FIG. 30E. In some embodiments, the system 100 does not need to be pulled backwards to capture the leaflets 108. In some embodiments, systolic pressure can push the leaflets 108 upwards to be captured by the ventricular anchors 80. In some embodiments, a user can rotate the delivery system 10 and/or prosthesis 1010 prior to and/or while pulling the delivery system 10 backwards. In some instances, this can beneficially engage a greater number of chordae tendineae.

The delivery system 100 can be maneuvered to be coaxial and height relative to the mitral annulus 106, such as by translating or rotating the delivery system 100. As needed, the implant 70 can be repositioned to capture the free edge of the native mitral valve leaflets 108. Once full engagement of the leaflets 108 is confirmed, the implant 70 can be set perpendicular (or generally perpendicular) to the mitral annular plane. The tether 136 can continue to be released to continue expansion of the implant 70.

Figure 30F:
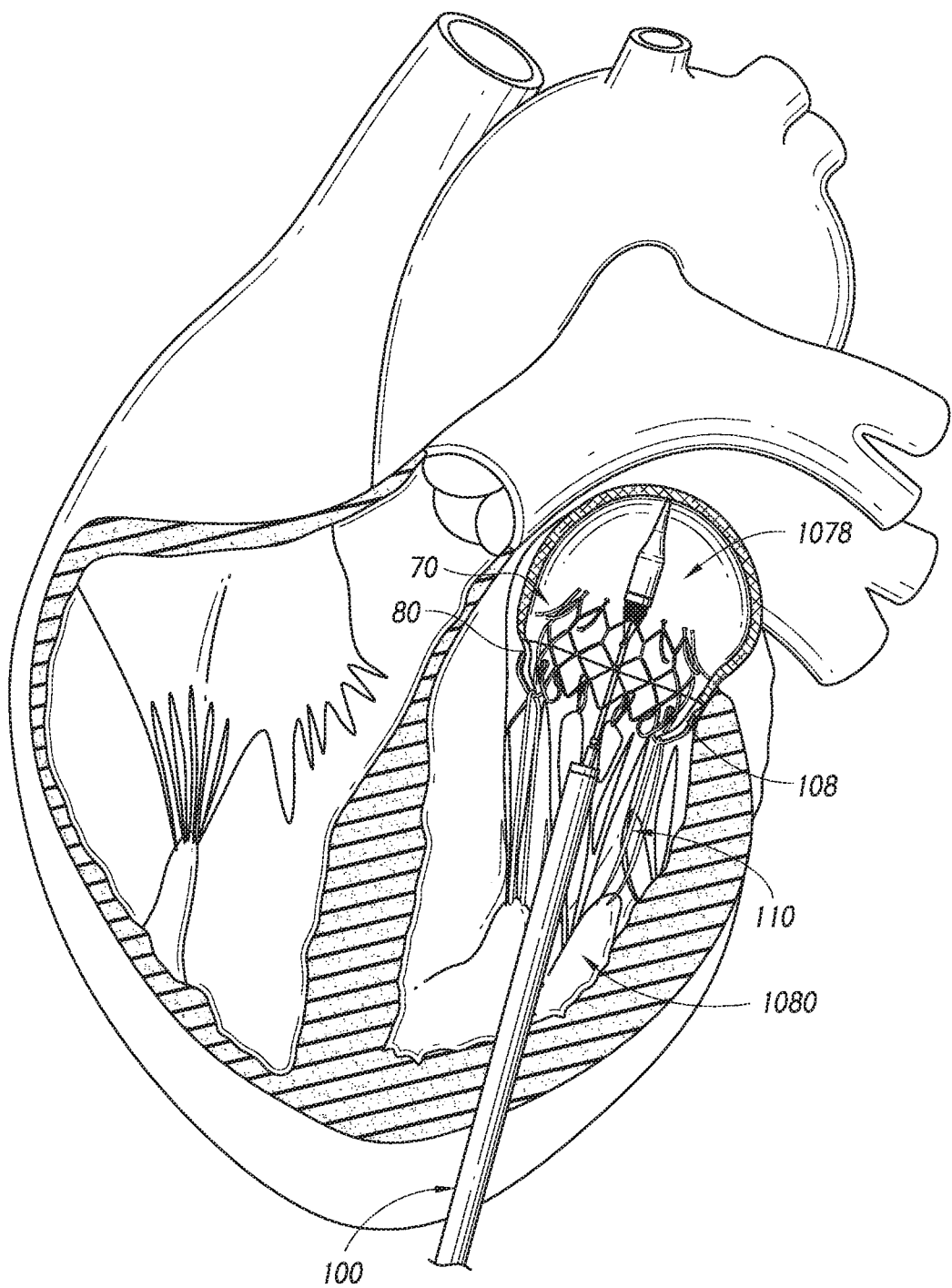

Following, the nose cone 118 can be advanced until the left atrial anchors 82 are exposed and the implant 70 expanded as shown in FIG. 30F. The nose cone 118 can then be reversed in direction to relieve any tension on the delivery system 100.

In some embodiments, atrial anchors 82 may not be released from the system 10 until the ventricular anchors 80 have captured the leaflets 108. In some embodiments, atrial anchors 82 may be released from the system 10 prior to the ventricular anchors 80 capturing the leaflets 108. In some embodiments, the atrial anchors 82 can be released when the ventricular anchors 80 are super or intra annular and the expanded implant 70 (either partially or fully expanded) can be translated through the mitral annulus 106.

After, the leaflet capture and positioning of the implant 70 can be confirmed, along with the relatively perpendicular position with respect to the mitral annular plane. Proper positioning of the implant 70 can be confirmed using TEE and fluoroscopic imaging.

Following, the delivery system 100 can be centralized within the implant 70. The nose cone 118 can be translated to be flush with the inner retention ring 132. The delivery system 100 can then be retracted into the left atrium 1078 and removed.

This intra-super annulus release can have a number of advantageous. For example, this allows the ventricular anchors 80 to be properly aligned when contacting the chordae 110. If the ventricular anchors 80 were released in the left ventricle 1080, this could cause misalignment or damage to heart tissue, such as the leaflets 108 or chordae 110.

Figure 31A:
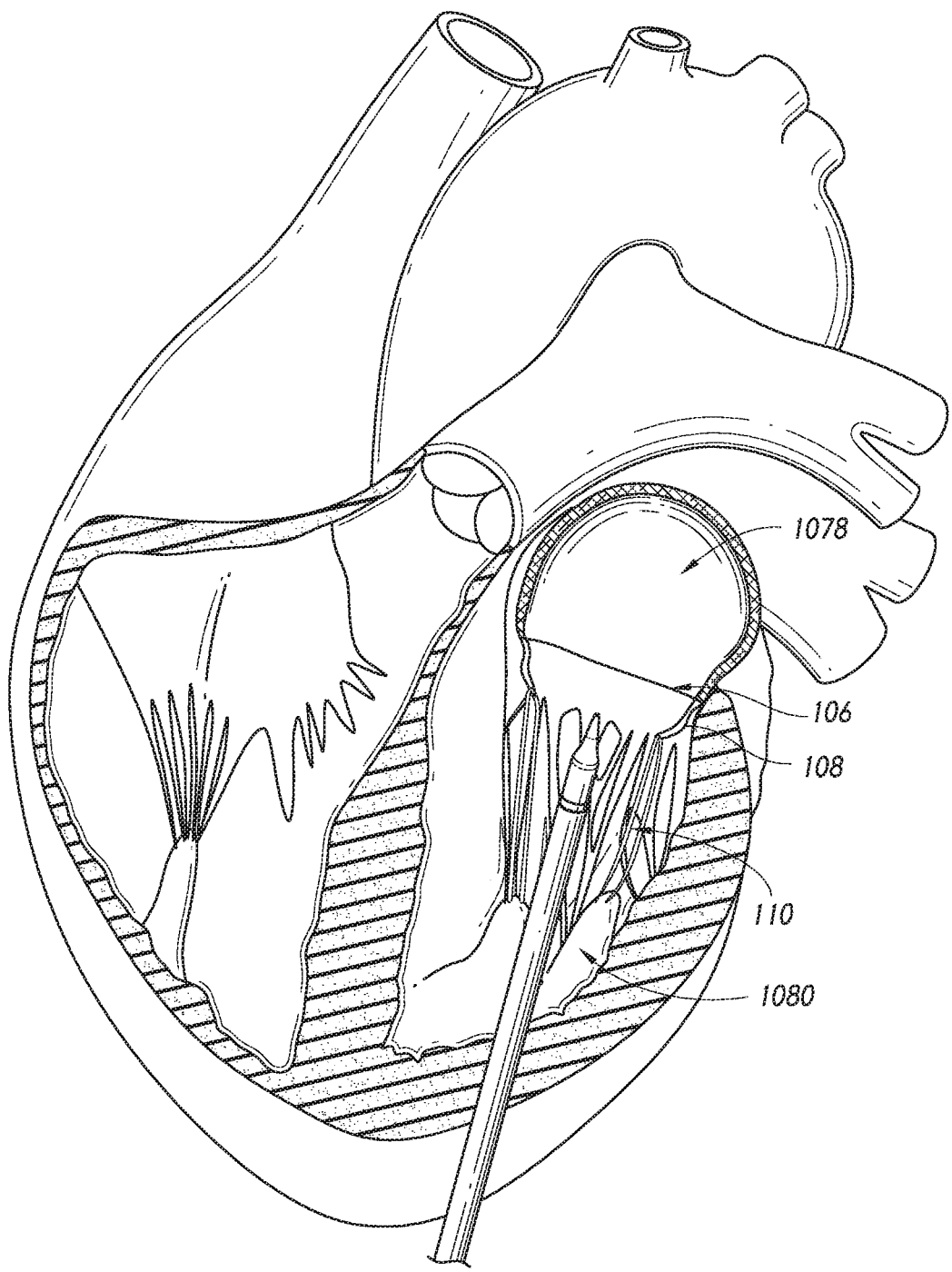
Figure 31B:
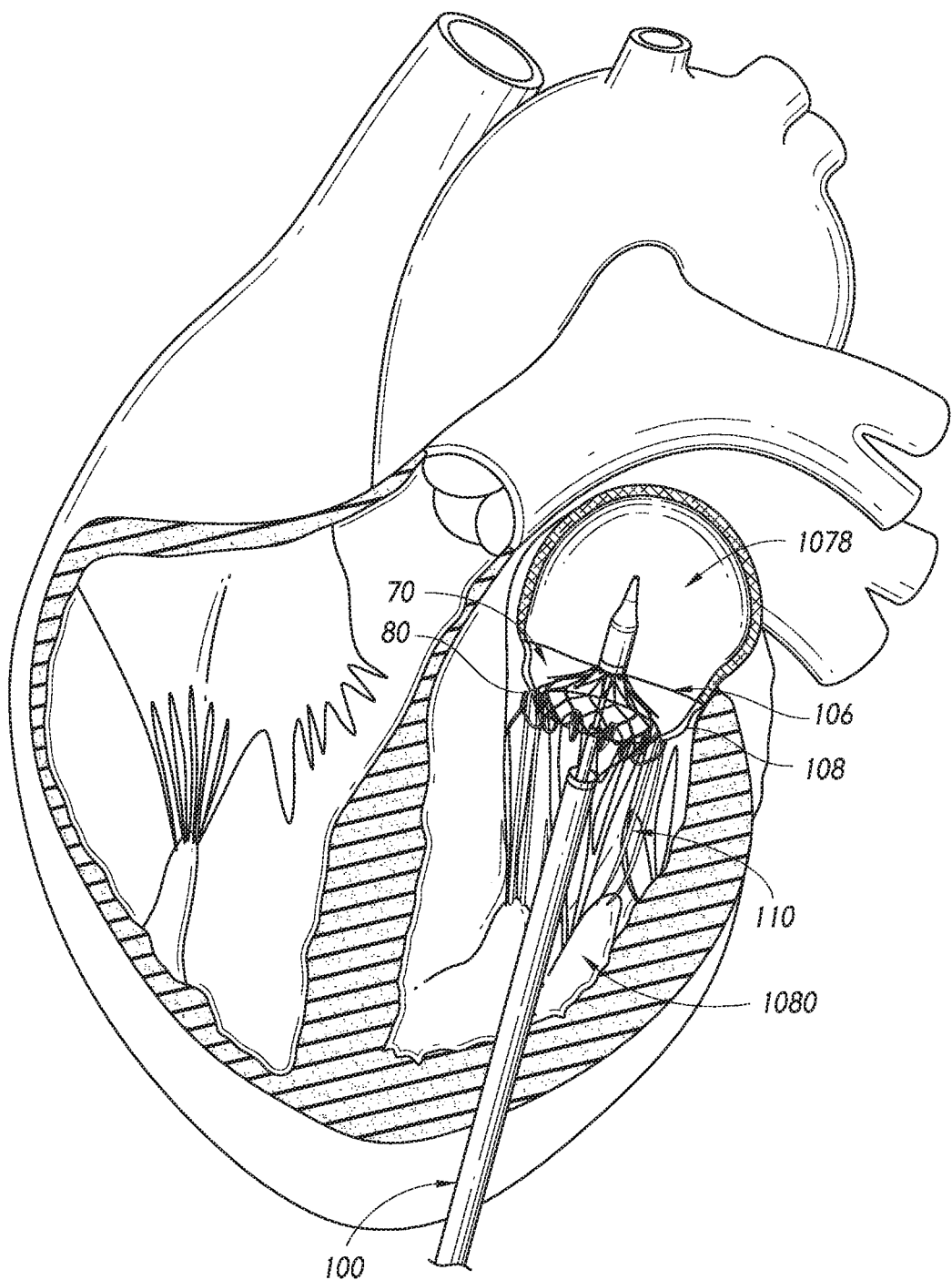

FIGS. 31A-B illustrate an alternate approach to releasing the implant 70. As shown in FIG. 31A, the delivery system 100 can be translated into the left ventricle 1080 prior to release of the implant 70. Thus, the ventricular end of the implant 70, and thus the ventricular anchors 80, can be released and flipped partially, or fully within the left ventricle 1080 as shown in FIG. 31A. Accordingly, in some embodiments the anchors 80 can be released/flipped below the mitral annulus 106, and/or below the free edges of the leaflets 108. Further, the anchors 80 can be released above the papillary heads 2004. Similar methodology as discussed above can then be used to properly position the implant 70 and remove the delivery system 100 to deliver the implant 70 into the position shown in FIG. 30F. In some embodiments, a waist of the implant 70 can be even with the free edge of the leaflets 108 during release. In some embodiments, the ventricular anchors 80 may release in the ventricle 1080 without expansion of the implant 70 body, such as discussed in detail above with respect to FIGS. 30A-B.

In any of the procedures described herein, a user can utilize rapid pacing at any step of the process. In some instances, this can facilitate positioning and/or anchoring of the prosthesis 1010 to native tissue. For example, the movement of the native mitral valve leaflets can be significantly reduced by rapid pacing for facilitating placement of the ventricular anchors behind the native mitral valve leaflets.

From the foregoing description, it will be appreciated that an inventive product and approaches for implant delivery systems are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount. If the stated amount is 0 (e.g., none, having no), the above recited ranges can be specific ranges, and not within a particular % of the value. For example, within less than or equal to 10 wt./vol. % of, within less than or equal to 5 wt./vol. % of, within less than or equal to 1 wt./vol. % of, within less than or equal to 0.1 wt./vol. % of, and within less than or equal to 0.01 wt./vol. % of the stated amount.

Some embodiments have been described in connection with the accompanying drawings. The figures are drawn to scale, but such scale should not be limiting, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims.

What is claimed is:

1. A method for delivering a replacement mitral valve with a delivery system, the method comprising:
    delivering a distal end of the delivery system containing the replacement mitral valve into a left atrium of a heart, wherein the replacement mitral valve is in a radially compressed condition in the delivery system;
    releasing a first set of anchors of the replacement mitral valve from the radially compressed condition in the left atrium or in line with a native mitral valve annulus, wherein releasing the first set of anchors causes the anchors to flip positions from the radially compressed condition;
    translating the first set of anchors into a left ventricle of the heart after the releasing the first set of anchors; and
    fully releasing the replacement mitral valve prosthesis from the delivery system into an expanded condition.

2. The method of claim 1, wherein the replacement mitral valve further comprises a second set of anchors spaced from the first set of anchors.

3. The method of claim 2, further comprising releasing the second set of anchors in the left atrium.

4. The method of claim 1, further comprising translating the replacement mitral valve towards the left atrium after passing the first set of anchors through the native mitral valve annulus.

5. The method of claim 4, wherein translating the replacement mitral towards the left atrium captures a native mitral valve leaflet with the first set of anchors.

6. The method of claim 1, wherein the first set of anchors flip from extending proximally to extending distally or flip from extending distally to extending proximally upon releasing the first set of anchors.

7. The method of claim 1, wherein the first set of anchors pass between chordae of the left ventricle.

8. The method of claim 1, wherein the replacement mitral valve comprises a single frame.

9. The method of claim 1, wherein delivering the distal end of the delivery system comprises delivering in a transapical delivery approach.

10. The method of claim 1, wherein delivering the distal end of the delivery system comprises delivering in a transseptal delivery approach.

11. The method of claim 1, further comprising rotating the delivery system after the releasing the first set of anchors.

12. The method of claim 1, wherein the fully releasing the replacement mitral valve comprises loosening a tether wrapped at least partially around the replacement mitral valve.

13. The method of claim 1, wherein the delivery system comprises a plurality of sleeves which can slide with respect to one another in order to release the replacement mitral valve.

14. The method of claim 1, wherein the first set of anchors is released in line with the native mitral valve annulus.

15. The method of claim 1, wherein the first set of anchors is released in the left atrium.

16. The method of claim 15, wherein translating the first set of anchors into the left ventricle of the heart comprises passing the first set of anchors through the native mitral valve annulus.

17. A method for delivering a replacement mitral valve with a delivery system, the method comprising:
- delivering a distal end of the delivery system containing the replacement mitral valve into a left atrium of a heart, the replacement mitral valve having a self-expandable main body, a first set of anchors coupled to a distal end portion of the main body and a valve assembly supported by the main body, wherein the replacement mitral valve is maintained in a radially compressed condition in the delivery system with the first set of anchors extending from the distal end portion of the main body with ends of the first set of anchors extending generally distally;
- releasing the first set of anchors from the delivery system in the left atrium, wherein releasing the first set of anchors causes the anchors to reverse orientation such that the ends of the first set of anchors extend generally proximally;
- advancing the first set of anchors through a native mitral valve annulus into a left ventricle of the heart after the releasing the first set of anchors; and
- releasing the main body of the replacement mitral valve from the delivery system and allowing the main body to self-expand into an expanded condition within the native mitral valve annulus.

18. The method of claim 17, wherein the replacement mitral valve is delivered into the left atrium by advancing the replacement mitral valve through an atrial septum.

19. The method of claim 17, wherein the main body of the replacement valve includes an outer frame and an inner frame, wherein the outer frame is conformable for placement in the native mitral valve annulus and the inner frame supports the valve assembly.

20. A method for delivering a replacement mitral valve with a delivery system, the method comprising:
- delivering a distal end of the delivery system containing the replacement mitral valve into a left atrium of a heart, the replacement mitral valve having a self-expandable main body, a first set of anchors coupled to a distal end portion of the main body and a valve assembly supported by the main body, wherein the replacement mitral valve is maintained in a radially compressed condition in the delivery system with the first set of anchors extending from the distal end portion of the main body with ends of the first set of anchors extending generally distally;
- releasing the first set of anchors from the delivery system within a native mitral valve annulus, wherein releasing the first set of anchors causes the anchors to reverse orientation such that the ends of the first set of anchors extend generally proximally;
- after the releasing the first set of anchors, advancing the first set of anchors into a left ventricle of the heart; and
- releasing the main body of the replacement mitral valve from the delivery system and allowing the main body to self-expand into an expanded condition.

* * * * *